(12) United States Patent
Sramek et al.

(10) Patent No.: US 11,992,275 B2
(45) Date of Patent: May 28, 2024

(54) ROBOTICALLY CONTROLLABLE FIELD GENERATORS FOR DETECTING DISTORTIONS

(71) Applicant: AURIS HEALTH, INC., Redwood City, CA (US)

(72) Inventors: Christopher Sramek, Half Moon Bay, CA (US); Elif Ayvali, Redwood City, CA (US); David Burdick Berman, San Mateo, CA (US)

(73) Assignee: Auris Health, Inc., Redwood City, CA (US)

( * ) Notice: Subject to any disclaimer, the term of this patent is extended or adjusted under 35 U.S.C. 154(b) by 338 days.

(21) Appl. No.: 17/412,144

(22) Filed: Aug. 25, 2021

(65) Prior Publication Data
US 2022/0061927 A1 Mar. 3, 2022

Related U.S. Application Data

(60) Provisional application No. 63/216,990, filed on Jun. 30, 2021, provisional application No. 63/084,979, (Continued)

(51) Int. Cl.
*A61B 34/20* (2016.01)
*A61B 34/00* (2016.01)
(Continued)

(52) U.S. Cl.
CPC .............. *A61B 34/20* (2016.02); *A61B 34/30* (2016.02); *A61B 34/32* (2016.02); *A61B 34/37* (2016.02);
(Continued)

(58) Field of Classification Search
CPC .... A61B 2017/00725; A61B 2034/107; A61B 2034/2051; A61B 2034/2059;
(Continued)

(56) References Cited

U.S. PATENT DOCUMENTS

| 10,932,861 B2 | 3/2021 | Sramek et al. |
| 11,324,554 B2 | 5/2022 | Lee et al. |

(Continued)

FOREIGN PATENT DOCUMENTS

| CN | 111278380 A | 6/2020 |
| JP | 2019506919 A | 3/2019 |

(Continued)

OTHER PUBLICATIONS

Notice of Allowance for U.S. Appl. No. 17/412,136 dated Jun. 12, 2023, 12 pages.

(Continued)

*Primary Examiner* — Michael T Rozanski
(74) *Attorney, Agent, or Firm* — Chang & Hale LLP

(57) ABSTRACT

Certain aspects relate to systems with robotically controllable field generators and applications thereof. In one application, a robotic medical system, comprising a first robotic arm coupled to an electromagnetic (EM) field generator configured to generate an EM field, an EM sensor, and a processor. The processor may be configured to transmit a command to the first robotic arm to cause movement of the EM field generator along a robotic trajectory while the EM sensor remains at a location. An EM sensor trajectory of the EM sensor within the EM field corresponding to a period of time in which the EM field generator moved along the robotic trajectory may be detected. The robotic trajectory and the EM sensor trajectory may be analyzed to determine a difference between the robotic trajectory and the EM sensor trajectory; and EM distortion at the location may be detected comparing the difference and a threshold.

20 Claims, 60 Drawing Sheets

Related U.S. Application Data filed on Sep. 29, 2020, provisional application No. 63/084,950, filed on Sep. 29, 2020, provisional application No. 63/070,472, filed on Aug. 26, 2020.

(51) Int. Cl.
| | | |
|---|---|---|
| *A61B 34/30* | (2016.01) | |
| *A61B 34/32* | (2016.01) | |
| *A61B 34/37* | (2016.01) | |
| *B25J 9/16* | (2006.01) | |
| *B25J 19/02* | (2006.01) | |

(52) U.S. Cl.
CPC ............ *A61B 34/70* (2016.02); *B25J 9/1653* (2013.01); *B25J 9/1664* (2013.01); *B25J 19/027* (2013.01); *A61B 2034/2051* (2016.02); *A61B 2034/301* (2016.02); *A61B 2034/302* (2016.02)

(58) Field of Classification Search
CPC ...... A61B 2034/2061; A61B 2034/301; A61B 2034/302; A61B 2090/306; A61B 2090/309; A61B 2090/376; A61B 2090/378; A61B 2090/397; A61B 2090/571; A61B 34/20; A61B 34/30; A61B 34/32; A61B 34/37; A61B 34/70; B25J 19/027; B25J 5/007; B25J 9/0087; B25J 9/1653; B25J 9/1664; B25J 9/1689; G05B 2219/45118
See application file for complete search history.

(56) References Cited

U.S. PATENT DOCUMENTS

| | | | |
|---|---|---|---|
| 11,324,558 | B2 | 5/2022 | Graetzel et al. |
| 11,395,703 | B2 | 7/2022 | Berman et al. |
| 2007/0015991 | A1 | 1/2007 | Fu et al. |
| 2018/0279852 | A1 | 10/2018 | Rafii-Tari et al. |
| 2019/0000560 | A1 | 1/2019 | Berman et al. |
| 2020/0008874 | A1 | 1/2020 | Barbagli et al. |
| 2020/0246088 | A1 | 8/2020 | Mewes et al. |

FOREIGN PATENT DOCUMENTS

| | | |
|---|---|---|
| WO | 2015166487 A1 | 11/2015 |
| WO | 2017103862 A1 | 6/2017 |

OTHER PUBLICATIONS

Conti, F. et al., "Interface Design and Control Strategies for a Robot Assisted Ultrasonic Examination System", Experimental Robotics, Part of the Springer Tracts in Advanced Robotics book series (STAR, vol. 79) 2010, 14 pages.

Interntaional Search Report for appl. No. PCT/IB2021/057795, dated Mar. 10, 2022, 6 pages.

Non-Final Rejection for U.S. Appl. No. 17/412,136, dated Jan. 13, 2023, 14 pages.

Reichl, T. et al., "Electromagnetic Servoing—A New Tracking Paradigm", IEEE Transactions on Medical Imaging, Aug. 8, 2013, vol. 32, No. 8, pp. 1526-1535, 10 pages.

Written Opinion for appl No. PCT/IB2021/057795, dated Mar. 10, 2022, 8 pages.

Notice of Allowance for U.S. Appl. No. 17/412,136, dated Oct. 25, 2023, 2 pages.

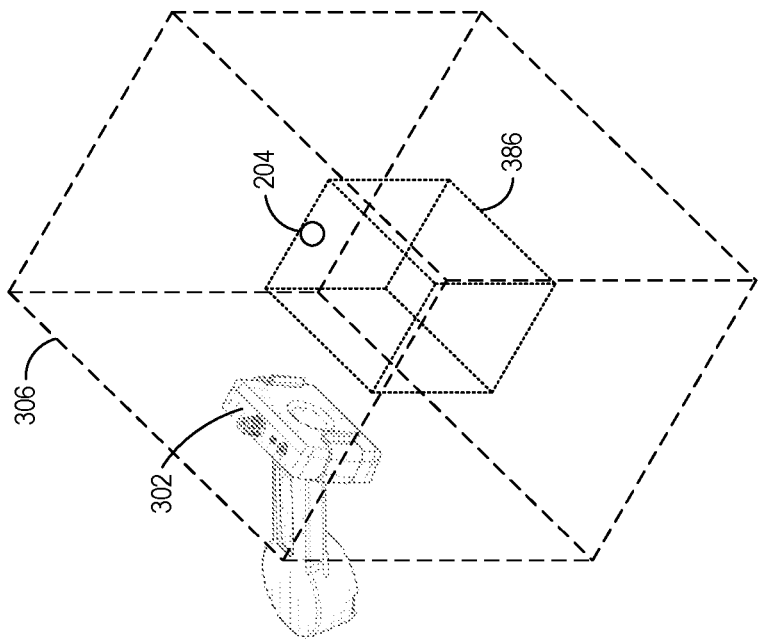
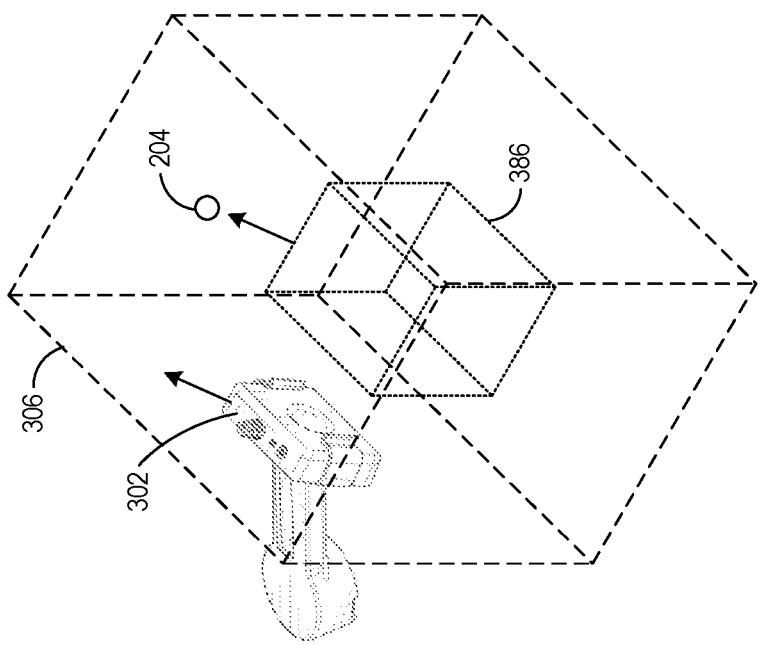

ROBOTICALLY CONTROLLABLE FIELD GENERATORS FOR DETECTING DISTORTIONS

RELATED APPLICATIONS

This application claims priority to following, the disclosures of which are hereby incorporated by reference in their entirety: U.S. Provisional Application No. 63/070,472, filed Aug. 26, 2020, and entitled ROBOTICALLY CONTROLLABLE FIELD GENERATORS FOR ROBOTIC MEDICAL SYSTEMS; U.S. Provisional Application No. 63/084,979, filed Sep. 29, 2020, and entitled ROBOTICALLY CONTROLLABLE FIELD GENERATORS FOR ROBOTIC MEDICAL SYSTEMS; U.S. Provisional Application No. 63/084,950, filed Sep. 29, 2020, and entitled ROBOTICALLY CONTROLLABLE FIELD GENERATORS FOR ROBOTIC MEDICAL SYSTEMS; and U.S. Provisional Application No. 63/216,990, filed Jun. 30, 2021, and entitled ROBOTICALLY CONTROLLABLE FIELD GENERATORS FOR ROBOTIC MEDICAL SYSTEMS.

TECHNICAL FIELD

The systems and methods disclosed herein are directed to field generators for robotic medical systems, and more particularly, to robotically positionable and/or controllable field generators for detecting distortions in a medical systems as well as related devices, systems, and methods.

BACKGROUND

Medical procedures such as laparoscopy or endoscopy may involve accessing and visualizing an internal region of a patient. In a laparoscopic procedure, a medical instrument can be inserted into the internal region through a laparoscopic access port. In an endoscopic procedure, a thin, flexible tubular medical instrument may be inserted into the internal region through a natural patient orifice. The medical instrument can include an end effector configured to perform a function during the procedure.

In certain procedures, a robotically-enabled medical system may be used to control the insertion and/or manipulation of the medical instrument and end effector. The robotically-enabled medical system may include a robotic arm, or other instrument positioning device, having a manipulator assembly used to control the positioning of the instrument during the procedure.

The robotically-enabled medical system may be configured to determine the position of the medical instrument based on an output of one or more positions sensors that can be positioned on the medical instrument.

SUMMARY

A robotic medical system can include an electromagnetic (EM) field generator that is configured to couple to (or otherwise be integrated into) a robotic arm of the system. Such EM field generators can be considered robotically controllable or positionable as they can be controlled or repositioned using the robotic arm. The EM field generator can produce a magnetic field within which the positions of one or more EM sensors can be determined. Because the EM field generator is coupled to the robotic arm, the kinematics of the robotic arm can be used to establish a registration between an EM coordinate frame of the EM field generator and a robotic coordinate frame or a global coordinate frame of the system.

This arrangement can reduce or eliminate the need for more complex registration steps that can require user input to establish a relationship between the EM coordinate frame and the robotic or global coordinate frame. This arrangement can also improve the accuracy with which the positions of the EM sensors are determined by, for example, improving the setup of the field generator corresponding robotic arms, tracking the medical instruments, detecting distortion that may impact the sensors of the systems, and facilitate sensor fusion with additional modalities.

These and other features and advantages of the robotically controllable or positionable EM field generators will be described in more detail below. The systems, methods and devices of this disclosure each have several innovative aspects, no single one of which is solely responsible for the desirable attributes disclosed herein.

BRIEF DESCRIPTION OF THE DRAWINGS

The disclosed aspects will hereinafter be described in conjunction with the appended drawings, provided to illustrate and not to limit the disclosed aspects, wherein like designations denote like elements.

FIGS. 31A and 31B are perspective views that illustrate an example of moving an EM field generator with a robotic arm such that an EM sensor is positioned at within a predetermined region within an EM field., according to an example embodiment

DETAILED DESCRIPTION

1. Overview.

Aspects of the present disclosure may be integrated into a robotically-enabled medical system capable of performing a variety of medical procedures, including both minimally invasive, such as laparoscopy, and non-invasive, such as endoscopy, procedures. Among endoscopic procedures, the system may be capable of performing bronchoscopy, ureteroscopy, gastroscopy, etc.

In addition to performing the breadth of procedures, the system may provide additional benefits, such as enhanced imaging and guidance to assist the physician. Additionally, the system may provide the physician with the ability to perform the procedure from an ergonomic position without the need for awkward arm motions and positions. Still further, the system may provide the physician with the ability to perform the procedure with improved ease of use such that one or more of the instruments of the system can be controlled by a single user.

Various embodiments will be described below in conjunction with the drawings for purposes of illustration. It should be appreciated that many other implementations of the disclosed concepts are possible, and various advantages can be achieved with the disclosed implementations. Headings are included herein for reference and to aid in locating various sections. These headings are not intended to limit the scope of the concepts described with respect thereto. Such concepts may have applicability throughout the entire specification.

A. Robotic System—Cart.

Figure 1:
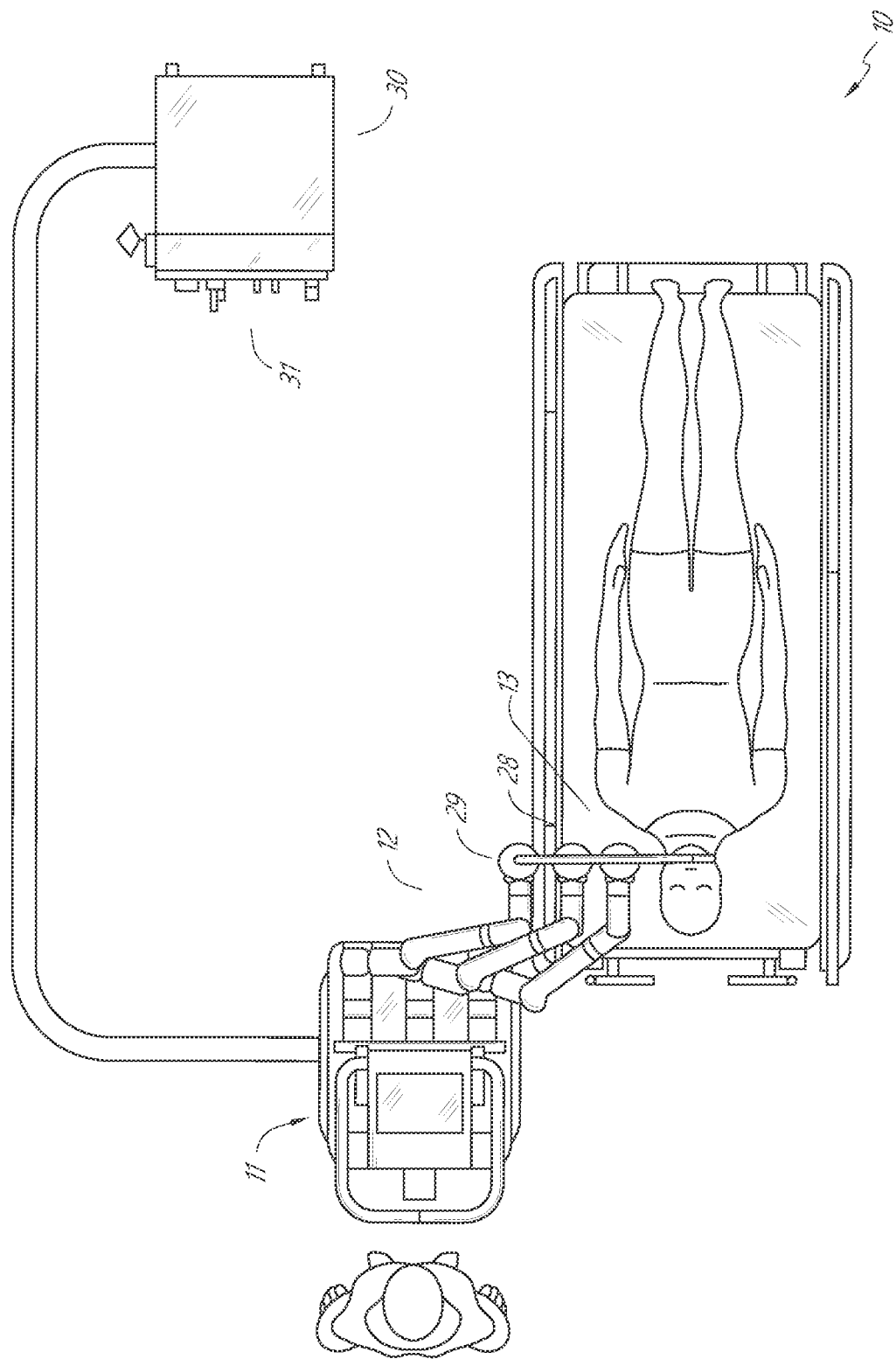
FIG. 1 illustrates an embodiment of a cart-based robotic system arranged for diagnostic and/or therapeutic bronchoscopy, according to an example embodiment.
Figure 2:
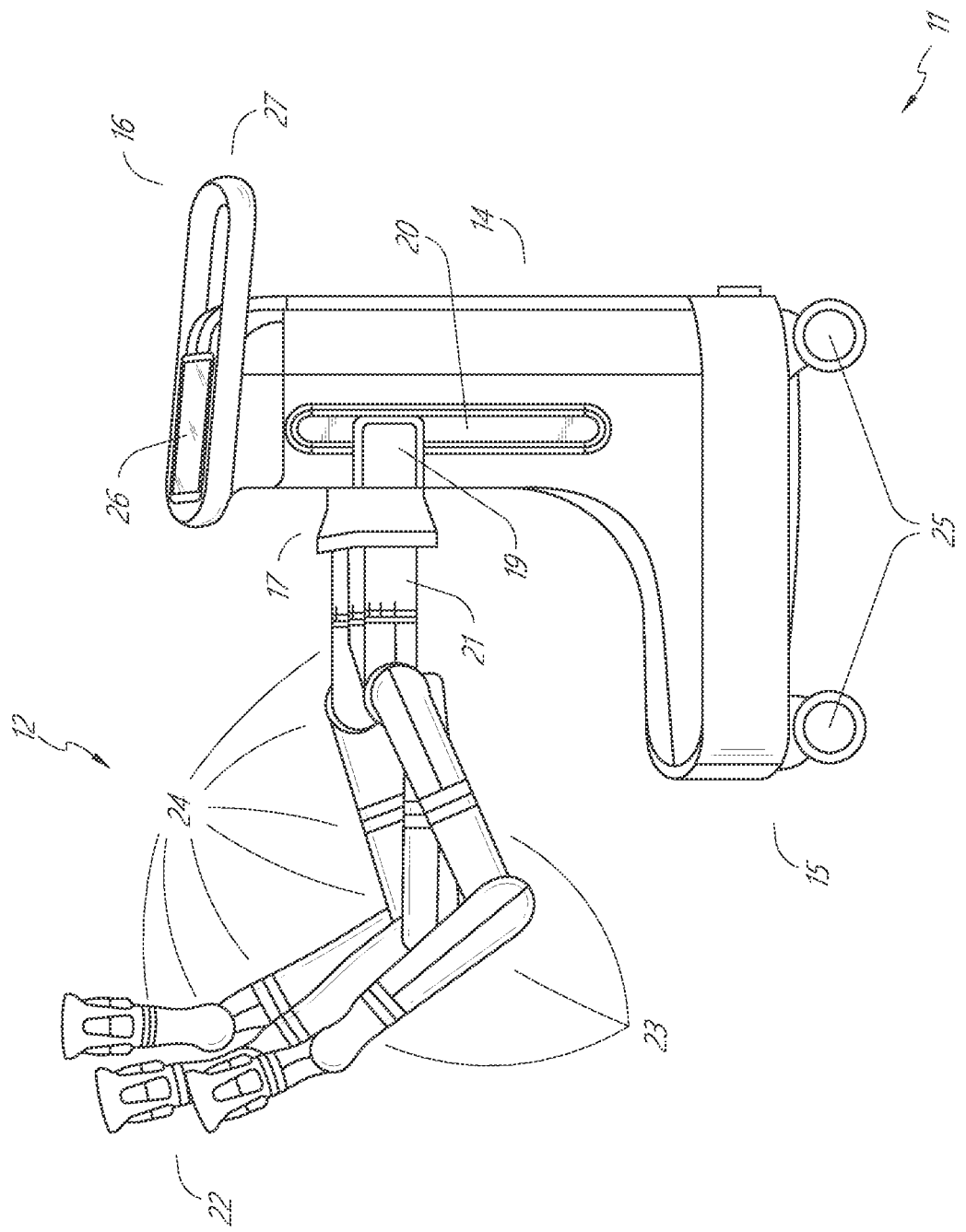
FIG. 2 depicts further aspects of the robotic system of FIG. 1, according to an example embodiment.

The robotically-enabled medical system may be configured in a variety of ways depending on the particular procedure. FIG. 1 illustrates an embodiment of a cart-based robotically-enabled system 10 arranged for a diagnostic and/or therapeutic bronchoscopy. During a bronchoscopy, the system 10 may comprise a cart 11 having one or more robotic arms 12 to deliver a medical instrument, such as a steerable endoscope 13, which may be a procedure-specific bronchoscope for bronchoscopy, to a natural orifice access point (i.e., the mouth of the patient positioned on a table in the present example) to deliver diagnostic and/or therapeutic tools. As shown, the cart 11 may be positioned proximate to the patient's upper torso in order to provide access to the access point. Similarly, the robotic arms 12 may be actuated to position the bronchoscope relative to the access point. The arrangement in FIG. 1 may also be utilized when performing a gastro-intestinal (GI) procedure with a gastroscope, a specialized endoscope for GI procedures. FIG. 2 depicts an example embodiment of the cart in greater detail.

With continued reference to FIG. 1, once the cart 11 is properly positioned, the robotic arms 12 may insert the steerable endoscope 13 into the patient robotically, manually, or a combination thereof. As shown, the steerable endoscope 13 may comprise at least two telescoping parts, such as an inner leader portion and an outer sheath portion, each portion coupled to a separate instrument driver from the set of instrument drivers 28, each instrument driver coupled to the distal end of an individual robotic arm. This linear arrangement of the instrument drivers 28, which facilitates coaxially aligning the leader portion with the sheath portion, creates a "virtual rail" 29 that may be repositioned in space by manipulating the one or more robotic arms 12 into different angles and/or positions. The virtual rails described herein are depicted in the Figures using dashed lines, and accordingly the dashed lines do not depict any physical structure of the system. Translation of the instrument drivers 28 along the virtual rail 29 telescopes the inner leader portion relative to the outer sheath portion or advances or retracts the endoscope 13 from the patient. The angle of the virtual rail 29 may be adjusted, translated, and pivoted based on clinical application or physician preference. For example, in bronchoscopy, the angle and position of the virtual rail 29 as shown represents a compromise between providing physician access to the endoscope 13 while minimizing friction that results from bending the endoscope 13 into the patient's mouth.

The endoscope 13 may be directed down the patient's trachea and lungs after insertion using precise commands from the robotic system until reaching the target destination or operative site. In order to enhance navigation through the patient's lung network and/or reach the desired target, the endoscope 13 may be manipulated to telescopically extend the inner leader portion from the outer sheath portion to obtain enhanced articulation and greater bend radius. The use of separate instrument drivers 28 also allows the leader portion and sheath portion to be driven independently of each other.

For example, the endoscope 13 may be directed to deliver a biopsy needle to a target, such as, for example, a lesion or nodule within the lungs of a patient. The needle may be deployed down a working channel that runs the length of the endoscope to obtain a tissue sample to be analyzed by a pathologist. Depending on the pathology results, additional tools may be deployed down the working channel of the endoscope for additional biopsies. After identifying a nodule to be malignant, the endoscope 13 may endoscopically deliver tools to resect the potentially cancerous tissue. In some instances, diagnostic and therapeutic treatments can be delivered in separate procedures. In those circumstances, the endoscope 13 may also be used to deliver a fiducial to "mark" the location of the target nodule as well. In other instances, diagnostic and therapeutic treatments may be delivered during the same procedure.

The system 10 may also include a movable tower 30, which may be connected via support cables to the cart 11 to provide support for controls, electronics, fluidics, optics, sensors, and/or power to the cart 11. Placing such functionality in the tower 30 allows for a smaller form factor cart 11 that may be more easily adjusted and/or re-positioned by an operating physician and his/her staff. Additionally, the division of functionality between the cart/table and the support tower 30 reduces operating room clutter and facilitates improving clinical workflow. While the cart 11 may be positioned close to the patient, the tower 30 may be stowed in a remote location to stay out of the way during a procedure.

In support of the robotic systems described above, the tower 30 may include component(s) of a computer-based control system that stores computer program instructions, for example, within a non-transitory computer-readable storage medium such as a persistent magnetic storage drive, solid state drive, etc. The execution of those instructions, whether the execution occurs in the tower 30 or the cart 11, may control the entire system or sub-system(s) thereof. For example, when executed by a processor of the computer system, the instructions may cause the components of the robotics system to actuate the relevant carriages and arm mounts, actuate the robotics arms, and control the medical instruments. For example, in response to receiving the control signal, the motors in the joints of the robotics arms may position the arms into a certain posture.

The tower 30 may also include a pump, flow meter, valve control, and/or fluid access in order to provide controlled irrigation and aspiration capabilities to the system that may be deployed through the endoscope 13. These components may also be controlled using the computer system of the tower 30. In some embodiments, irrigation and aspiration capabilities may be delivered directly to the endoscope 13 through separate cable(s).

The tower 30 may include a voltage and surge protector designed to provide filtered and protected electrical power to the cart 11, thereby avoiding placement of a power transformer and other auxiliary power components in the cart 11, resulting in a smaller, more moveable cart 11.

The tower 30 may also include support equipment for the sensors deployed throughout the robotic system 10. For example, the tower 30 may include optoelectronics equipment for detecting, receiving, and processing data received from the optical sensors or cameras throughout the robotic system 10. In combination with the control system, such optoelectronics equipment may be used to generate real-time images for display in any number of consoles deployed throughout the system, including in the tower 30. Similarly, the tower 30 may also include an electronic subsystem for receiving and processing signals received from deployed electromagnetic (EM) sensors. The tower 30 may also be used to house and position an EM field generator for detection by EM sensors in or on the medical instrument.

The tower 30 may also include a console 31 in addition to other consoles available in the rest of the system, e.g., console mounted on top of the cart. The console 31 may include a user interface and a display screen, such as a touchscreen, for the physician operator. Consoles in the system 10 are generally designed to provide both robotic controls as well as preoperative and real-time information of the procedure, such as navigational and localization information of the endoscope 13. When the console 31 is not the only console available to the physician, it may be used by a second operator, such as a nurse, to monitor the health or vitals of the patient and the operation of the system 10, as well as to provide procedure-specific data, such as navigational and localization information. In other embodiments, the console 31 is housed in a body that is separate from the tower 30.

The tower 30 may be coupled to the cart 11 and endoscope 13 through one or more cables or connections (not shown). In some embodiments, the support functionality from the tower 30 may be provided through a single cable to the cart 11, simplifying and de-cluttering the operating room. In other embodiments, specific functionality may be coupled in separate cabling and connections. For example, while power may be provided through a single power cable to the cart 11, the support for controls, optics, fluidics, and/or navigation may be provided through a separate cable.

FIG. 2 provides a detailed illustration of an embodiment of the cart 11 from the cart-based robotically-enabled system shown in FIG. 1. The cart 11 generally includes an elongated support structure 14 (often referred to as a "column"), a cart base 15, and a console 16 at the top of the column 14. The column 14 may include one or more carriages, such as a carriage 17 (alternatively "arm support") for supporting the deployment of one or more robotic arms 12 (three shown in FIG. 2). The carriage 17 may include individually configurable arm mounts that rotate along a perpendicular axis to adjust the base of the robotic arms 12 for better positioning relative to the patient. The carriage 17 also includes a carriage interface 19 that allows the carriage 17 to vertically translate along the column 14.

The carriage interface 19 is connected to the column 14 through slots, such as slot 20, that are positioned on opposite sides of the column 14 to guide the vertical translation of the carriage 17. The slot 20 contains a vertical translation interface to position and hold the carriage 17 at various vertical heights relative to the cart base 15. Vertical translation of the carriage 17 allows the cart 11 to adjust the reach of the robotic arms 12 to meet a variety of table heights, patient sizes, and physician preferences. Similarly, the individually configurable arm mounts on the carriage 17 allow the robotic arm base 21 of the robotic arms 12 to be angled in a variety of configurations.

In some embodiments, the slot 20 may be supplemented with slot covers that are flush and parallel to the slot surface to prevent dirt and fluid ingress into the internal chambers of the column 14 and the vertical translation interface as the carriage 17 vertically translates. The slot covers may be deployed through pairs of spring spools positioned near the vertical top and bottom of the slot 20. The covers are coiled within the spools until deployed to extend and retract from their coiled state as the carriage 17 vertically translates up and down. The spring-loading of the spools provides force to retract the cover into a spool when the carriage 17 translates towards the spool, while also maintaining a tight seal when the carriage 17 translates away from the spool. The covers may be connected to the carriage 17 using, for example, brackets in the carriage interface 19 to ensure proper extension and retraction of the cover as the carriage 17 translates.

The column 14 may internally comprise mechanisms, such as gears and motors, that are designed to use a vertically aligned lead screw to translate the carriage 17 in a mechanized fashion in response to control signals generated in response to user inputs, e.g., inputs from the console 16.

The robotic arms 12 may generally comprise robotic arm bases 21 and end effectors 22, separated by a series of linkages 23 that are connected by a series of joints 24, each joint comprising an independent actuator, each actuator comprising an independently controllable motor. Each independently controllable joint represents an independent degree of freedom available to the robotic arm 12. Each of the robotic arms 12 may have seven joints, and thus provide seven degrees of freedom. A multitude of joints result in a multitude of degrees of freedom, allowing for "redundant" degrees of freedom. Having redundant degrees of freedom allows the robotic arms 12 to position their respective end effectors 22 at a specific position, orientation, and trajectory in space using different linkage positions and joint angles. This allows for the system to position and direct a medical instrument from a desired point in space while allowing the physician to move the arm joints into a clinically advantageous position away from the patient to create greater access, while avoiding arm collisions.

The cart base 15 balances the weight of the column 14, carriage 17, and robotic arms 12 over the floor. Accordingly, the cart base 15 houses heavier components, such as electronics, motors, power supply, as well as components that either enable movement and/or immobilize the cart 11. For example, the cart base 15 includes rollable wheel-shaped casters 25 that allow for the cart 11 to easily move around the room prior to a procedure. After reaching the appropriate position, the casters 25 may be immobilized using wheel locks to hold the cart 11 in place during the procedure.

Positioned at the vertical end of the column 14, the console 16 allows for both a user interface for receiving user input and a display screen (or a dual-purpose device such as, for example, a touchscreen 26) to provide the physician user with both preoperative and intraoperative data. Potential preoperative data on the touchscreen 26 may include preoperative plans, navigation and mapping data derived from preoperative computerized tomography (CT) scans, and/or notes from preoperative patient interviews. Intraoperative data on display may include optical information provided from the tool, sensor and coordinate information from sensors, as well as vital patient statistics, such as respiration, heart rate, and/or pulse. The console 16 may be positioned and tilted to allow a physician to access the console 16 from the side of the column 14 opposite the carriage 17. From this position, the physician may view the console 16, robotic arms 12, and patient while operating the console 16 from behind the cart 11. As shown, the console 16 also includes a handle 27 to assist with maneuvering and stabilizing the cart 11.

Figure 3:
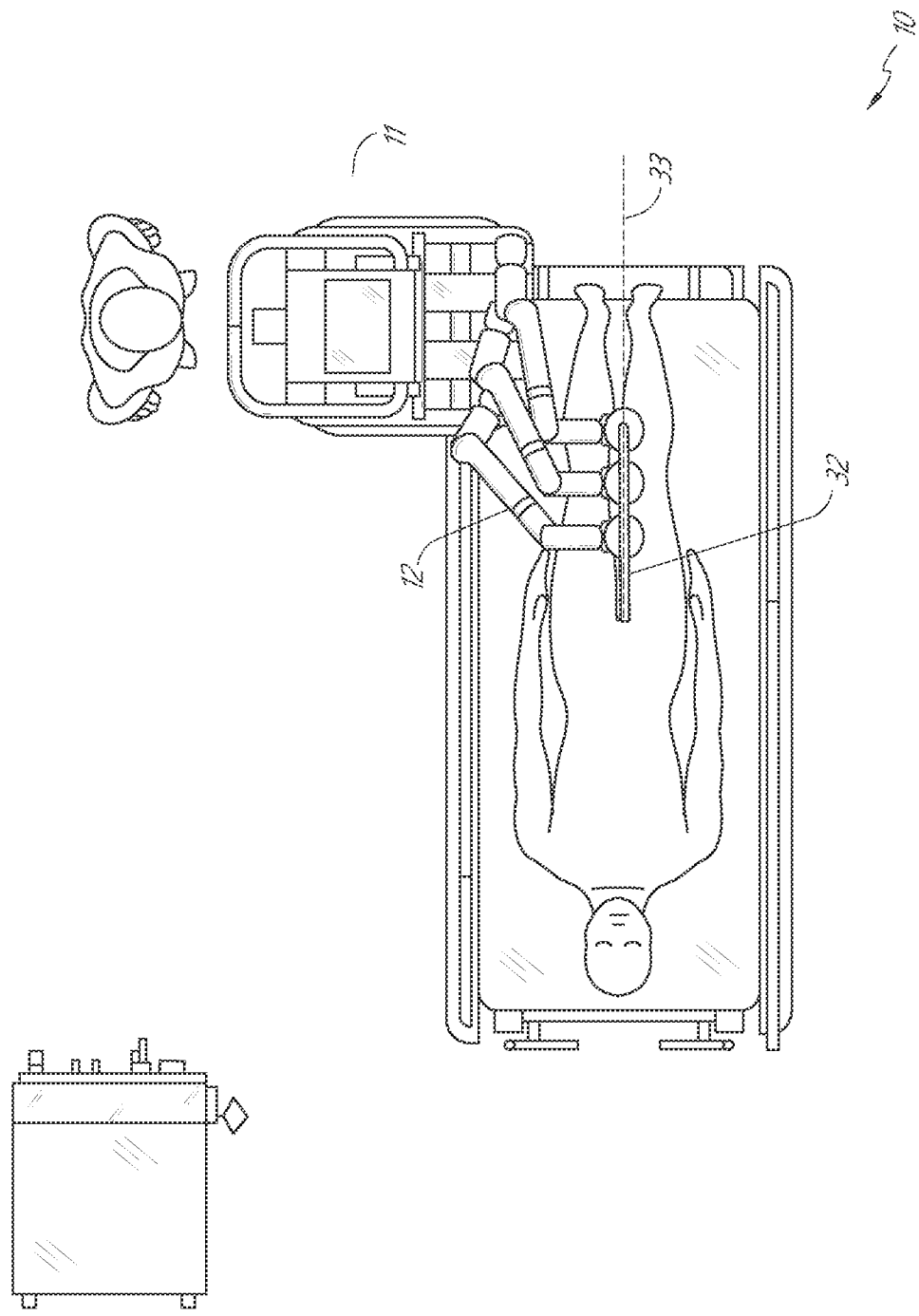
FIG. 3 illustrates an embodiment of the robotic system of FIG. 1 arranged for ureteroscopy, according to an example embodiment.

FIG. 3 illustrates an embodiment of a robotically-enabled system 10 arranged for ureteroscopy. In a ureteroscopic procedure, the cart 11 may be positioned to deliver a ureteroscope 32, a procedure-specific endoscope designed to traverse a patient's urethra and ureter, to the lower abdominal area of the patient. In a ureteroscopy, it may be desirable for the ureteroscope 32 to be directly aligned with the patient's urethra to reduce friction and forces on the sensitive anatomy in the area. As shown, the cart 11 may be aligned at the foot of the table to allow the robotic arms 12 to position the ureteroscope 32 for direct linear access to the patient's urethra. From the foot of the table, the robotic arms 12 may insert the ureteroscope 32 along the virtual rail 33 directly into the patient's lower abdomen through the urethra.

After insertion into the urethra, using similar control techniques as in bronchoscopy, the ureteroscope 32 may be navigated into the bladder, ureters, and/or kidneys for diagnostic and/or therapeutic applications. For example, the ureteroscope 32 may be directed into the ureter and kidneys to break up kidney stone build up using a laser or ultrasonic lithotripsy device deployed down the working channel of the ureteroscope 32. After lithotripsy is complete, the resulting stone fragments may be removed using baskets deployed down the ureteroscope 32.

Figure 4:
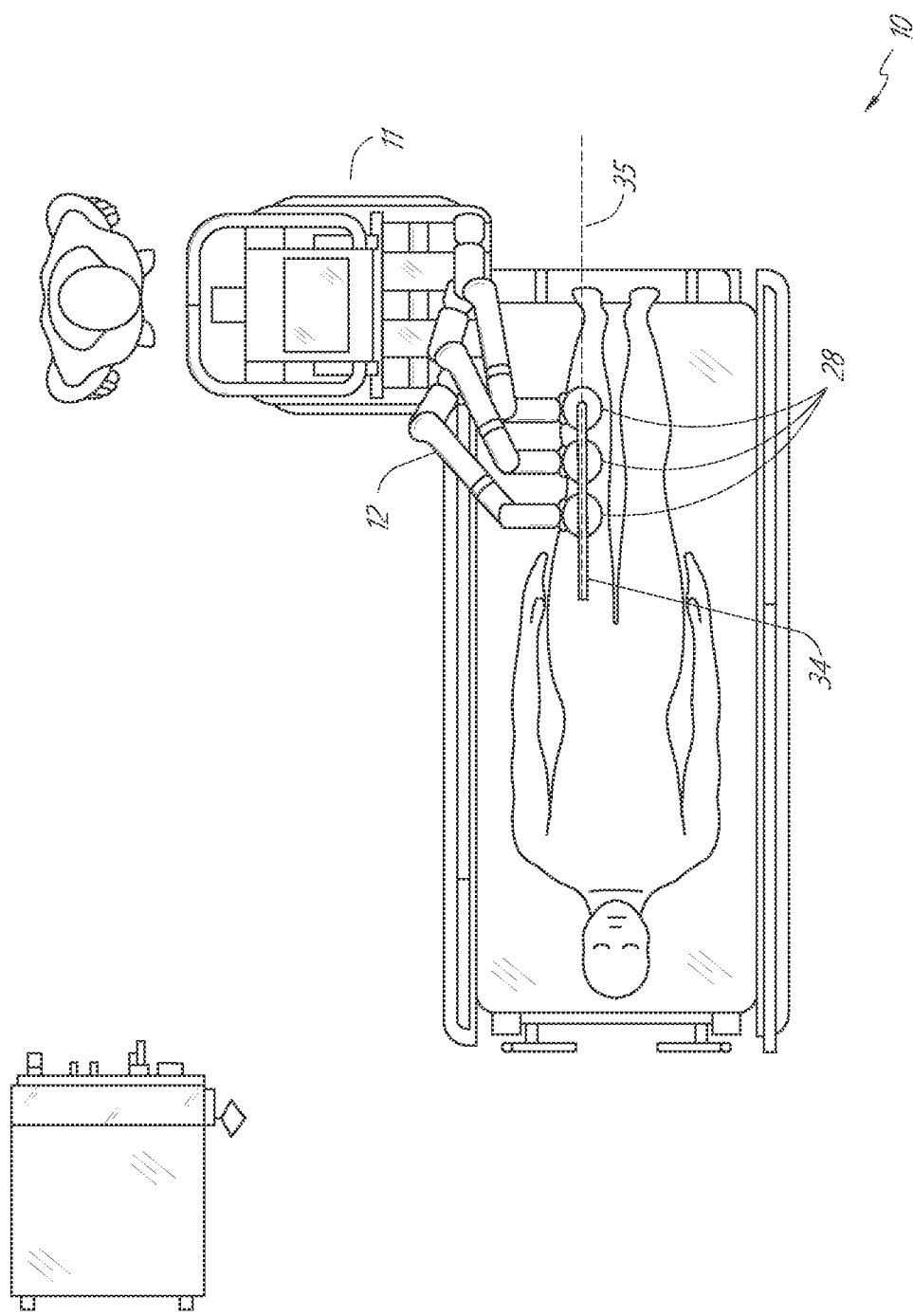
FIG. 4 illustrates an embodiment of the robotic system of FIG. 1 arranged for a vascular procedure, according to an example embodiment.

FIG. 4 illustrates an embodiment of a robotically-enabled system 10 similarly arranged for a vascular procedure. In a vascular procedure, the system 10 may be configured such that the cart 11 may deliver a medical instrument 34, such as a steerable catheter, to an access point in the femoral artery in the patient's leg. The femoral artery presents both a larger diameter for navigation as well as a relatively less circuitous and tortuous path to the patient's heart, which simplifies navigation. As in a ureteroscopic procedure, the cart 11 may be positioned towards the patient's legs and lower abdomen to allow the robotic arms 12 to provide a virtual rail 35 with direct linear access to the femoral artery access point in the patient's thigh/hip region. After insertion into the artery, the medical instrument 34 may be directed and inserted by translating the instrument drivers 28. Alternatively, the cart may be positioned around the patient's upper abdomen in order to reach alternative vascular access points, such as, for example, the carotid and brachial arteries near the shoulder and wrist.

B. Robotic System—Table.

Figure 5:
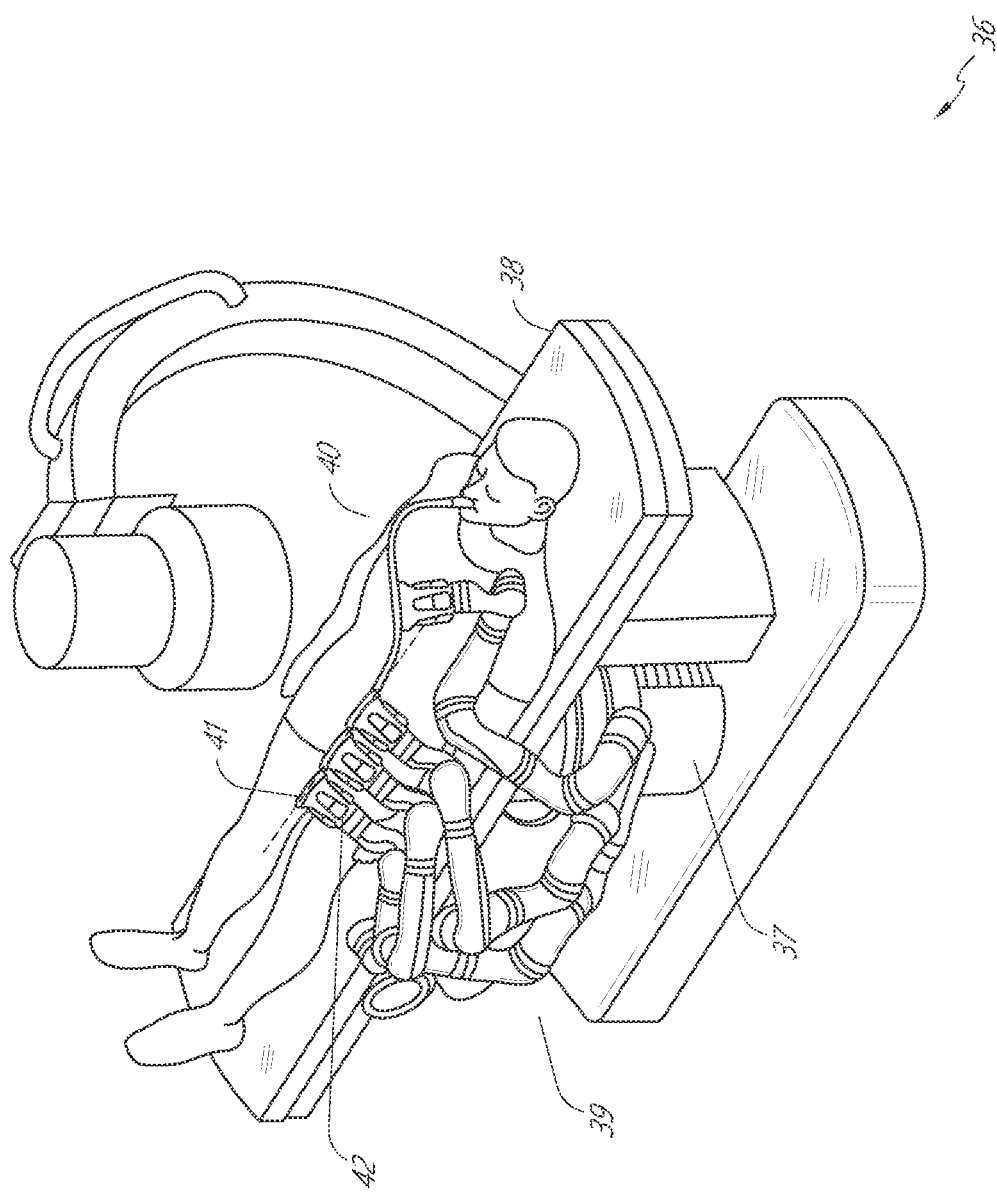
FIG. 5 illustrates an embodiment of a table-based robotic system arranged for a bronchoscopic procedure, according to an example embodiment.

Embodiments of the robotically-enabled medical system may also incorporate the patient's table. Incorporation of the table reduces the amount of capital equipment within the operating room by removing the cart, which allows greater access to the patient. FIG. 5 illustrates an embodiment of such a robotically-enabled system arranged for a bronchoscopic procedure. System 36 includes a support structure or column 37 for supporting platform 38 (shown as a "table" or "bed") over the floor. Much like in the cart-based systems, the end effectors of the robotic arms 39 of the system 36 comprise instrument drivers 42 that are designed to manipulate an elongated medical instrument, such as a bronchoscope 40 in FIG. 5, through or along a virtual rail 41 formed from the linear alignment of the instrument drivers 42. In practice, a C-arm for providing fluoroscopic imaging may be positioned over the patient's upper abdominal area by placing the emitter and detector around the table 38.

Figure 6:
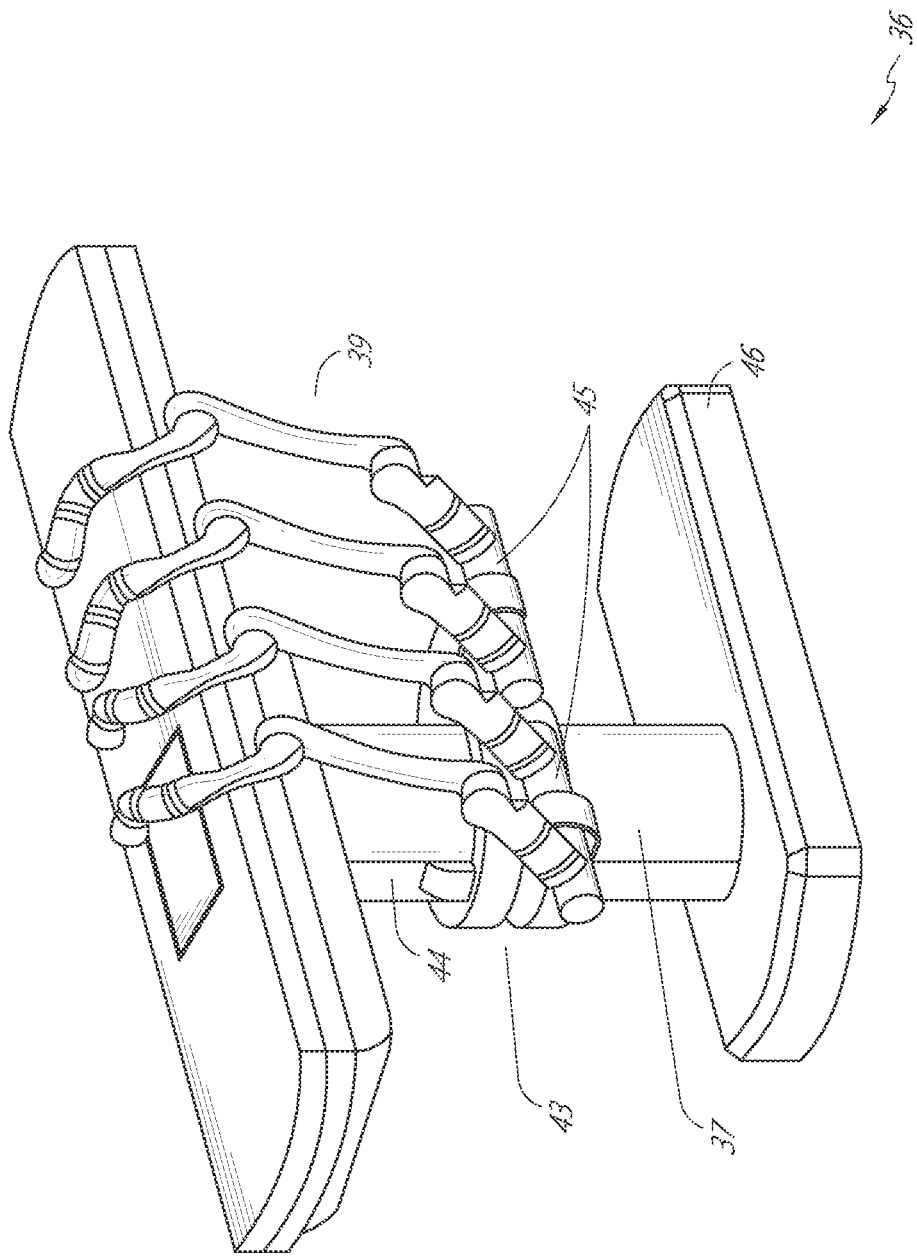
FIG. 6 provides an alternative view of the robotic system of FIG. 5, according to an example embodiment.

FIG. 6 provides an alternative view of the system 36 without the patient and medical instrument for discussion purposes. As shown, the column 37 may include one or more carriages 43 shown as ring-shaped in the system 36, from which the one or more robotic arms 39 may be based. The carriages 43 may translate along a vertical column interface 44 that runs the length of the column 37 to provide different vantage points from which the robotic arms 39 may be positioned to reach the patient. The carriage(s) 43 may rotate around the column 37 using a mechanical motor positioned within the column 37 to allow the robotic arms 39 to have access to multiples sides of the table 38, such as, for example, both sides of the patient. In embodiments with multiple carriages, the carriages may be individually positioned on the column and may translate and/or rotate independently of the other carriages. While the carriages 43 need not surround the column 37 or even be circular, the ring-shape as shown facilitates rotation of the carriages 43 around the column 37 while maintaining structural balance. Rotation and translation of the carriages 43 allows the system 36 to align the medical instruments, such as endoscopes and laparoscopes, into different access points on the patient. In other embodiments (not shown), the system 36 can include a patient table or bed with adjustable arm supports in the form of bars or rails extending alongside it. One or more robotic arms 39 (e.g., via a shoulder with an elbow joint) can be attached to the adjustable arm supports, which can be vertically adjusted. By providing vertical adjustment, the robotic arms 39 are advantageously capable of being stowed compactly beneath the patient table or bed, and subsequently raised during a procedure.

Figure 9:
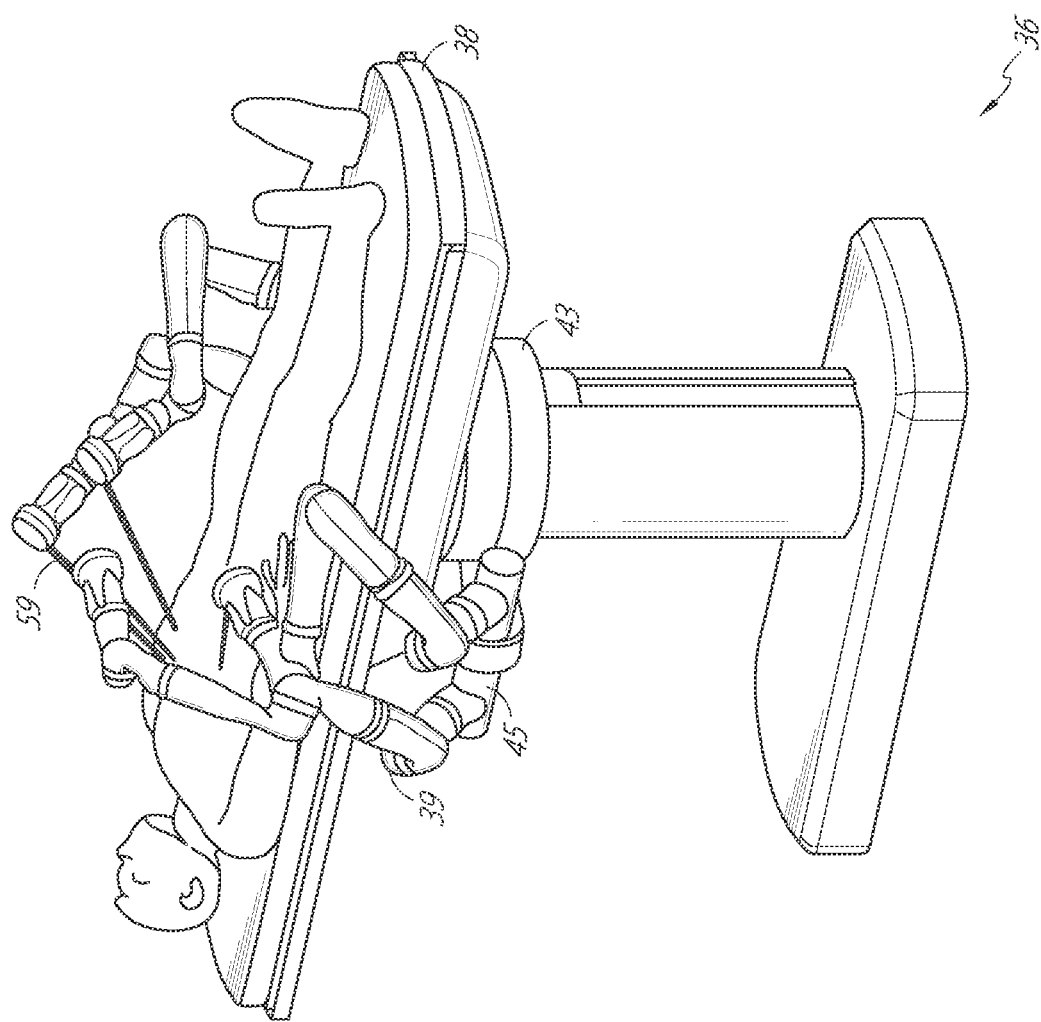
FIG. 9 illustrates an embodiment of a table-based robotic system configured for a laparoscopic procedure, according to an example embodiment.

The robotic arms 39 may be mounted on the carriages 43 through a set of arm mounts 45 comprising a series of joints that may individually rotate and/or telescopically extend to provide additional configurability to the robotic arms 39. Additionally, the arm mounts 45 may be positioned on the carriages 43 such that, when the carriages 43 are appropriately rotated, the arm mounts 45 may be positioned on either the same side of the table 38 (as shown in FIG. 6), on opposite sides of the table 38 (as shown in FIG. 9), or on adjacent sides of the table 38 (not shown).

The column 37 structurally provides support for the table 38, and a path for vertical translation of the carriages 43. Internally, the column 37 may be equipped with lead screws for guiding vertical translation of the carriages, and motors to mechanize the translation of the carriages 43 based the lead screws. The column 37 may also convey power and control signals to the carriages 43 and the robotic arms 39 mounted thereon.

The table base 46 serves a similar function as the cart base 15 in the cart 11 shown in FIG. 2, housing heavier components to balance the table/bed 38, the column 37, the carriages 43, and the robotic arms 39. The table base 46 may also incorporate rigid casters to provide stability during procedures. Deployed from the bottom of the table base 46, the casters may extend in opposite directions on both sides of the base 46 and retract when the system 36 needs to be moved.

With continued reference to FIG. 6, the system 36 may also include a tower (not shown) that divides the functionality of the system 36 between the table and the tower to reduce the form factor and bulk of the table. As in earlier disclosed embodiments, the tower may provide a variety of support functionalities to the table, such as processing, computing, and control capabilities, power, fluidics, and/or optical and sensor processing. The tower may also be movable to be positioned away from the patient to improve physician access and de-clutter the operating room. Additionally, placing components in the tower allows for more storage space in the table base 46 for potential stowage of the robotic arms 39. The tower may also include a master controller or console that provides both a user interface for user input, such as keyboard and/or pendant, as well as a display screen (or touchscreen) for preoperative and intraoperative information, such as real-time imaging, navigation, and tracking information. In some embodiments, the tower may also contain holders for gas tanks to be used for insufflation.

Figure 7:
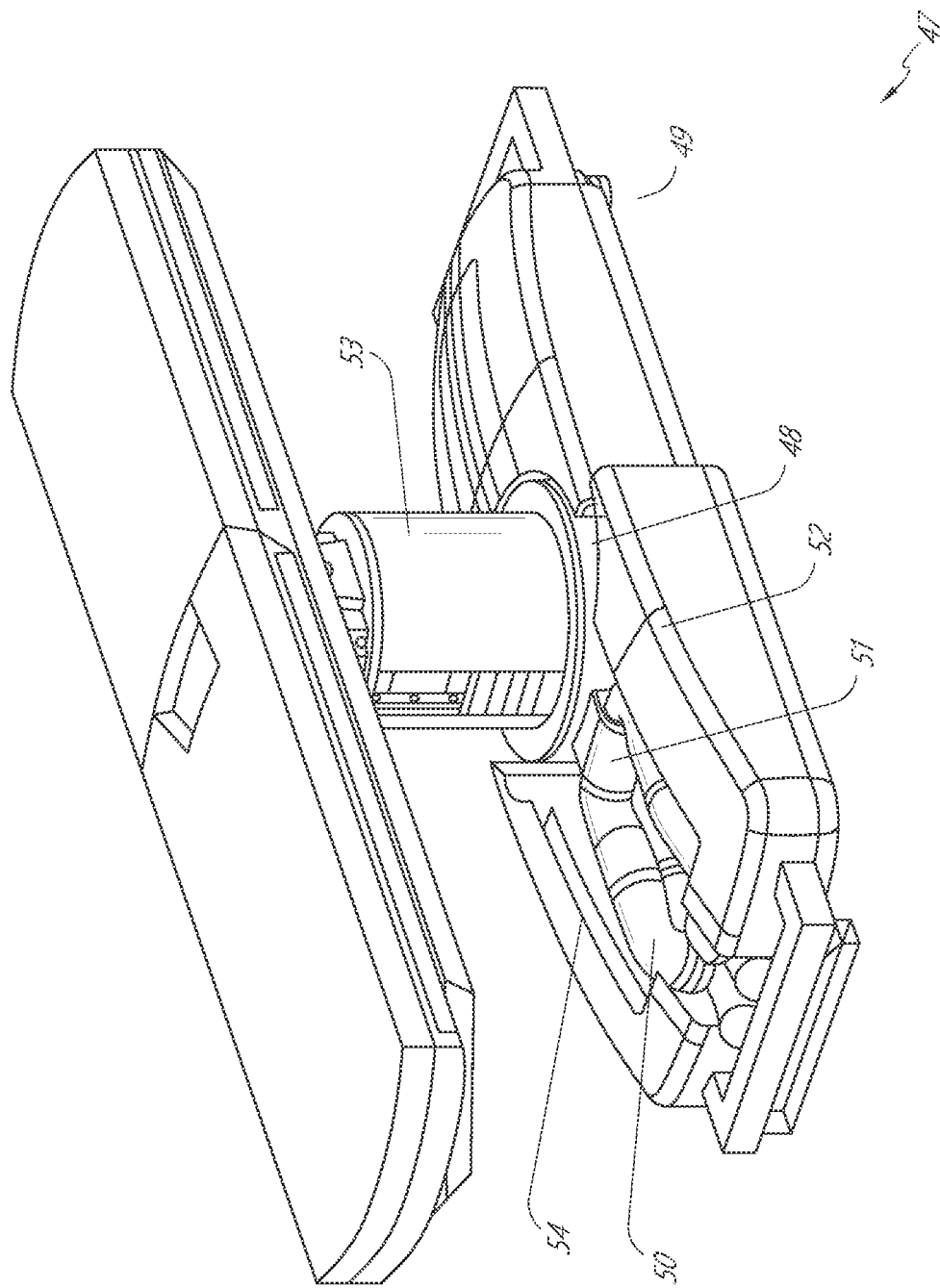
FIG. 7 illustrates an example system configured to stow robotic arm(s), according to an example embodiment, according to an example embodiment.

In some embodiments, a table base may stow and store the robotic arms when not in use. FIG. 7 illustrates a system 47 that stows robotic arms in an embodiment of the table-based system. In the system 47, carriages 48 may be vertically translated into base 49 to stow robotic arms 50, arm mounts 51, and the carriages 48 within the base 49. Base covers 52 may be translated and retracted open to deploy the carriages 48, arm mounts 51, and robotic arms 50 around column 53, and closed to stow to protect them when not in use. The base covers 52 may be sealed with a membrane 54 along the edges of its opening to prevent dirt and fluid ingress when closed.

Figure 8:
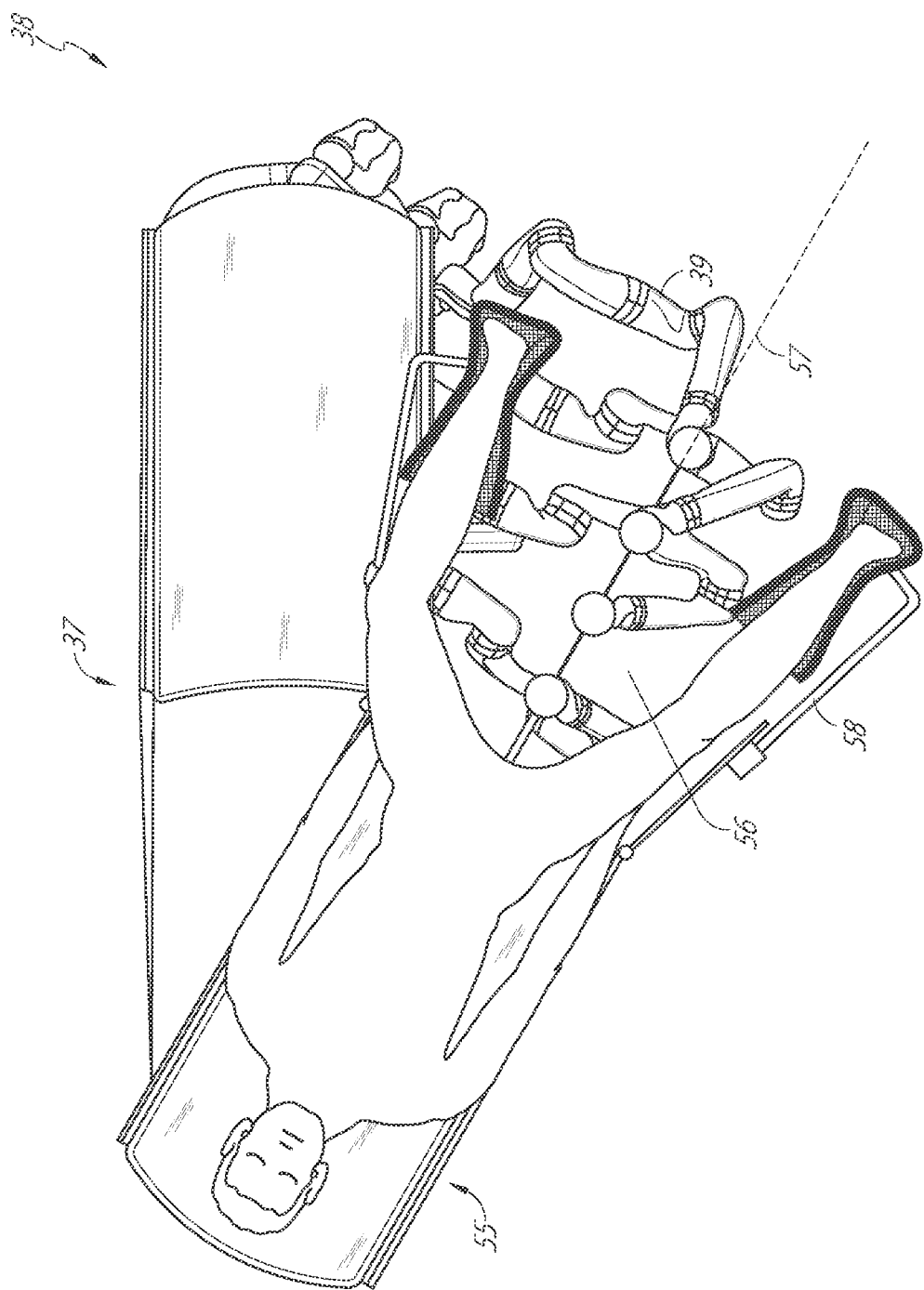
FIG. 8 illustrates an embodiment of a table-based robotic system configured for a ureteroscopic procedure, according to an example embodiment.

FIG. 8 illustrates an embodiment of a robotically-enabled table-based system configured for a ureteroscopic procedure. In a ureteroscopy, the table 38 may include a swivel portion 55 for positioning a patient off-angle from the column 37 and table base 46. The swivel portion 55 may rotate or pivot around a pivot point (e.g., located below the patient's head) in order to position the bottom portion of the swivel portion 55 away from the column 37. For example, the pivoting of the swivel portion 55 allows a C-arm (not shown) to be positioned over the patient's lower abdomen without competing for space with the column (not shown) below table 38. By rotating the carriage (not shown) around the column 37, the robotic arms 39 may directly insert a ureteroscope 56 along a virtual rail 57 into the patient's groin area to reach the urethra. In a ureteroscopy, stirrups 58 may also be fixed to the swivel portion 55 of the table 38 to support the position of the patient's legs during the procedure and allow clear access to the patient's groin area.

In a laparoscopic procedure, through small incision(s) in the patient's abdominal wall, minimally invasive instruments may be inserted into the patient's anatomy. In some embodiments, the minimally invasive instruments comprise an elongated rigid member, such as a shaft, which is used to access anatomy within the patient. After inflation of the patient's abdominal cavity, the instruments may be directed to perform surgical or medical tasks, such as grasping, cutting, ablating, suturing, etc. In some embodiments, the instruments can comprise a scope, such as a laparoscope. FIG. 9 illustrates an embodiment of a robotically-enabled table-based system configured for a laparoscopic procedure. As shown in FIG. 9, the carriages 43 of the system 36 may be rotated and vertically adjusted to position pairs of the robotic arms 39 on opposite sides of the table 38, such that instrument 59 may be positioned using the arm mounts 45 to be passed through minimal incisions on both sides of the patient to reach his/her abdominal cavity.

Figure 10:
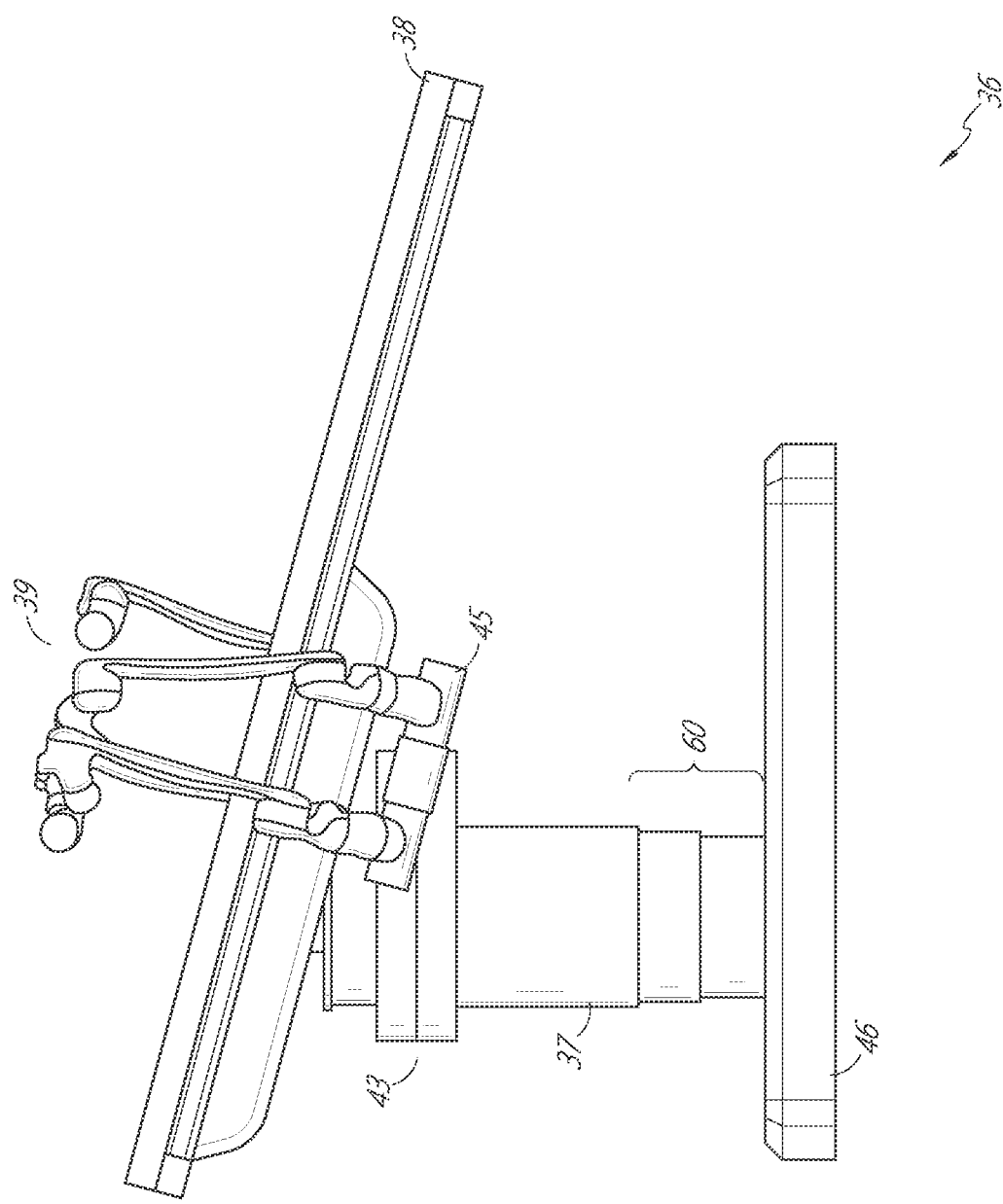
FIG. 10 illustrates an embodiment of the table-based robotic system of FIGS. 5-9 with pitch or tilt adjustment, according to an example embodiment.

To accommodate laparoscopic procedures, the robotically-enabled table system may also tilt the platform to a desired angle. FIG. 10 illustrates an embodiment of the robotically-enabled medical system with pitch or tilt adjustment. As shown in FIG. 10, the system 36 may accommodate tilt of the table 38 to position one portion of the table at a greater distance from the floor than the other. Additionally, the arm mounts 45 may rotate to match the tilt such that the robotic arms 39 maintain the same planar relationship with the table 38. To accommodate steeper angles, the column 37 may also include telescoping portions 60 that allow vertical extension of the column 37 to keep the table 38 from touching the floor or colliding with the table base 46.

Figure 11:
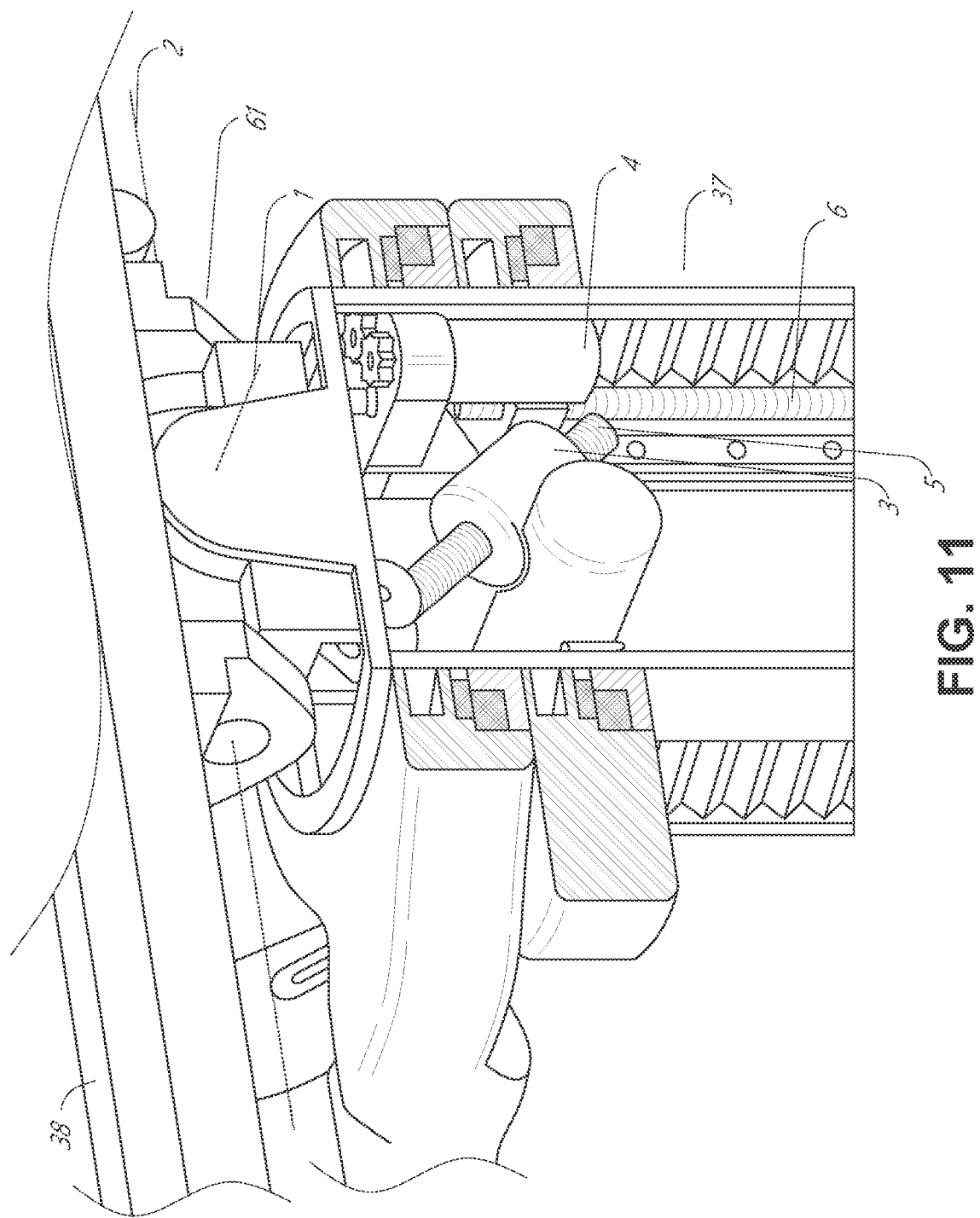
FIG. 11 provides a detailed illustration of the interface between the table and the column of the table-based robotic system of FIGS. 5-10, according to an example embodiment.

FIG. 11 provides a detailed illustration of the interface between the table 38 and the column 37. Pitch rotation mechanism 61 may be configured to alter the pitch angle of the table 38 relative to the column 37 in multiple degrees of freedom. The pitch rotation mechanism 61 may be enabled by the positioning of orthogonal axes 1, 2 at the column-table interface, each axis actuated by a separate motor 3, 4 responsive to an electrical pitch angle command. Rotation along one screw 5 would enable tilt adjustments in one axis 1, while rotation along the other screw 6 would enable tilt adjustments along the other axis 2. In some embodiments, a ball joint can be used to alter the pitch angle of the table 38 relative to the column 37 in multiple degrees of freedom.

For example, pitch adjustments are particularly useful when trying to position the table in a Trendelenburg position, i.e., position the patient's lower abdomen at a higher position from the floor than the patient's upper abdomen, for lower abdominal surgery. The Trendelenburg position causes the patient's internal organs to slide towards his/her upper abdomen through the force of gravity, clearing out the abdominal cavity for minimally invasive tools to enter and perform lower abdominal surgical or medical procedures, such as laparoscopic prostatectomy.

Figure 12:
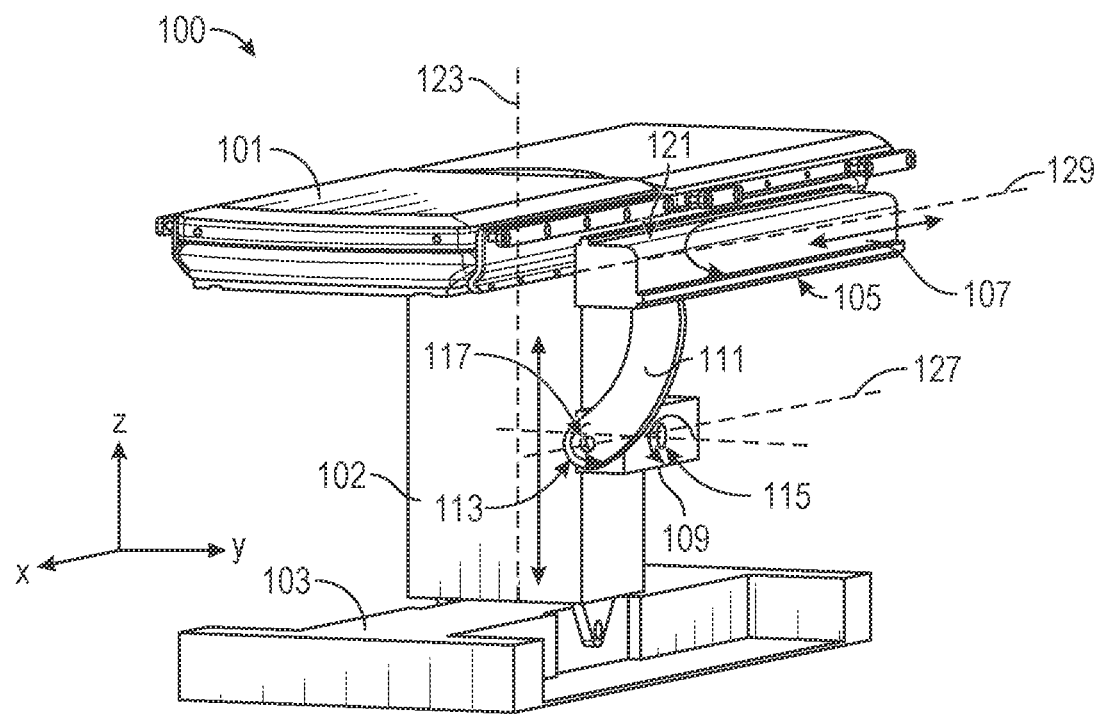
FIG. 12 illustrates an alternative embodiment of a table-based robotic system, according to an example embodiment.
Figure 13:
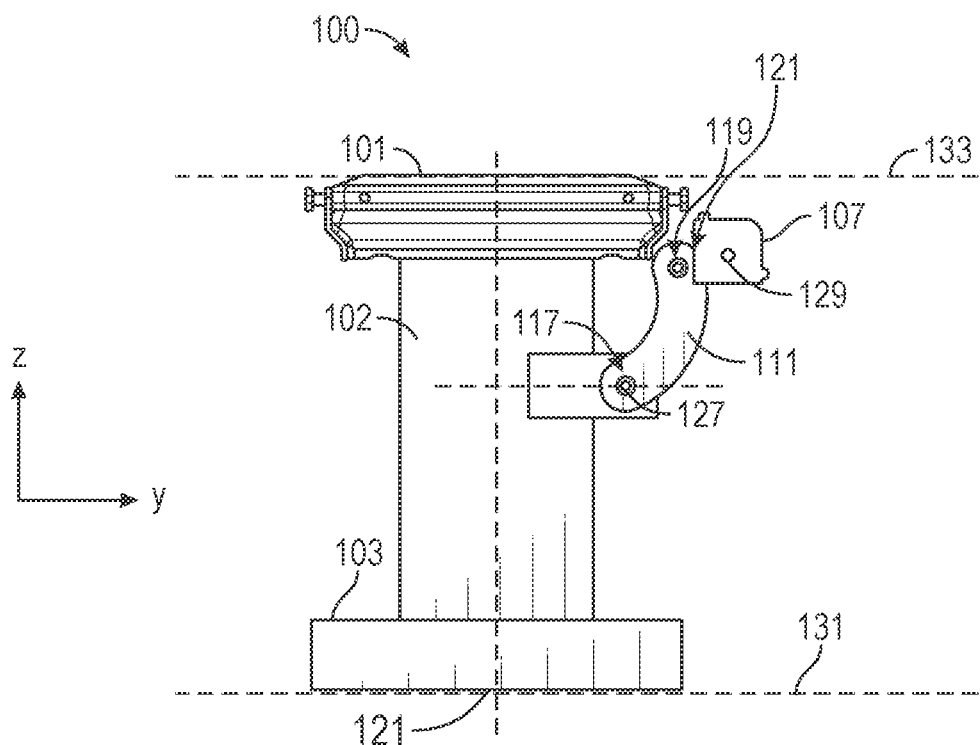
FIG. 13 illustrates an end view of the table-based robotic system of FIG. 12, according to an example embodiment.

FIGS. 12 and 13 illustrate isometric and end views of an alternative embodiment of a table-based surgical robotics system 100. The surgical robotics system 100 includes one or more adjustable arm supports 105 that can be configured to support one or more robotic arms (see, for example, FIG. 14) relative to a table 101. In the illustrated embodiment, a single adjustable arm support 105 is shown, though an additional arm support 105 can be provided on an opposite side of the table 101. The adjustable arm support 105 can be configured so that it can move relative to the table 101 to adjust and/or vary the position of the adjustable arm support 105 and/or any robotic arms mounted thereto relative to the table 101. For example, the adjustable arm support 105 may be adjusted one or more degrees of freedom relative to the table 101. The adjustable arm support 105 provides high versatility to the system 100, including the ability to easily stow the one or more adjustable arm supports 105 and any robotics arms attached thereto beneath the table 101. The adjustable arm support 105 can be elevated from the stowed position to a position below an upper surface of the table 101. In other embodiments, the adjustable arm support 105 can be elevated from the stowed position to a position above an upper surface of the table 101.

The adjustable arm support 105 can provide several degrees of freedom, including lift, lateral translation, tilt, etc. In the illustrated embodiment of FIGS. 12 and 13, the arm support 105 is configured with four degrees of freedom, which are illustrated with arrows in FIG. 12. A first degree of freedom allows for adjustment of the adjustable arm support 105 in the z-direction ("Z-lift"). For example, the adjustable arm support 105 can include a carriage 109 configured to move up or down along or relative to a column 102 supporting the table 101. A second degree of freedom can allow the adjustable arm support 105 to tilt. For example, the adjustable arm support 105 can include a rotary joint, which can allow the adjustable arm support 105 to be aligned with the bed in a Trendelenburg position. A third degree of freedom can allow the adjustable arm support 105 to "pivot up," which can be used to adjust a distance between a side of the table 101 and the adjustable arm support 105.

A fourth degree of freedom can permit translation of the adjustable arm support 105 along a longitudinal length of the table.

The surgical robotics system 100 in FIGS. 12 and 13 can comprise a table supported by a column 102 that is mounted to a base 103. The base 103 and the column 102 support the table 101 relative to a support surface. A floor axis 131 and a support axis 133 are shown in FIG. 13.

The adjustable arm support 105 can be mounted to the column 102. In other embodiments, the arm support 105 can be mounted to the table 101 or base 103. The adjustable arm support 105 can include a carriage 109, a bar or rail connector 111 and a bar or rail 107. In some embodiments, one or more robotic arms mounted to the rail 107 can translate and move relative to one another.

The carriage 109 can be attached to the column 102 by a first joint 113, which allows the carriage 109 to move relative to the column 102 (e.g., such as up and down a first or vertical axis 123). The first joint 113 can provide the first degree of freedom (Z-lift) to the adjustable arm support 105. The adjustable arm support 105 can include a second joint 115, which provides the second degree of freedom (tilt) for the adjustable arm support 105. The adjustable arm support 105 can include a third joint 117, which can provide the third degree of freedom ("pivot up") for the adjustable arm support 105. An additional joint 119 (shown in FIG. 13) can be provided that mechanically constrains the third joint 117 to maintain an orientation of the rail 107 as the rail connector 111 is rotated about a third axis 127. The adjustable arm support 105 can include a fourth joint 121, which can provide a fourth degree of freedom (translation) for the adjustable arm support 105 along a fourth axis 129.

Figure 14:
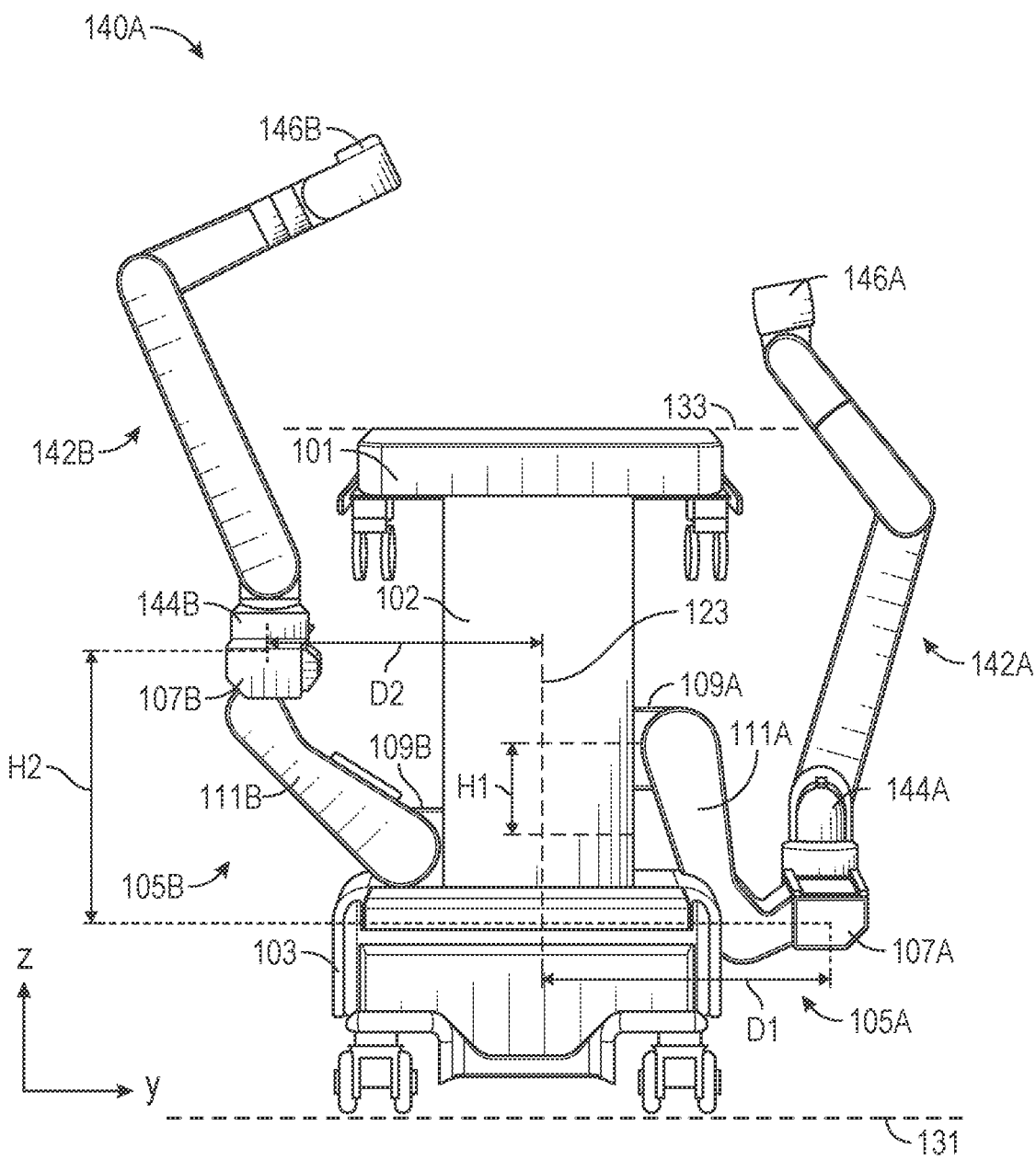
FIG. 14 illustrates an end view of a table-based robotic system with robotic arms attached thereto, according to an example embodiment.

FIG. 14 illustrates an end view of the surgical robotics system 140A with two adjustable arm supports 105A, 105B mounted on opposite sides of a table 101. A first robotic arm 142A is attached to the bar or rail 107A of the first adjustable arm support 105B. The first robotic arm 142A includes a base 144A attached to the rail 107A. The distal end of the first robotic arm 142A includes an instrument drive mechanism 146A that can attach to one or more robotic medical instruments or tools. Similarly, the second robotic arm 142B includes a base 144B attached to the rail 107B. The distal end of the second robotic arm 142B includes an instrument drive mechanism 146B. The instrument drive mechanism 146B can be configured to attach to one or more robotic medical instruments or tools.

In some embodiments, one or more of the robotic arms 142A, 142B comprises an arm with seven or more degrees of freedom. In some embodiments, one or more of the robotic arms 142A, 142B can include eight degrees of freedom, including an insertion axis (1-degree of freedom including insertion), a wrist (3-degrees of freedom including wrist pitch, yaw and roll), an elbow (1-degree of freedom including elbow pitch), a shoulder (2-degrees of freedom including shoulder pitch and yaw), and base 144A, 144B (1-degree of freedom including translation). In some embodiments, the insertion degree of freedom can be provided by the robotic arm 142A, 142B, while in other embodiments, the instrument itself provides insertion via an instrument-based insertion architecture.

C. Instrument Driver & Interface.

The end effectors of the system's robotic arms may comprise (i) an instrument driver (alternatively referred to as "instrument drive mechanism" or "instrument device manipulator") that incorporates electro-mechanical means for actuating the medical instrument and (ii) a removable or detachable medical instrument, which may be devoid of any electro-mechanical components, such as motors. This dichotomy may be driven by the need to sterilize medical instruments used in medical procedures, and the inability to adequately sterilize expensive capital equipment due to their intricate mechanical assemblies and sensitive electronics. Accordingly, the medical instruments may be designed to be detached, removed, and interchanged from the instrument driver (and thus the system) for individual sterilization or disposal by the physician or the physician's staff. In contrast, the instrument drivers need not be changed or sterilized, and may be draped for protection.

Figure 15:
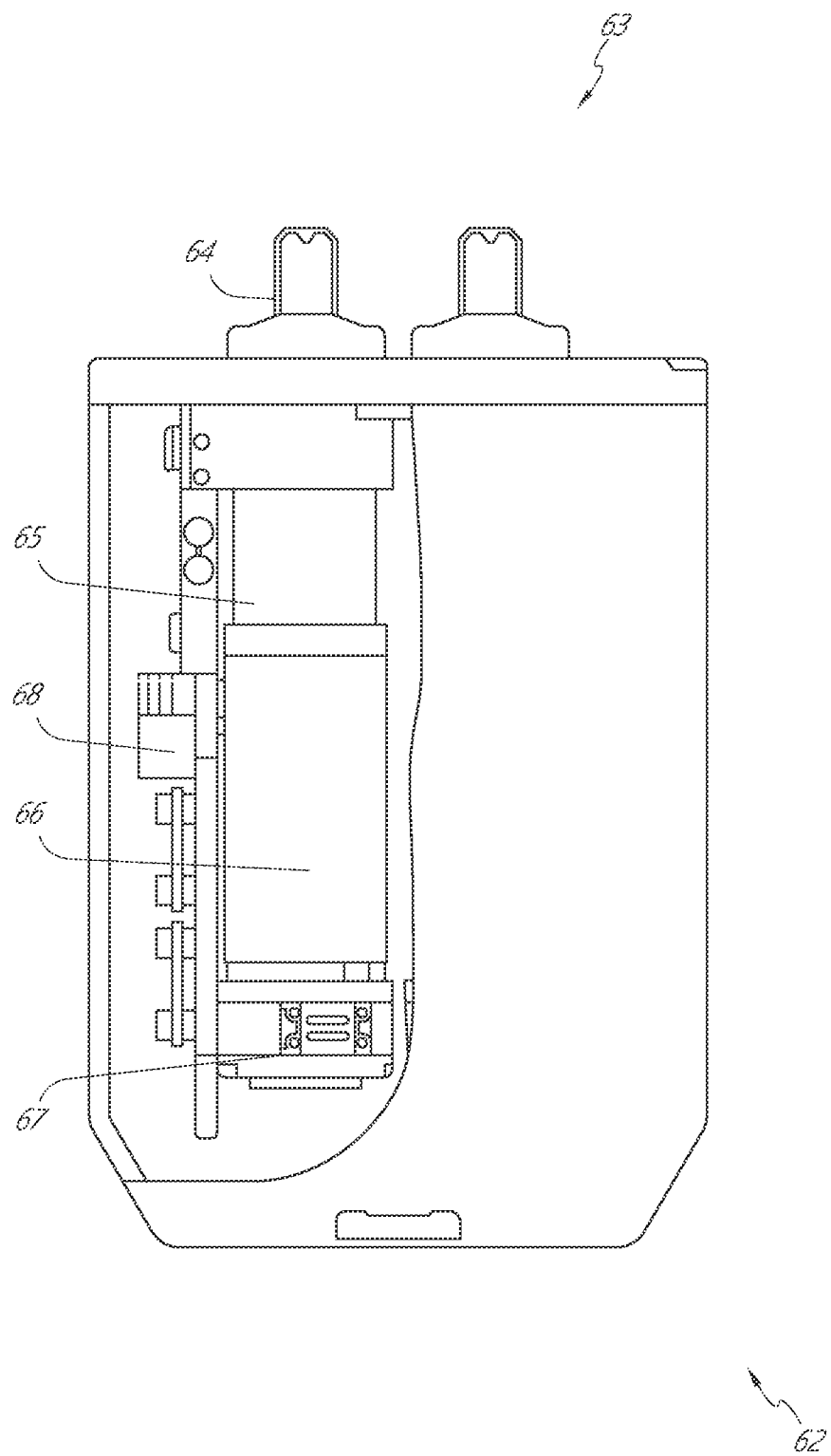
FIG. 15 illustrates an exemplary instrument driver, according to an example embodiment.

FIG. 15 illustrates an example instrument driver. Positioned at the distal end of a robotic arm, instrument driver 62 comprises one or more drive units 63 arranged with parallel axes to provide controlled torque to a medical instrument via drive shafts 64. Each drive unit 63 comprises an individual drive shaft 64 for interacting with the instrument, a gear head 65 for converting the motor shaft rotation to a desired torque, a motor 66 for generating the drive torque, an encoder 67 to measure the speed of the motor shaft and provide feedback to control circuitry, and control circuitry 68 for receiving control signals and actuating the drive unit. Each drive unit 63 being independently controlled and motorized, the instrument driver 62 may provide multiple (e.g., four as shown in FIG. 15) independent drive outputs to the medical instrument. In operation, the control circuitry 68 would receive a control signal, transmit a motor signal to the motor 66, compare the resulting motor speed as measured by the encoder 67 with the desired speed, and modulate the motor signal to generate the desired torque.

For procedures that require a sterile environment, the robotic system may incorporate a drive interface, such as a sterile adapter connected to a sterile drape, that sits between the instrument driver and the medical instrument. The chief purpose of the sterile adapter is to transfer angular motion from the drive shafts of the instrument driver to the drive inputs of the instrument while maintaining physical separation, and thus sterility, between the drive shafts and drive inputs. Accordingly, an example sterile adapter may comprise a series of rotational inputs and outputs intended to be mated with the drive shafts of the instrument driver and drive inputs on the instrument. Connected to the sterile adapter, the sterile drape, comprised of a thin, flexible material such as transparent or translucent plastic, is designed to cover the capital equipment, such as the instrument driver, robotic arm, and cart (in a cart-based system) or table (in a table-based system). Use of the drape would allow the capital equipment to be positioned proximate to the patient while still being located in an area not requiring sterilization (i.e., non-sterile field). On the other side of the sterile drape, the medical instrument may interface with the patient in an area requiring sterilization (i.e., sterile field).

D. Medical Instrument.

Figure 16:
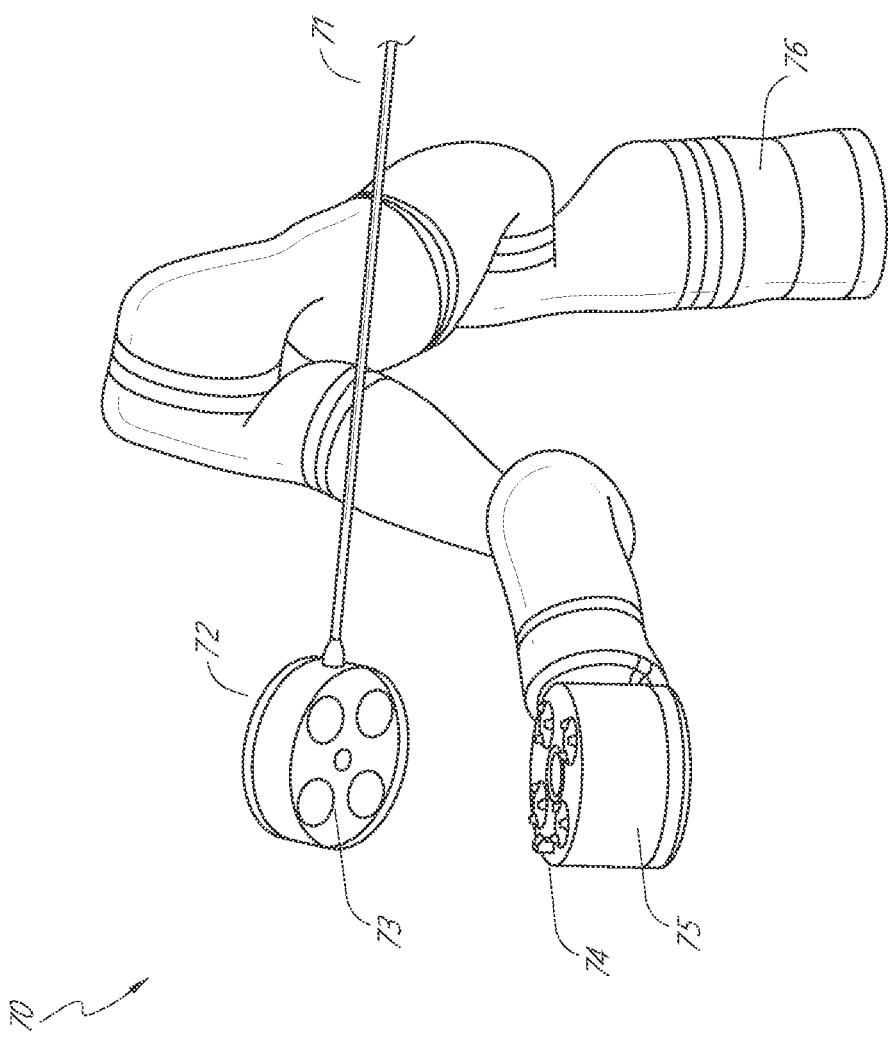
FIG. 16 illustrates an exemplary medical instrument with a paired instrument driver, according to an example embodiment.

FIG. 16 illustrates an example medical instrument with a paired instrument driver. Like other instruments designed for use with a robotic system, medical instrument 70 comprises an elongated shaft 71 (or elongate body) and an instrument base 72. The instrument base 72, also referred to as an "instrument handle" due to its intended design for manual interaction by the physician, may generally comprise rotatable drive inputs 73, e.g., receptacles, pulleys or spools, that are designed to be mated with drive outputs 74 that extend through a drive interface on instrument driver 75 at the distal end of robotic arm 76. When physically connected, latched, and/or coupled, the mated drive inputs 73 of the instrument base 72 may share axes of rotation with the drive outputs 74 in the instrument driver 75 to allow the transfer of torque from the drive outputs 74 to the drive inputs 73. In some embodiments, the drive outputs 74 may comprise splines that are designed to mate with receptacles on the drive inputs 73.

The elongated shaft 71 is designed to be delivered through either an anatomical opening or lumen, e.g., as in endoscopy, or a minimally invasive incision, e.g., as in laparoscopy. The elongated shaft 71 may be either flexible (e.g., having properties similar to an endoscope) or rigid (e.g., having properties similar to a laparoscope) or contain a customized combination of both flexible and rigid portions. When designed for laparoscopy, the distal end of a rigid elongated shaft may be connected to an end effector extending from a jointed wrist formed from a clevis with at least one degree of freedom and a surgical tool or medical instrument, such as, for example, a grasper or scissors, that may be actuated based on force from the tendons as the drive inputs rotate in response to torque received from the drive outputs 74 of the instrument driver 75. When designed for endoscopy, the distal end of a flexible elongated shaft may include a steerable or controllable bending section that may be articulated and bent based on torque received from the drive outputs 74 of the instrument driver 75.

Torque from the instrument driver 75 is transmitted down the elongated shaft 71 using tendons along the elongated shaft 71. These individual tendons, such as pull wires, may be individually anchored to individual drive inputs 73 within the instrument handle 72. From the instrument handle 72, the tendons are directed down one or more pull lumens along the elongated shaft 71 and anchored at the distal portion of the elongated shaft 71, or in the wrist at the distal portion of the elongated shaft. During a surgical procedure, such as a laparoscopic, endoscopic or hybrid procedure, these tendons may be coupled to a distally mounted end effector, such as a wrist, grasper, or scissor. Under such an arrangement, torque exerted on drive inputs 73 would transfer tension to the tendon, thereby causing the end effector to actuate in some way. In some embodiments, during a surgical procedure, the tendon may cause a joint to rotate about an axis, thereby causing the end effector to move in one direction or another. Alternatively, the tendon may be connected to one or more jaws of a grasper at the distal end of the elongated shaft 71, where tension from the tendon causes the grasper to close.

In endoscopy, the tendons may be coupled to a bending or articulating section positioned along the elongated shaft 71 (e.g., at the distal end) via adhesive, control ring, or other mechanical fixation. When fixedly attached to the distal end of a bending section, torque exerted on the drive inputs 73 would be transmitted down the tendons, causing the softer, bending section (sometimes referred to as the articulable section or region) to bend or articulate. Along the non-bending sections, it may be advantageous to spiral or helix the individual pull lumens that direct the individual tendons along (or inside) the walls of the endoscope shaft to balance the radial forces that result from tension in the pull wires. The angle of the spiraling and/or spacing therebetween may be altered or engineered for specific purposes, wherein tighter spiraling exhibits lesser shaft compression under load forces, while lower amounts of spiraling results in greater shaft compression under load forces, but limits bending. On the other end of the spectrum, the pull lumens may be directed parallel to the longitudinal axis of the elongated shaft 71 to allow for controlled articulation in the desired bending or articulable sections.

In endoscopy, the elongated shaft 71 houses a number of components to assist with the robotic procedure. The shaft 71 may comprise a working channel for deploying surgical tools (or medical instruments), irrigation, and/or aspiration to the operative region at the distal end of the shaft 71. The shaft 71 may also accommodate wires and/or optical fibers to transfer signals to/from an optical assembly at the distal tip, which may include an optical camera. The shaft 71 may also accommodate optical fibers to carry light from proximally-located light sources, such as light emitting diodes, to the distal end of the shaft 71.

At the distal end of the instrument 70, the distal tip may also comprise the opening of a working channel for delivering tools for diagnostic and/or therapy, irrigation, and aspiration to an operative site. The distal tip may also include a port for a camera, such as a fiberscope or a digital camera, to capture images of an internal anatomical space. Relatedly, the distal tip may also include ports for light sources for illuminating the anatomical space when using the camera.

In the example of FIG. 16, the drive shaft axes, and thus the drive input axes, are orthogonal to the axis of the elongated shaft 71. This arrangement, however, complicates roll capabilities for the elongated shaft 71. Rolling the elongated shaft 71 along its axis while keeping the drive inputs 73 static results in undesirable tangling of the tendons as they extend off the drive inputs 73 and enter pull lumens within the elongated shaft 71. The resulting entanglement of such tendons may disrupt any control algorithms intended to predict movement of the flexible elongated shaft 71 during an endoscopic procedure.

Figure 17:
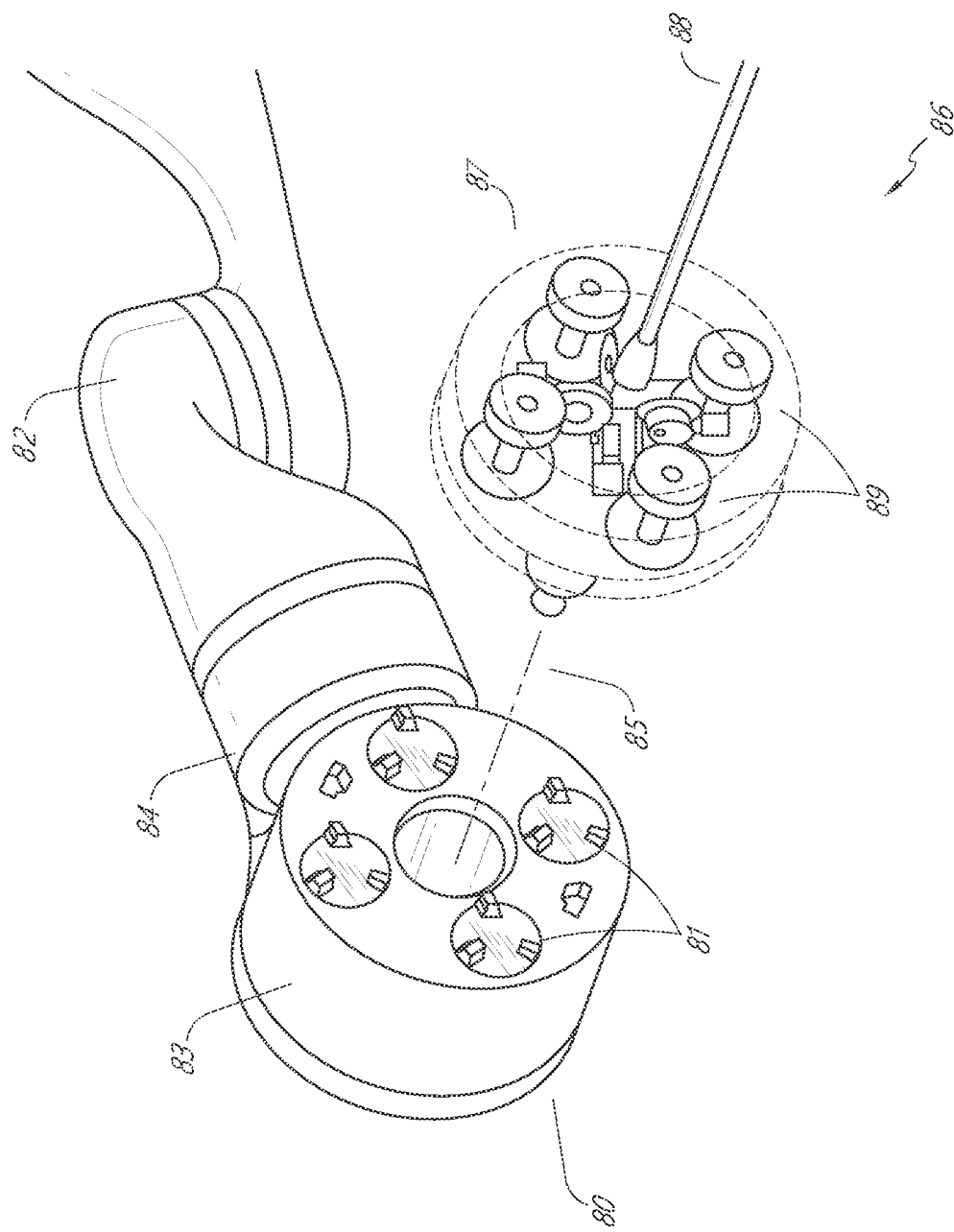
FIG. 17 illustrates an alternative design for an instrument driver and instrument where the axes of the drive units are parallel to the axis of the elongated shaft of the instrument, according to an example embodiment.

FIG. 17 illustrates an alternative design for an instrument driver and instrument where the axes of the drive units are parallel to the axis of the elongated shaft of the instrument. As shown, a circular instrument driver 80 comprises four drive units with their drive outputs 81 aligned in parallel at the end of a robotic arm 82. The drive units, and their respective drive outputs 81, are housed in a rotational assembly 83 of the instrument driver 80 that is driven by one of the drive units within the assembly 83. In response to torque provided by the rotational drive unit, the rotational assembly 83 rotates along a circular bearing that connects the rotational assembly 83 to the non-rotational portion 84 of the instrument driver 80. Power and controls signals may be communicated from the non-rotational portion 84 of the instrument driver 80 to the rotational assembly 83 through electrical contacts that may be maintained through rotation by a brushed slip ring connection (not shown). In other embodiments, the rotational assembly 83 may be responsive to a separate drive unit that is integrated into the non-rotatable portion 84, and thus not in parallel to the other drive units. The rotational mechanism 83 allows the instrument driver 80 to rotate the drive units, and their respective drive outputs 81, as a single unit around an instrument driver axis 85.

Like earlier disclosed embodiments, an instrument 86 may comprise an elongated shaft portion 88 and an instrument base 87 (shown with a transparent external skin for discussion purposes) comprising a plurality of drive inputs 89 (such as receptacles, pulleys, and spools) that are configured to receive the drive outputs 81 in the instrument driver 80. Unlike prior disclosed embodiments, the instrument shaft 88 extends from the center of the instrument base 87 with an axis substantially parallel to the axes of the drive inputs 89, rather than orthogonal as in the design of FIG. 16.

When coupled to the rotational assembly 83 of the instrument driver 80, the medical instrument 86, comprising instrument base 87 and instrument shaft 88, rotates in combination with the rotational assembly 83 about the instrument driver axis 85. Since the instrument shaft 88 is positioned at the center of instrument base 87, the instrument shaft 88 is coaxial with instrument driver axis 85 when attached. Thus, rotation of the rotational assembly 83 causes the instrument shaft 88 to rotate about its own longitudinal axis. Moreover, as the instrument base 87 rotates with the instrument shaft 88, any tendons connected to the drive inputs 89 in the instrument base 87 are not tangled during rotation. Accordingly, the parallelism of the axes of the drive outputs 81, drive inputs 89, and instrument shaft 88 allows for the shaft rotation without tangling any control tendons.

Figure 18:
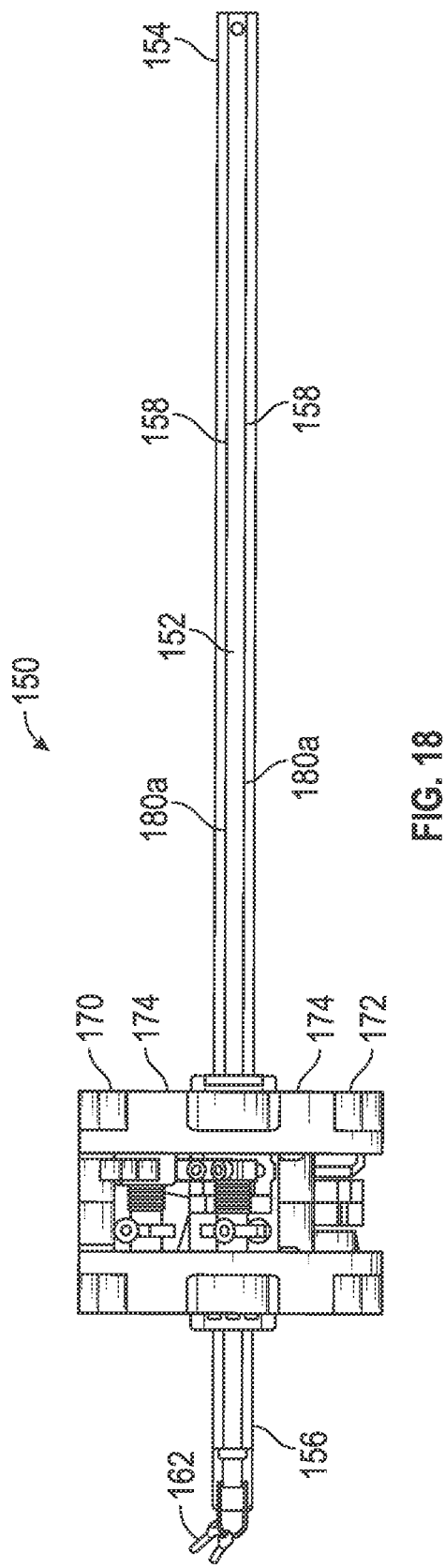
FIG. 18 illustrates an instrument having an instrument-based insertion architecture, according to an example embodiment.

FIG. 18 illustrates an instrument 150 having an instrument based insertion architecture in accordance with some embodiments. The instrument 150 can be coupled to any of the instrument drivers discussed above. The instrument 150 comprises an elongated shaft 152, an end effector 162 connected to the shaft 152, and a handle 170 coupled to the shaft 152. The elongated shaft 152 comprises a tubular member having a proximal portion 154 and a distal portion 156. The elongated shaft 152 comprises one or more channels or grooves 158 along its outer surface. The grooves 158 are configured to receive one or more wires or cables 180 therethrough. One or more cables 180 thus run along an outer surface of the elongated shaft 152. In other embodiments, cables 180 can also run through the elongated shaft 152. Manipulation of the one or more cables 180 (e.g., via an instrument driver) results in actuation of the end effector 162.

The instrument handle 170, which may also be referred to as an instrument base, may generally comprise an attachment interface 172 having one or more mechanical inputs 174, e.g., receptacles, pulleys or spools, that are designed to be reciprocally mated with one or more torque couplers on an attachment surface of an instrument driver.

In some embodiments, the instrument 150 comprises a series of pulleys or cables that enable the elongated shaft 152 to translate relative to the handle 170. In other words, the instrument 150 itself comprises an instrument-based insertion architecture that accommodates insertion of the instrument, thereby minimizing the reliance on a robot arm to provide insertion of the instrument 150. In other embodiments, a robotic arm can be largely responsible for instrument insertion.

E. Controller.

Any of the robotic systems described herein can include an input device or controller for manipulating an instrument attached to a robotic arm. In some embodiments, the controller can be coupled (e.g., communicatively, electronically, electrically, wirelessly and/or mechanically) with an instrument such that manipulation of the controller causes a corresponding manipulation of the instrument e.g., via master slave control.

Figure 19:
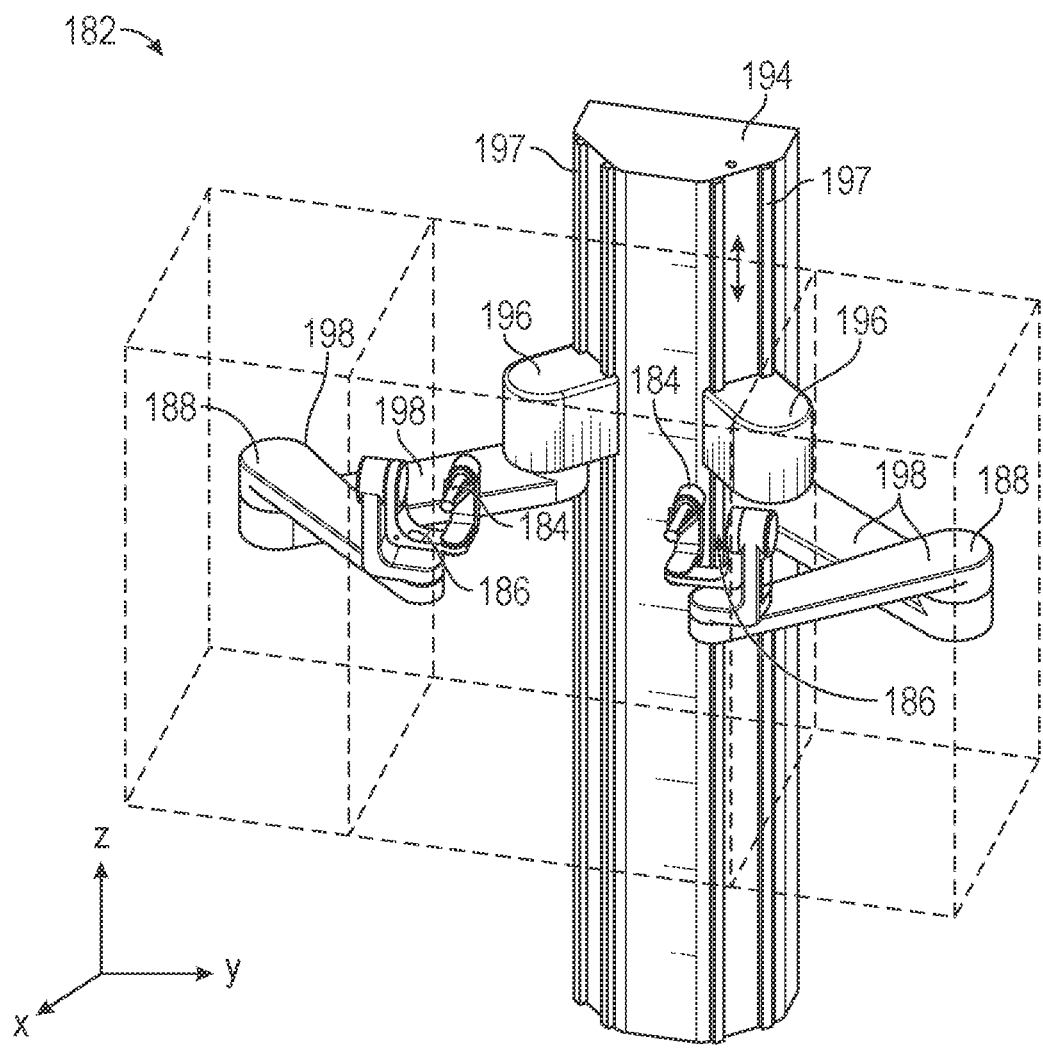
FIG. 19 illustrates an exemplary controller, according to an example embodiment.

FIG. 19 is a perspective view of an embodiment of a controller 182. In the present embodiment, the controller 182 comprises a hybrid controller that can have both impedance and admittance control. In other embodiments, the controller 182 can utilize just impedance or passive control. In other embodiments, the controller 182 can utilize just admittance control. By being a hybrid controller, the controller 182 advantageously can have a lower perceived inertia while in use.

In the illustrated embodiment, the controller 182 is configured to allow manipulation of two medical instruments, and includes two handles 184. Each of the handles 184 is connected to a gimbal 186. Each gimbal 186 is connected to a positioning platform 188.

As shown in FIG. 19, each positioning platform 188 includes a selective compliance assembly robot arm (SCARA) 198 coupled to a column 194 by a prismatic joint 196. The prismatic joints 196 are configured to translate along the column 194 (e.g., along rails 197) to allow each of the handles 184 to be translated in the z-direction, providing a first degree of freedom. The SCARA 198 is configured to allow motion of the handle 184 in an x-y plane, providing two additional degrees of freedom.

In some embodiments, one or more load cells are positioned in the controller. For example, in some embodiments, a load cell (not shown) is positioned in the body of each of the gimbals 186. By providing a load cell, portions of the controller 182 are capable of operating under admittance control, thereby advantageously reducing the perceived inertia of the controller while in use. In some embodiments, the positioning platform 188 is configured for admittance control, while the gimbal 186 is configured for impedance control. In other embodiments, the gimbal 186 is configured for admittance control, while the positioning platform 188 is configured for impedance control. Accordingly, for some embodiments, the translational or positional degrees of freedom of the positioning platform 188 can rely on admittance control, while the rotational degrees of freedom of the gimbal 186 rely on impedance control.

F. Navigation and Control.

Traditional endoscopy may involve the use of fluoroscopy (e.g., as may be delivered through a C-arm) and other forms of radiation-based imaging modalities to provide endoluminal guidance to an operator physician. In contrast, the robotic systems contemplated by this disclosure can provide for non-radiation-based navigational and localization means to reduce physician exposure to radiation and reduce the amount of equipment within the operating room. As used herein, the term "localization" may refer to determining and/or monitoring the position of objects in a reference coordinate system. Technologies such as preoperative mapping, computer vision, real-time EM tracking, and robot command data may be used individually or in combination to achieve a radiation-free operating environment. In other cases, where radiation-based imaging modalities are still used, the preoperative mapping, computer vision, real-time EM tracking, and robot command data may be used individually or in combination to improve upon the information obtained solely through radiation-based imaging modalities.

Figure 20:
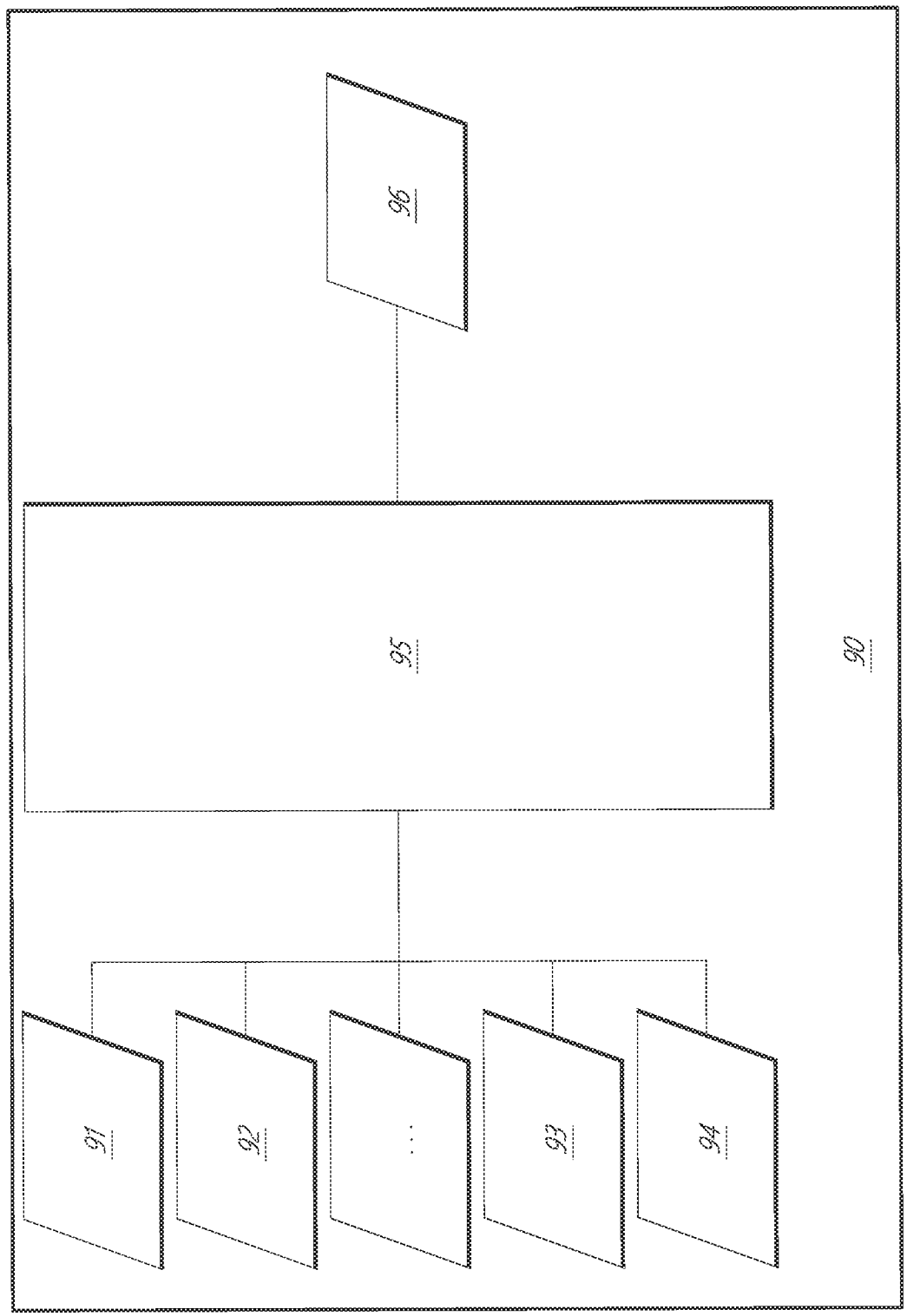
FIG. 20 depicts a block diagram illustrating a localization system that estimates a location of one or more elements of the robotic systems of FIGS. 1-10, such as the location of the instrument of FIGS. 16-18, in accordance to an example embodiment.

FIG. 20 is a block diagram illustrating a localization system 90 that estimates a location of one or more elements of the robotic system, such as the location of the instrument, in accordance to an example embodiment. The localization system 90 may be a set of one or more computer devices configured to execute one or more instructions. The computer devices may be embodied by a processor (or processors) and computer-readable memory in one or more components discussed above. By way of example and not limitation, the computer devices may be in the tower 30 shown in FIG. 1, the cart 11 shown in FIGS. 1-4, the beds shown in FIGS. 5-14, etc.

As shown in FIG. 20, the localization system 90 may include a localization module 95 that processes input data 91-94 to generate location data 96 for the distal tip of a medical instrument. The location data 96 may be data or logic that represents a location and/or orientation of the distal end of the instrument relative to a frame of reference. The frame of reference can be a frame of reference relative to the anatomy of the patient or to a known object, such as an EM field generator (see discussion below for the EM field generator).

The various input data 91-94 are now described in greater detail. Preoperative mapping may be used by the localization module 95 to generate model data 91. Preoperative mapping may be accomplished through the use of the collection of low dose CT scans. Preoperative CT scans are reconstructed into three-dimensional images, which are visualized, e.g. as "slices" of a cutaway view of the patient's internal anatomy. When analyzed in the aggregate, image-based models for anatomical cavities, spaces and structures of the patient's anatomy, such as a patient lung network, may be generated. Techniques such as center-line geometry may be determined and approximated from the CT images to develop a three-dimensional volume of the patient's anatomy, referred to as model data 91 (also referred to as "preoperative model data" when generated using only preoperative CT scans). The use of center-line geometry is discussed in U.S. patent application Ser. No. 14/523,760, the contents of which are herein incorporated in its entirety. Network topological models may also be derived from the CT-images, and are particularly appropriate for bronchoscopy.

In some embodiments, the instrument may be equipped with a camera to provide vision data (or image data) 92 to the localization module 95. The localization module 95 may process the vision data 92 to enable one or more vision-based (or image-based) location tracking modules or features. For example, the preoperative model data 91 may be used in conjunction with the vision data 92 to enable computer vision-based tracking of the medical instrument (e.g., an endoscope or an instrument advance through a working channel of the endoscope). For example, using the preoperative model data 91, the robotic system may generate a library of expected endoscopic images from the model based on the expected path of travel of the endoscope, each image linked to a location within the model. Intraoperatively, this library may be referenced by the robotic system in order to compare real-time images captured at the camera (e.g., a camera at a distal end of the endoscope) to those in the image library to assist localization.

Other computer vision-based tracking techniques use feature tracking to determine motion of the camera, and thus the endoscope. Some features of the localization module 95 may identify circular geometries in the preoperative model data 91 that correspond to anatomical lumens and track the change of those geometries to determine which anatomical lumen was selected, as well as the relative rotational and/or translational motion of the camera. Use of a topological map may further enhance vision-based algorithms or techniques.

Optical flow, another computer vision-based technique, may analyze the displacement and translation of image pixels in a video sequence in the vision data 92 to infer camera movement. Examples of optical flow techniques may include motion detection, object segmentation calculations, luminance, motion compensated encoding, stereo disparity measurement, etc. Through the comparison of multiple frames over multiple iterations, movement and location of the camera (and thus the endoscope) may be determined.

The localization module 95 may use real-time EM tracking and EM data 93 to generate a real-time location of the endoscope in a global coordinate system that may be registered to the patient's anatomy, represented by the preoperative model. In EM tracking, an EM sensor (or tracker) comprising one or more sensor coils embedded in one or more locations and orientations in a medical instrument (e.g., an endoscopic tool) measures the variation in the EM field created by one or more static EM field generators positioned at a known location. The location information detected by the EM sensors is stored as EM data 93. The EM field generator (or transmitter), may be placed close to the patient to create a low intensity magnetic field that the embedded sensor may detect. The magnetic field induces small currents in the sensor coils of the EM sensor, which may be analyzed to determine the distance and angle between the EM sensor and the EM field generator. These distances and orientations may be intraoperatively "registered" to the patient anatomy (e.g., the preoperative model) in order to determine the geometric transformation that aligns a single location in the coordinate system with a position in the preoperative model of the patient's anatomy. Once registered, an embedded EM tracker in one or more positions of the medical instrument (e.g., the distal tip of an endoscope) may provide real-time indications of the progression of the medical instrument through the patient's anatomy.

Robotic command and kinematics data 94 may also be used by the localization module 95 to provide location data 96 for the robotic system. Device pitch and yaw resulting from articulation commands may be determined during preoperative calibration. Intraoperatively, these calibration measurements may be used in combination with known insertion depth information to estimate the position of the instrument. Alternatively, these calculations may be analyzed in combination with EM, vision, and/or topological modeling to estimate the position of the medical instrument within the network.

As FIG. 20 shows, a number of other input data can be used by the localization module 95. For example, although not shown in FIG. 20, an instrument utilizing shape-sensing fiber can provide shape data that the localization module 95 can use to determine the location and shape of the instrument.

The localization module 95 may use the input data 91-94 in combination(s). In some cases, such a combination may use a probabilistic approach where the localization module 95 assigns a confidence weight to the location determined from each of the input data 91-94. Thus, where the EM data may not be reliable (as may be the case where there is EM interference) the confidence of the location determined by the EM data 93 can be decrease and the localization module 95 may rely more heavily on the vision data 92 and/or the robotic command and kinematics data 94.

As discussed above, the robotic systems discussed herein may be designed to incorporate a combination of one or more of the technologies above. The robotic system's computer-based control system, based in the tower, bed and/or cart, may store computer program instructions, for example, within a non-transitory computer-readable storage medium such as a persistent magnetic storage drive, solid state drive, or the like, that, upon execution, cause the system to receive and analyze sensor data and user commands, generate control signals throughout the system, and display the navigational and localization data, such as the position of the instrument within the global coordinate system, anatomical map, etc.

2. Robotically Controllable Field Generators

Embodiments of robotically controllable EM field generators that may be configured for use with robotic medical systems, such as those described above and others, are described herein. The robotically controllable EM field generators can be configured to couple to (or otherwise be attached to or integrated into) a robotic arm of a robotic medical system. Such robotically controllable EM field generators can provide advantages over other EM field generators that are commonly used with robotic medical systems, which usually require a more complex registration step to relate a coordinate frame of the EM field to a coordinate frame of the robotic system or a global coordinate frame and generally cannot be repositioned during a procedure without having to redo the complex registration step.

By coupling an EM field generator to a robotic arm, the kinematics of the robotic arm can be used to register the coordinate frame of the EM field to the robotic or global coordinate frame. Such registration based on the kinematics of the robotic arm can occur automatically or without requiring an operator to perform a separate registration step (such as those registration steps described below with reference to FIGS. 22B and 22C). This can eliminate the need for more complex or user involved registrations that are common with other types of EM field generators used with robotic medical systems. Further, with the EM field generator coupled to the robotic arm, the EM field generator becomes robotically controllable or positionable. The robotic arm can be commanded to translate, rotate, or a combination of both, to physically move the EM field generator to various positions during a robotic medical procedure.

As will be described in more detail below, such robotically controllable EM field generators can provide several advantages and are useful in a wide variety of applications. For example, use of such robotically controllable EM field generators can eliminate the need to perform a separate registration step to register the coordinate frame of the EM field with the robotic or global coordinate frame, provide a wider field of view through the ability to move the EM field generator with the robotic arm, permit the use of smaller EM field generators (e.g., compact field generators), simplify set up of the robotic medical system, and increase the accuracy of the detected position of EM sensors, among others. Applications for such robotically controllable EM field generators can include, for example, automatic tool tracking, automatic or enhanced field generator setup, EM focusing, anatomical mapping, and others.

These and other features of the robotically controllable field generators will be described in more detail below after first providing a brief overview of the use of EM sensors and EM Field generators generally in robotic medical systems.

A. Brief Overview of Use of EM Sensors and EM Field Generators

Robotic medical systems may use various types of position sensors to facilitate tracking and navigation of various tools and instruments. As described above, one type of position sensor that may be used in a robotic medical system is an EM position sensor (also referred to herein as an EM sensor, beacon, or tracker). One or more EM sensors can be provided, for example, on a portion of a tool or instrument used during a medical procedure. The position(s) of the EM sensor(s) can be determined and used to track the position(s) of the corresponding tool(s) or instruments. One or more EM sensors can also be provided on a patient, for example, to track patient movement (such as movement due to respiration or other types of movement) during a procedure. As noted above with respect to FIG. 20, a localization system 90 may use EM data 93, along with various other types of data, to provide navigation and guidance information to an operator of the system.

EM sensors are used with one or more EM field generators that are configured to generate a low intensity magnetic field. When an EM sensor is positioned within the magnetic field generated by EM field generator (also referred to as the working volume of the EM field generator), the position of the EM sensor relative to the EM field generator can be determined. For example, as described above with reference to FIG. 20, an EM sensor can comprise one or more sensor coils that measure the variation in the magnetic field generated by an EM field generator. The magnetic field can induce small currents in the sensor coils of the EM sensor that can be analyzed to determine, for example, the distance and angle between the EM sensor and the EM field generator.

In some embodiments, the position (e.g., the three-dimensional position) of the EM sensor relative to the EM field generator can be determined. In some embodiments, the orientation (e.g., the pitch, yaw, and/or roll) of the EM sensor can also be determined. A five degree of freedom (DoF) EM sensor can provide the three-dimensional position of the EM sensor as well as the pitch and yaw of the EM sensor. A six DoF EM sensor can provide the three-dimensional position of the EM sensor as well as the pitch, yaw, and roll of the EM sensor.

Figure 21:
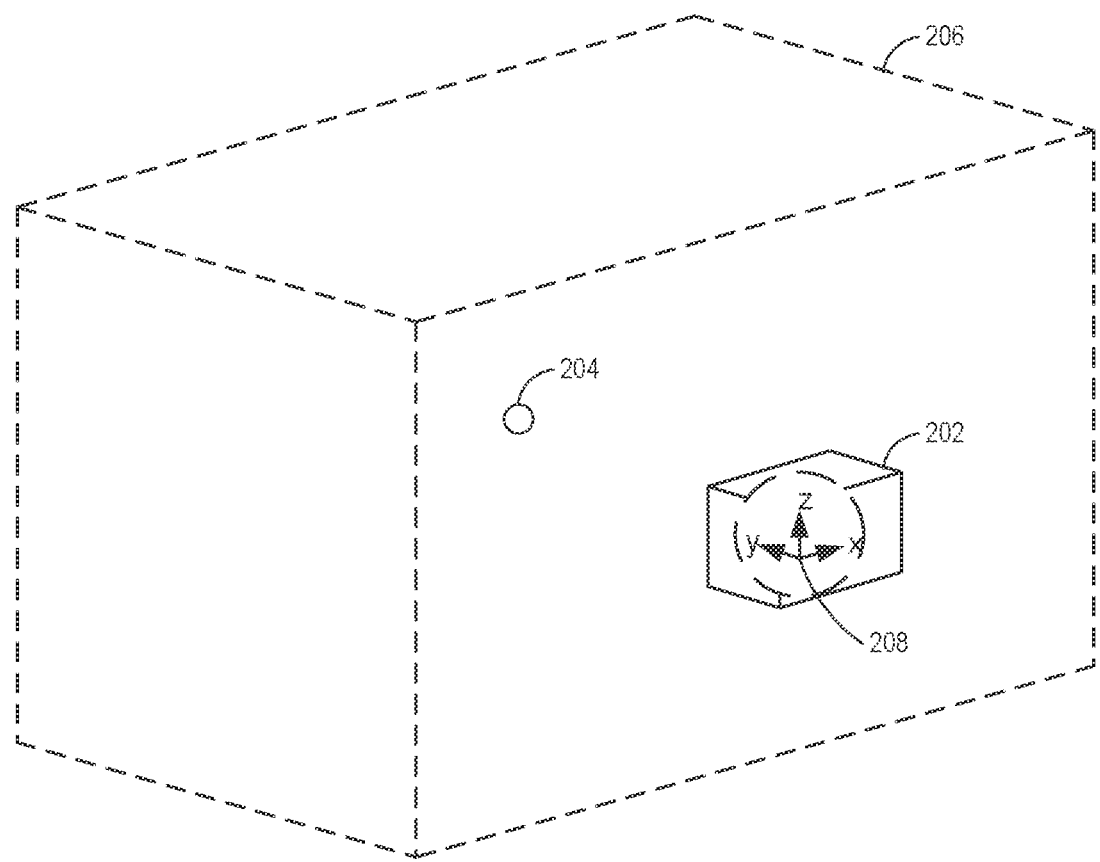
FIG. 21 illustrates an example EM field generator producing a magnetic field having a working volume. An example EM sensor, positioned within the working volume of the EM field generator is also shown, in accordance to an example embodiment.

FIG. 21 illustrates an example of an EM field generator 202 and an EM sensor 204. The EM field generator 202 is configured to produce a magnetic field. In the illustrated embodiment, the magnetic field of the EM field generator 202 has a working volume 206. When the EM sensor 204 is positioned within the working volume 206 of the magnetic field generated by the EM field generator 202 the position (or the position and orientation) of the EM sensor 204 can be determined relative to an EM coordinate frame 208 associated with the EM field generator 202. For example, the distance and angle between the EM sensor 204 and an origin of the EM coordinate frame 208 can be determined such that the position (e.g., the x, y, and z position) and/or the orientation (e.g., the pitch, yaw, and/or roll) of the EM sensor 204 within the working volume 206 can be determined.

In the illustrated embodiment, the working volume 206 of EM field generator 202 is represented as having the shape of a rectangular prism projecting from one side of the EM field generator 202. This, however, is merely representative of one type of working volume 206, and EM field generators 202 can be provided that produce working volumes 206 of various sizes, shapes, and positions relative the EM field generator 202.

Figure 22A:
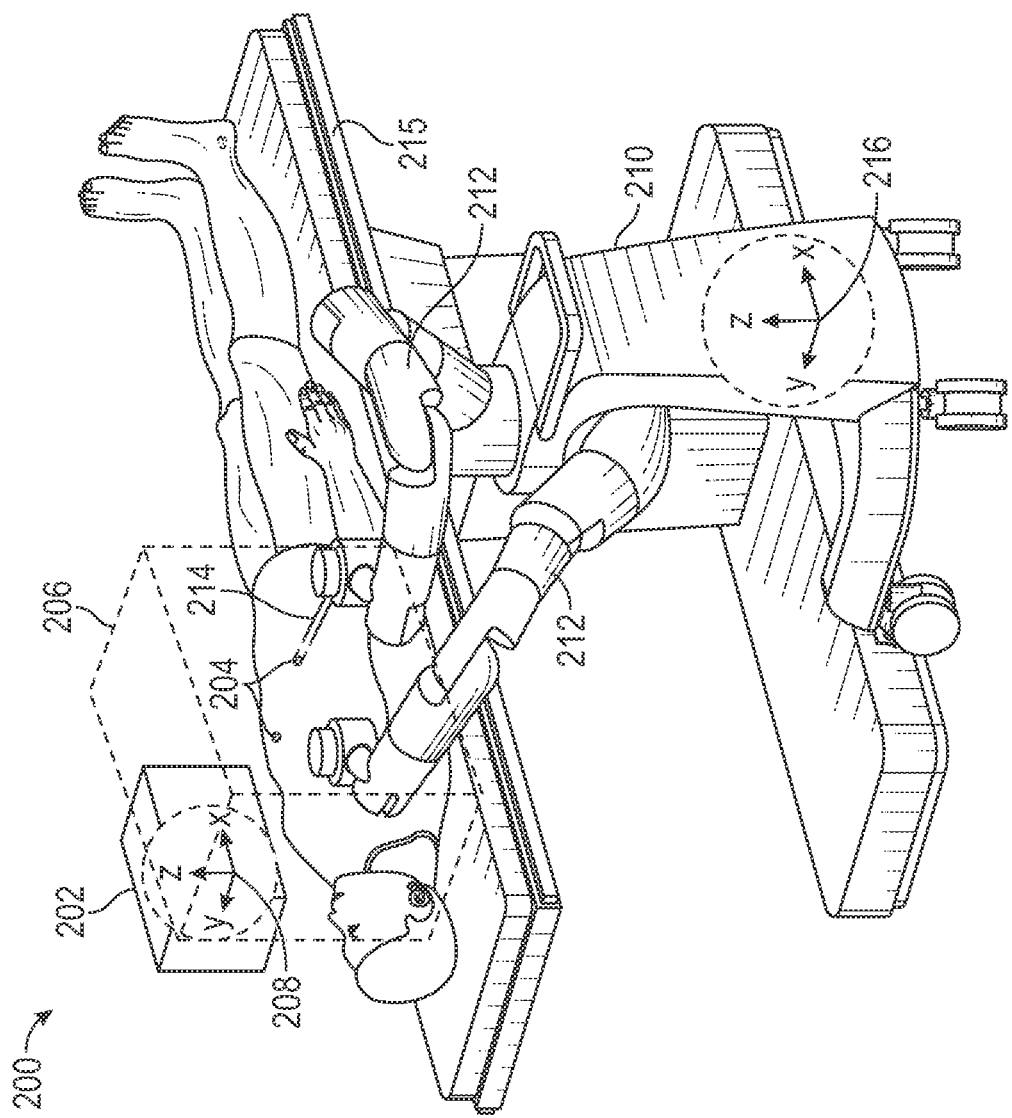
FIG. 22A is a perspective view illustrating an embodiment of a robotic medical system that includes the EM field generator of FIG. 21, according to an example embodiment.

FIG. 22A illustrates an example robotic medical system 200 that uses the EM field generator 202 of FIG. 21. The robotic medical system 200 may be similar to the robotic medical systems described above with reference to FIGS. 1-20. In the illustrated embodiment, the robotic medical system 200 comprises a cart 210 including two robotic arms 212. Although illustrated with two robotic arms 212, other numbers of robotic arms 212 are also possible. For example, FIG. 2 (described above) illustrates an example cart 11 that includes three robotic arms 12. Additionally, in some embodiments, the robotic arms 212 need not be attached to the cart 210. In some embodiments, the robotic arms can be coupled to the bed or patient platform 215, for example, as shown in FIGS. 5-10 and 14 (described above). In some embodiments, the robotic medical system 200 may comprise robotic arms 212 that are coupled to the cart 210, the patient platform, and/or other components of the system.

The robotic arms 212 can be associated with a robotic coordinate frame 216. Due to the known kinematics of the robotic arms 212, the position of the robotic arms 212 (e.g., the positions of the distal ends of the robotic arms 212 and/or the positions of an instrument 214 attached thereto) can be determined with reference to the robotic coordinate frame 216. For example, because the lengths of the various links that make up the robotic arms 212 are known and the angles of between the links of the robotic arms 212 can be determined, the positions of the robotic arms are kinematically defined within the robotic coordinate frame 216.

In some embodiments, the position and orientation of the cart 210 relative to the patient platform 215 and patient can be determined, set, or controlled such that the robotic coordinate frame 216 can be considered a global coordinate frame that can be registered to the patient or a portion of the patient's anatomy. For example, in some embodiments, up, down, right, left, etc., within the robotic coordinate frame 216 can correspond to up, down, right, left, etc., within the global coordinate frame that includes the patient, patient platform 215, and/or other components.

As shown in FIG. 22A, the tool or instrument 214 (e.g., a laparoscopic or endoscopic instrument) can be coupled to one of the robotic arms 212. The instrument 214 can be inserted into the patient to perform a medical procedure. Although only a single instrument 214 is illustrated, it should be appreciated that other numbers of instruments 214 (e.g., two or more instruments) can be used in other embodiments. One or more robotic arms 212 are useable to position and control the instrument(s) 214. An operator (not shown) can control the robotic arm(s) 212 and the instrument 214 using a controller.

In the illustrated embodiment, the instrument 214 includes the EM sensor 204 positioned at a distal end thereof. Further, the illustrated embodiment includes a second EM sensor 204 attached to the patient's chest, which can be used to track patient movement or motion, such as motion caused by the patient's respiration.

FIG. 22A illustrates that, in some embodiments, the EM field generator 202 can be positioned relative to the patient such that the working volume 206 of the field generator 202 overlaps with a portion of the patient's anatomy at which the medical procedure is performed. As used herein, a portion of the patient's anatomy at which a medical procedure is performed can be referred to as a medical site, and this site can include a site where any medical procedure can be performed, including biopsy, endoscopy, surgery, therapeutics, and the like. In some embodiments, the EM field generator 202 can be supported by a stand or other support structure (not shown) such that the working volume 206 is positioned relative to the patient. In other embodiments, the EM field generator 202 can be supported by or attached to the patient platform 215 or integrated into or supported by another component within the operating environment (such as the cart 30 described above with reference to FIGS. 1, 3, and 4).

As described above with reference to FIG. 21, when the EM sensors 204 are positioned within the working volume 206 of the EM field generator 202, the positions of the EM sensors 204 within the EM coordinate frame 208 can be determined. However, determining the positions of the EM sensors 204 within the EM coordinate frame 208 may not be particularly useful, unless the EM coordinate frame 208 has been registered to the robotic coordinate frame 216 or a global coordinate frame (which as noted above can be the robotic coordinate frame 216). Thus, a registration step, which relates the EM coordinate frame 208 to the robotic coordinate frame 216, is often required.

Figure 22B:
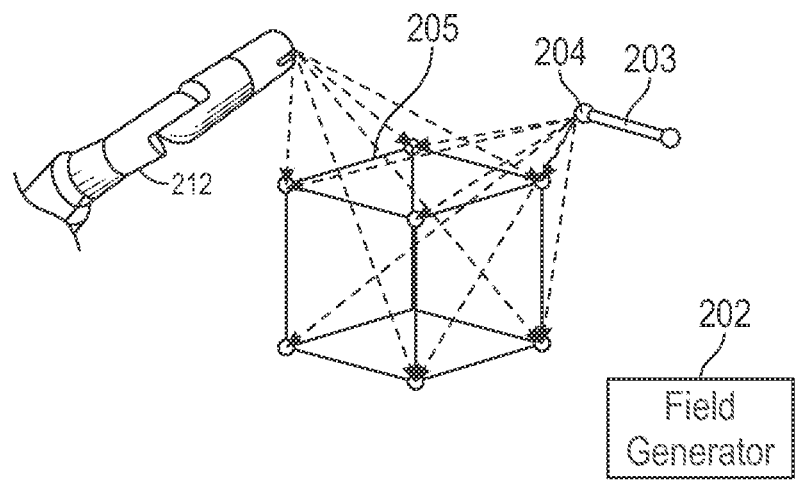
FIGS. 22B and 22C illustrate example registration steps that can be used to register a robotic coordinate frame associated with the robotic medical system of FIG. 22A with a EM coordinate system associated with the EM field generator, according to an example embodiment.
Figure 22C:
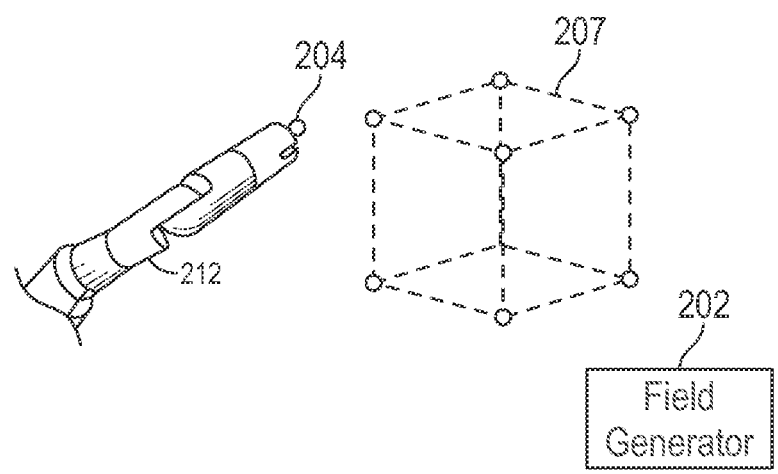

In some robotic medical systems, such as the illustrated robotic medical system 200 of FIG. 22A, registering the EM coordinate frame 208 to the robotic coordinate frame 216 can require the operator to perform certain steps to achieve the registration. The registration process can add steps to a procedure and can increase procedure times. FIGS. 22B and 22C illustrate example registration steps or procedure that can be used to register the robotic coordinate frame 216 associated with the robotic medical system 200 with the EM coordinate system 208 associated with the EM field generator 202. As will be described in more detail below, the need to perform these types of registration steps or procedures can be eliminated or reduced by providing a robotic medical system with an EM field generator that is attached to a robotic arm thereof, as shown, for example, in FIG. 23.

FIG. 22B illustrates an example registration procedure that can be used to register the robotic coordinate frame 216 associated with the robotic medical system 200 with the EM coordinate system 208 associated with the EM field generator 202. To achieve registration, a plurality of points are identified within both the robotic coordinate frame 216 and the EM coordinate frame 208. Once the plurality of points are identified within each of the robotic coordinate frame 216 and the EM coordinate frame 208, a registration algorithm can determine a transformation between the two coordinate frames. The registration procedure of FIG. 22B uses one of the robotic arms 212 of the robotic system, the EM field generator 202, an EM probe 203, and a registration fixture 205. In the illustrated embodiment, the registration fixture 205 comprises a cube having fiducials or markers located at the vertices of the cube. Accordingly, in the illustrated embodiment, the registration fixture 205 comprises eight fiducials. Other numbers of fiducials and other shapes for the registration fixture 205 may also be used. With the registration fixture 205 positioned in a stationary location, the operator can command the robotic arm 212 to touch each of the fiducials of the registration fixture 205. The position of each fiducial within the robotic coordinate frame 216 can thus be determined. The operator can then touch each of the fiducials with the EM probe 203. The EM probe 203 can include a handheld EM sensor 204 having a well-defined tip position with respect to the field generator 202. By touching each of the fiducials with the EM probe 203, the position of each fiducial within the EM coordinate frame 208 can be determined. With the same points (the fiducials of the registration fixture 205) now known within each of the robotic coordinate frame 216 and the EM coordinate frame 208, a registration algorithm can be determine a transformation between the two coordinate frames.

FIG. 22C illustrates another example registration procedure that can be used to register the robotic coordinate frame 216 associated with the robotic medical system 200 with the EM coordinate system 208 associated with the EM field generator 202. This registration procedure uses one of the robotic arms 212 of the robotic system, the EM field generator 202, and an EM sensor 204 that is attached to the end effector of the robotic arm 212. With the EM sensor 204 that is attached to the end effector of the robotic arm 212, the operator can than command the robotic arm 212 to move through or trace a registration trajectory 207. In the illustrated embodiment, the registration trajectory 207 comprises the shape of a cube, although other registration trajectories comprising different shapes can be used. At various points (e.g., the vertices of the cube shape) along the registration trajectory 207, the position of the end effector in the robotic coordinate frame 216 and the position of the EM sensor 204 in the EM coordinate frame 208 can be recorded. Once a sufficient plurality of points are identified with both the robotic coordinate frame 216 and the EM coordinate frame 208, a registration algorithm can be determine a transformation between the two coordinate frames.

In robotic systems such as the system 200 illustrated in FIG. 22A, a registration procedure, such as either of the procedures described above with reference to FIGS. 22B and 22C, may be performed prior to beginning the procedure to register the EM coordinate frame 208 and the robotic coordinate frame 216.

Various disadvantages are associated with these types of registrations. For example, such registration can be tedious and time consuming. Such registrations are generally not considered automatic as they may require user input and/or may need to be performed prior to beginning a robotic medical procedure. Further, such registrations can introduce inaccuracies into the system, for example, if the operator does not navigate exactly to the fiducials. Additionally, such registrations require that the position of the EM field generator 202 remains fixed during the procedure. If the EM field generator 202 is moved (e.g., accidentally bumped by someone in the operating room or moved to allow access to the patient), the registration would need to be performed again to reestablish the relationship. This can be problematic as the EM field generator 202 may need to be moved to allow access to a fluoroscopic C-arm, for example. In this case, the EM field generator 202 would be removed, the C-arm would be brought into position to capture one or more images, then the C-arm would be removed, and the EM field generator 202 brought back into position, requiring the operator to redo the EM coordinate frame to robotic or global coordinate frame registration steps.

Figure 23:
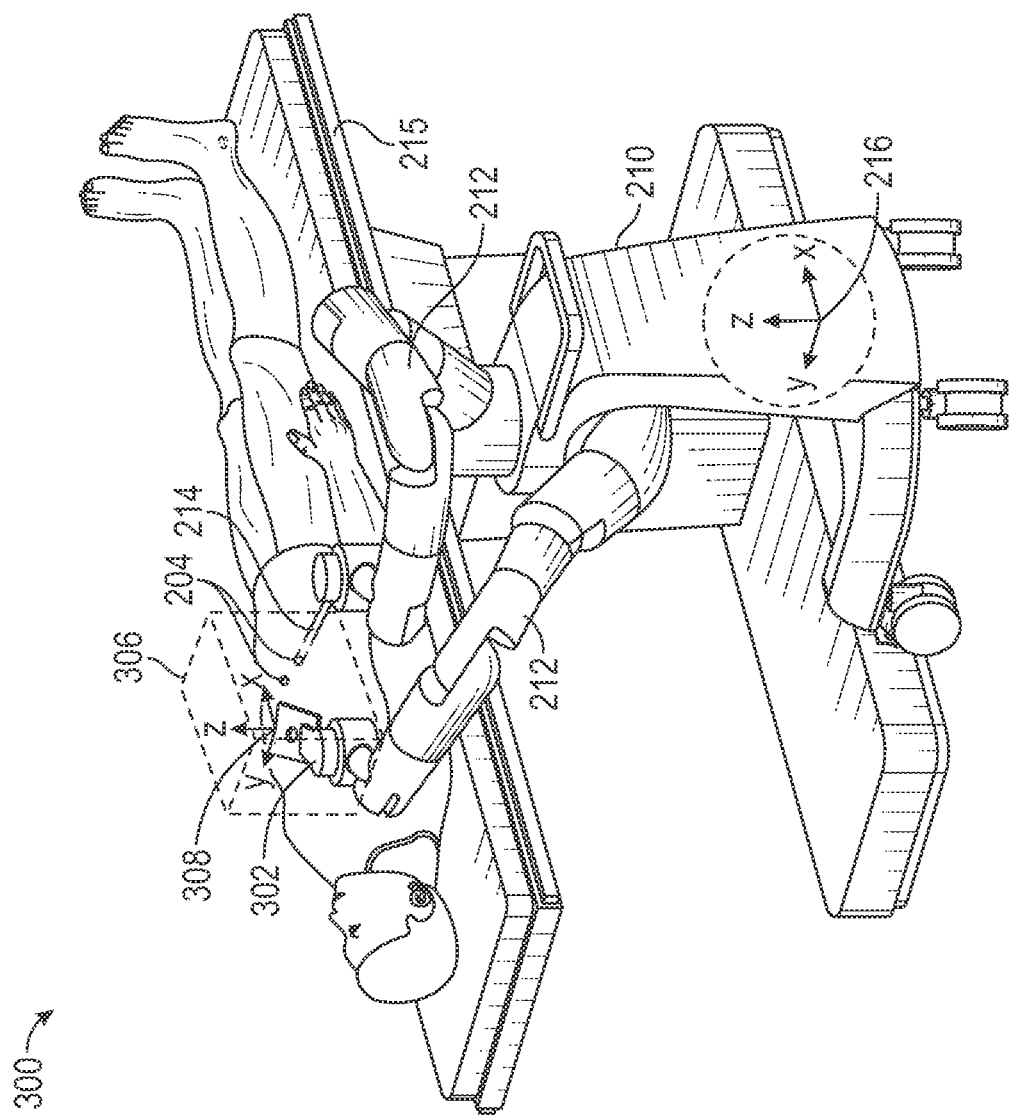
FIG. 23 is a perspective view illustrating an embodiment of a robotic medical system that includes an embodiment of a robotically controllable field generator coupled to a robotic arm of the system, according to an example embodiment.
Figure 24:
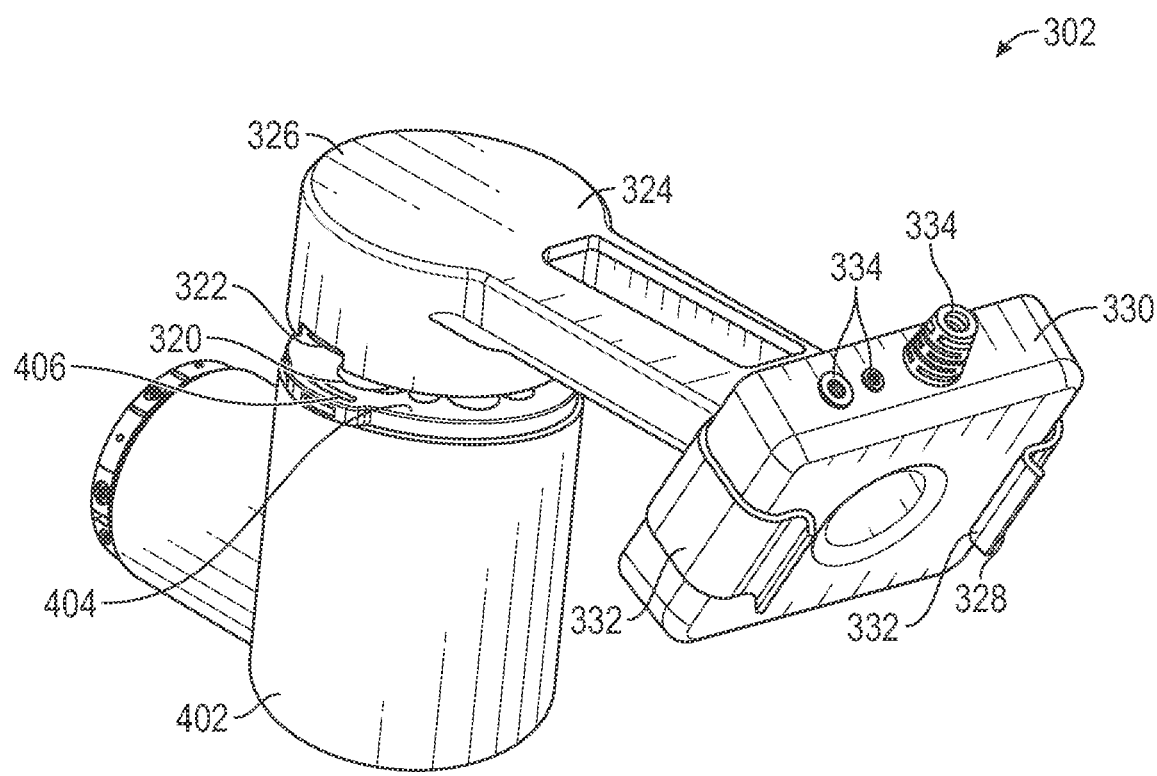
FIG. 24 is a perspective view of an embodiment of a robotically controllable field generator that is configured to couple to a robotic arm, according to an example embodiment.
Figure 25:
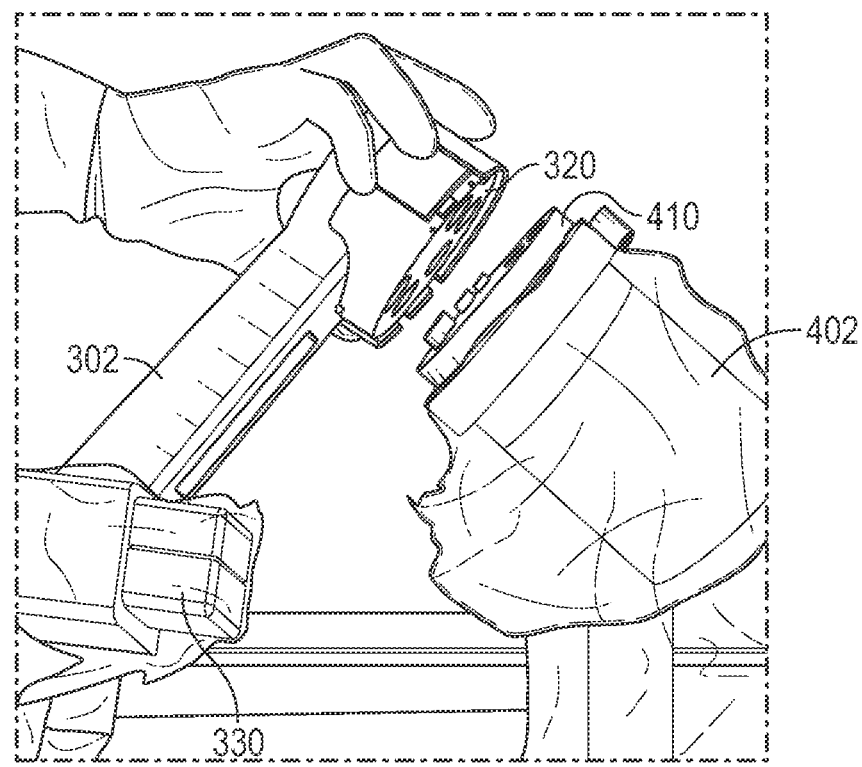
FIG. 25 illustrates that the robotically controllable field generator of FIG. 24 can be configured to couple to an instrument drive mechanism of a robotic arm, according to an example embodiment.

As will be described in more detail below, the need for these types of registrations can be reduced or eliminated through the use of robotically-controllable field generators that can be coupled directly to the robotic arms, for example, as shown in FIGS. 23-25. By coupling the robotically-controllable field generator to the robotic arm, the relationship or registration between the robotically-controllable field generator and the robotic arm can be kinematically determined, thus placing the EM coordinate frame 208 within the robotic coordinate frame 216.

Additionally, since the position of the EM field generator 202 must remain fixed during the procedure in previous systems that use registration procedures such as those described with reference to FIGS. 22B and 22C, it may be necessary to use a physically larger, and sometimes more cumbersome, EM field generator 202 in order to produce a working volume 206 with a sufficiently large size to cover the relevant medical site. In some situations or applications, this may increase the difficulty in setting up and positioning the EM field generator 202 relative to the patient. In some situations or applications, this may restrict the available space around the patient during the procedure and/or require increased set up times. The use of robotically-controllable field generators that can be coupled directly to the robotic arms, for example, as shown in FIGS. 22-25, can reduce or eliminate one or more of these restrictions associated with the EM field generator 202 as shown in FIG. 22A.

B. Overview of Robotically Controllable Field Generators

FIG. 23 illustrates an embodiment of a robotic medical system 300 that includes an embodiment of a robotically controllable EM field generator 302 that is coupled to a robotic arm 212. As will be discussed in more detail below, coupling the EM field generator 302 to the robotic arm 212 can provide several benefits including, for example, (1) allowing for a more accurate and/or simpler registration between an EM coordinate frame 308 of the EM field generator 302 and the robotic coordinate frame 216 based on the kinematics of the robotic arm 212, and/or (2) allowing the position of the EM field generator 302 to be moved or readjusted using the robotic arm 212.

Similar to the robotic medical system 200 of FIG. 22A, in the robotic medical system 300 of FIG. 23, the robotic arms 212 can be associated with a robotic coordinate frame 216. Due to the known kinematics of the robotic arms 212, the position of the robotic arms 212 can be determined with reference to the robotic coordinate frame 216. For example, because the lengths of the various links that make up the robotic arms 212 are known and the angles of between the links of the robotic arms 212 can be determined, the positions of the robotic arms 212 are kinematically defined within the robotic coordinate frame 216. Additionally, for some embodiments of the robotic medical system 300, the position and orientation of the cart 210 relative to the patient platform 215 and patient can be determined, set, or controlled such that the robotic coordinate frame 216 can be considered a global coordinate frame that can be registered to the patient or a portion of the patient's anatomy. For example, in some embodiments, up, down, right, left, etc., within the robotic coordinate frame 216 can correspond to up, down, right, left, etc., within the global coordinate frame that includes the patient, patient platform 215, and/or other components. Doing so can facilitate the operator's ability to navigate within the patient's anatomy. As a more specific example, during a bronchoscopic or ureteroscopic procedure in which the robotic system 300 comprises a cart with the robotic arms 212 extending therefrom, the cart can be positioned parallel to the bed. The bed and the cart have a common gravity vector (i.e., up points to ceiling for both of them). Using this information, the system can show the user which direction is up (anterior), or down (posterior) as they are driving the bronchoscope or ureteroscope and provide spatial context. In the case of a urologic application, the user may need to identify if the ureteroscope is in a posterior calyx or anterior calyx during target selection for percutaneous access. Since the orientation of the system is known, the system can provide anatomical context to facilitate this navigation.

As shown in FIG. 23, the EM field generator 302 can be coupled to one of the robotic arms 212. In some embodiments, the EM field generator 302 is coupled or attached to a distal end of the robotic arm 212, although the EM field generator 302 may be coupled or attached to the robotic arm 212 in other positions (e.g., positions between the distal and proximal ends of the arm). FIGS. 24 and 25, described below, illustrate a more detailed embodiment of the EM field generator 302 and show how it can, in some embodiments, couple to the robotic arm 212. Other methods and mechanisms for coupling the EM field generator 302 to the robotic arm 212 are also possible. Further, in some embodiments, the EM field generator 302 can be integrated into (e.g., can be a component on or within) the robotic arm 212 itself. For example, the EM field generator 302 can be integrated into one of the links of the robotic arm 212 (such as the distal most link) or into an instrument driver or instrument drive mechanism positioned, for example, at a distal end of the robotic arm 212. Example instrument drivers 62, 75, 83, 146 into which the EM field generator 302 can be incorporated are shown in FIGS. 14-17 above, although these examples are not limiting.

By coupling the EM field generator 302 to the robotic arm 212, the kinematics of the robotic arm 212 can be used to provide a registration between an EM coordinate frame 308 of the EM field generator 302 and the robotic coordinate frame 216 and/or global coordinate frame. That is, the kinematics of the robotic arm 212 (which as noted above are known) can be used to relate the EM coordinate frame 308 of the EM field generator 302 to the robotic coordinate frame 216 or global coordinate frame. This can provide one or more advantages over robotic medical systems that include separate EM field generators 202, such as the robotic system 200 of FIG. 22A.

One advantage can be that, by coupling the EM field generator 302 to the robotic arm 212, the need for a separate registration step (which as noted above may require user input) can be eliminated. For example, with the robotic medical system 300, it may not be necessary to manually perform a separate registration step, such as the registration steps described with reference to FIGS. 22B and 22C, in order to register the EM coordinate frame 308 to the robotic coordinate frame 216 or global coordinate frame. In the robotic medical system 300, such a registration can occur automatically (e.g., can be performed by the system), simply by attaching the EM field generator 302 to the robotic arm 212. The robotic medical system 300 can then use the known kinematics of the robotic arm 212 to relate to the EM coordinate frame 308 and the robotic coordinate frame 216 or global coordinate frame.

Another advantage that can be achieved by coupling the EM field generator 302 to the robotic arm 212 is that the accuracy of the registration between the EM coordinate frame 308 and the robotic coordinate frame 216 can be improved. As noted above, in systems such as the robotic system 200 of FIG. 22A, the registration step can introduce inaccuracies into the system, for example, due to inaccuracies in navigating during the manual registration step. In the robotic medical system 300, the accuracy of the registration between the EM coordinate frame 308 and the robotic coordinate frame 216 is largely determined by the accuracy of the kinematics of the robotic arms 212. When these are known and well defined, the registration between the EM coordinate frame 308 and the robotic coordinate frame 216 can be highly accurate.

A further advantage provided by some embodiments that include coupling the EM field generator 302 to the robotic arm 212, may be that the position of the EM field generator 302 can be adjusted using the robotic arm 212. This, in itself, can provide one or more advantages. For one, the robotic arm 212 can be used to move or reposition the EM field generator 302. This can, for example, allow the operator to adjust the position of the working volume 306 of the magnetic field of the EM field generator 302. As will be described below, the robotic arm 212 can be used to move the EM field generator 302 such that it tracks the motion of, for example, the instrument 214 as it moves through the body. Additionally, the EM field generator 302 may be moved or repositioned by robotic arm 212 to facilitate access to the patient, for example, to allow a fluoroscopic C-arm to access the patient. For example, the robotic arm 212 can be used to move the EM field generator 302 out of the way. Further, as the robotic arm 212 moves the EM field generator 302, the relationship between the EM coordinate frame 308 and the robotic coordinate frame 216, which is determined by the kinematics of the robotic arm 212, remains known. Thus, it may not be necessary to reregister the EM coordinate frame 308 to the robotic coordinate frame 216 after movement of the EM field generator 302.

Another advantage achievable by coupling the EM field generator 302 to the robotic arm 212 may include increased accuracy of the determined positions of the EM sensor 204 because the orientation and distance between the EM field generator 302 and the EM sensors 204 can be adjusted to improve accuracy. For example, the accuracy of a determined position of an EM sensor 204 may decrease closer to the edges of the working volume 306. If an EM sensor 204 is determined to be closer to an edge of the working volume 306, the robotic arm 212 can move the EM field generator 302 such that the EM sensor 204 is positioned closer to the center of the working volume 306 (or way from the edge of the working volume 306), where the accuracy of the determined position may be increased. As another example, the robotic arm 212 can move the EM field generator 302 closer to an EM sensor 204 in order to focus in on it and track its position more closely (referred to herein as EM focusing).

Additionally, because the robotic arm 212 can readily adjust the position of the EM field generator 302 without requiring a separate registration step, smaller EM field generators can be used, when compared to other robotic systems (such as the robotic system 200) that generally use stationary EM field generators. When stationary EM field generators are used, they must be large enough to provide a sufficiently large working volume to cover the medical site. Even so, they may not cover all the portions of the patient's anatomy, such as portions of the patient's anatomy that are navigated through to access the medical site. By coupling the EM field generator 302 to the robotic arm 212, smaller EM field generators, which may in some cases have smaller working volumes can be used, because the position of the working volume 306 can be adjusted by moving the EM field generator 302 with the robotic arm 202. In some embodiments, this can allow the use of a compact field generator (cFG). Use of a compact field generator is not required, however, and larger field generators can be coupled to the robotic arm in some embodiments.

When coupled to the robotic arm 212, the EM field generator 302 may function in a similar manner to the EM field generator 202 previously described. For example, in the illustrated embodiment of the system 300 of FIG. 23, one or more of the instruments 214 can include one or more EM sensor(s) 204 positioned at a distal end thereof and/or on other portions of the instruments 214. Additionally, the illustrated embodiment includes a second EM sensor 204 attached to the patient's chest, which can be used to track motion caused by the patient's respiration. When the EM sensors 204 are positioned within the working volume 206 of the EM field generator 302, the positions of the EM sensors 204 within the EM coordinate frame 308 can be determined.

Additionally, as the EM coordinate frame 308 can be registered to the robotic coordinate frame 216 using the kinematics of the robotic arm 212, the positions of the EM sensors 204 within the robotic coordinate frame 216 or the global coordinate frame can be determined. By physically connecting the EM field generator 302 to the robotic arm 212, the EM coordinate frame 308 and the robotic coordinate frame 216 or global coordinate frame can be linked together such that the positions of the EM sensors 204 can be determined within the robotic coordinate frame 216 or global coordinate frame.

For example, in the illustrated embodiment of FIG. 23, the robotic medical system 300 may include the EM field generator 302 configured to generate an EM field. The robotic medical system 300 may include robotic arms 212. A first robotic arm 212 may be coupled to the EM field generator 302 and configured to articulate to move the EM field generator 302. The robotic medical system 300 may also include one more processors configured to determine a position, in the EM coordinate frame 302 associated with the EM field generator 302, of an EM sensor 204 within the EM field. The processor(s) may also be configured to determine a registration between the EM coordinate frame 308 and the robotic coordinate frame 216 associated with the first robotic arm 212 based on determining the position of the EM field generator 302 within the robotic coordinate frame. This can be accomplished, as described above, by using the kinematics of the robotic arm 212. Based on the registration, the processor(s) can further be configured to determine the position of the EM sensor 204 in the robotic coordinate frame 216.

As another example, in the illustrated embodiment of FIG. 23, the robotic medical system 300 can include a controller or control circuit comprising one or more processors that are configured to control movement of the one or more robotic arms 212. The robotic arm 212 can be configured to articulate in response to receiving a command from the control circuit. The EM field generator 302 can be coupled to the robotic arm 212, such that the EM field generator also moves in response to one or more commands from the control circuit.

Besides the robotically controllable EM field generator 302 that is coupled to the robotic arm 212, the illustrated embodiment of the robotic system 300 of FIG. 23 may be similar in many respects to the robotic system 200 described above with reference to FIG. 22A, which includes a separate EM field generator 202, or other robotic medical systems described throughout this application or elsewhere. For example, in the illustrated embodiment, the robotic medical system 300 comprises the cart 210 including two robotic arms 212. Although illustrated with two robotic arms 212, the robotic system 300 may use other numbers of robotic arms 212. For example, FIG. 2 (described above) illustrates an example cart 11 that includes three robotic arms 12. Additionally, in some embodiments, the robotic arms 212 need not be attached to the cart 210. In some embodiments, the robotic arms can be coupled to the bed or patient platform 215, for example, as shown in FIGS. 5-10 and 14 (described above). In some embodiments, the robotic medical system 300 may comprise a plurality of robotic arms 212 (e.g., two, three, four, five six, or more robotic arms 212) that are coupled to the cart 210, the patient platform, and/or other components of the system.

Moreover, although the robotic system 300 is illustrated in FIG. 23 with a single tool or instrument 214 (e.g., a laparoscopic or endoscopic instrument) coupled to one of the robotic arms 212, it should be appreciated that other numbers of instruments 214 (e.g., two, three, four, five, six or more instruments, including laparoscopic, endoscopic, and cameras) can be used in other embodiments.

FIG. 24 illustrates an embodiment of the EM field generator 302. In the illustrated embodiment, the EM field generator 302 is configured to couple to an instrument drive mechanism 402 that can be positioned on a robotic arm, such that the EM field generator 302 is attachable to the robotic arm 212. As described above with reference to FIG. 16, instrument drive mechanisms, such as the instrument drive mechanism 402, can be configured with an interface 404 adapted to attach to various tools or instruments for use by a robotic medical system. The EM field generator 302 can be configured with a corresponding interface 320 that is configured to couple to the interface 404 of the instrument drive mechanism 402. In this way, the EM field generator 302 can couple to the robotic arms 212 in a similar manner as the other robotic tools or instruments of the robotic system.

For example, the interface 320 of the EM field generator 302 an include one or more connectors 322 configured to couple to one or more corresponding connectors 406 on the interface 404 of the instrument drive mechanism 402. Such an arrangement can allow an operator easily removably couple the EM field generator 302 to the instrument drive mechanism 402.

In the illustrated embodiment, the EM field generator 302 includes a housing 324. A proximal end 326 of the housing 234 can be configured to couple to the instrument drive mechanism 402. For example, the proximal end 326 can include the interface 320 and connectors 322. The housing 324 can extend from the proximal end 326 to a distal end 328. The distal end 328 can include a EM field generator unit 330 that is configured to generate a magnetic field. In the illustrated embodiment, the distal end 328 includes clips 332 configure to secure the EM field generator unit 330. Other mechanisms or methods for securing the EM field generator unit 330 are possible. In some embodiments, for example, as illustrated, the EM field generator unit 330 can be removable from the housing 324. In some embodiments, the EM field generator unit 330 is integrated into the housing 324. In the illustrated embodiment, the EM field generator unit 330 comprises a cFG, although other types of field generators may also be used.

The size and shape of the housing 326 can be determined or selected such that the kinematic relationship between the EM field generator unit 330 and the robotic arm to which the EM field generator 302 is attached is known, such that the kinematic registration between the EM coordinate frame associated with the EM field generator and the robotic coordinate frame associate with the robotic arm can be determined.

In the illustrated embodiment, the EM field generator unit 330 comprises one or more connectors 334. The connectors 334 may electrically connect the EM field generator unit 330 to a robotic system such that the robotic system can communicate with the EM field generator unit. In other embodiments, electrical connections may be made between the interfaces 320, 404 of the EM field generator 302 and instrument drive mechanism 402.

FIG. 25 illustrates how the EM field generator 302 can be attached to the instrument drive mechanism 402 according to one embodiment. In the illustrated embodiment, the instrument drive mechanism 402 is shown covered with a sterile drape. A sterile adapter 410 is illustrated positioned over the interface 404 of the instrument drive mechanism 402. The interface 320 of the EM field generator 302 can attach to the sterile adapter 410 such that the EM field generator 302 is coupled to the instrument drive mechanism 402 with the sterile adapter 410 positioned therebetween. As shown in FIG. 25, the EM field generator unit 330 may also be covered with a sterile drape.

Figure 26:
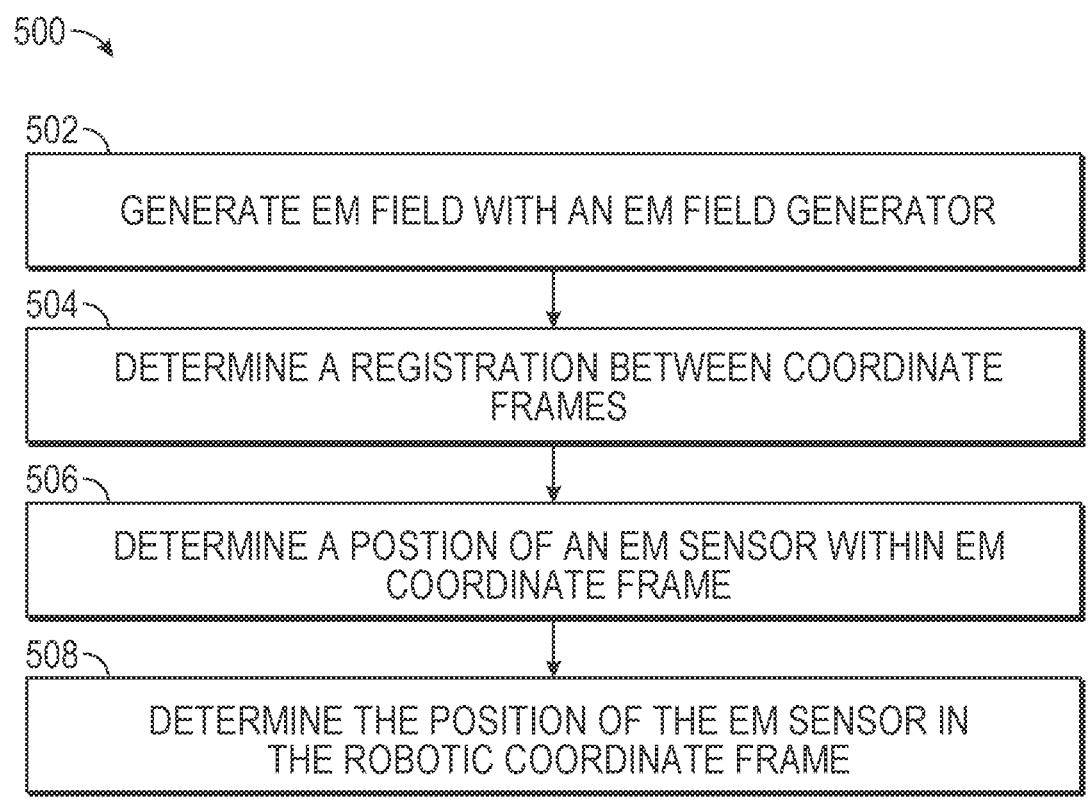
FIG. 26 is a flow chart illustrating an embodiment of a method for performing a robotic medical procedure using a robotically controllable field generator that is configured to couple to a robotic arm, according to an example embodiment.

FIG. 26 is a flow chart depicting an embodiment of a method 500 for performing a robotic medical procedure using a EM field generator configured to couple to (or otherwise connect or integrate into) a robotic arm. In the illustrated embodiment, the method begins at block 502. Block 502 can include generating an EM field with an EM field generator coupled to a first robotic arm. The EM field can be associated with an EM coordinate frame. Next, the method 500 moves to block 504, at which a registration between the EM coordinate frame and a robotic coordinate frame associated with the first robotic arm is determined. The registration can be based on determining a position of the EM field generator within the robotic coordinate frame based on kinematics of the first robotic arm. At block 506, a position of an EM sensor within the EM coordinate frame is determined. At block 508, the method includes determining the position of an EM sensor in the robotic coordinate frame based on the registration determined at block 504.

In some embodiments, the method 500 may optionally include removably coupling the EM field generator to the first robotic arm, for example, as shown in FIG. 25. The method 500 may also optionally include moving the EM field generator with the first robotic arm. Moving the EM field generator may be useful in that the working volume of the EM field can be positioned as needed to facilitate the procedure and/or the EM field generator can be moved out of the way to allow access to the patient during a medical procedure. Moving the EM field generator with the first robotic arm to adjust a position of the EM field generator relative to the EM sensor may also improve the accuracy of the determined position of the EM sensor within EM field coordinate frame (and correspondingly in the robotic coordinate frame through the registration).

The method 500 may also include moving a medical instrument coupled to a second robotic arm, wherein the robotic coordinate frame is also associated with the second robotic arm. The EM sensor can be positioned on the medical instrument, such that the guidance of navigation of the second instrument can be determined based, at least in part, on the determined position of the EM sensor.

C. Example Applications for Robotically Controllable Field Generators

In addition to providing one or more of the benefits discussed above, robotically controllable field generators coupled or otherwise integrated into robotic arms can be used to enable, facilitate, and/or improve various functionality during a robotic medical procedure. This section outlines several example applications for robotically controllable field generators that can be advantageous over other robotic systems that include, for example, static or stationary field generator.

i. Field Generator Setup and Instrument Tracking

Robotically controllable field generators coupled to or integrated into robotic arms as described above can be used to facilitate field generator setup and instrument tracking. Several examples are provided in this section to illustrate, without limiting, these concepts.

As used herein, "setup" of the EM field generator refers to determining where to position the EM field generator to facilitate a procedure. The position may be based on, for example, the determined positions of one or more EM sensors. In some instances, the position may be adjusted during the procedure, for example as one or more of the EM sensors are moved during the procedure. As noted above with reference to FIGS. 21 and 22A, the EM field generator 202 would be positioned relative to a patient such that the working volume 206 of the field generator 202 overlaps with a portion of the patient's anatomy at which the medical procedure is performed (e.g., a medical site). The EM field generator 202 could be supported by a stand or other support structure such as the patient platform 215. Once positioned, registration steps (such as those described with reference to FIGS. 22B and 22C) would be performed to register the EM coordinate frame 208 associated with the EM field generator 202 to the robotic coordinate frame 216. Further, during the procedure, the EM field generator 202 generally was not moved because movement would need to be done manually and would require that the registration steps be repeated to reregister the EM coordinate frame 208 associated with the EM field generator 202 to the robotic coordinate frame 216. Robotically-controllable EM field generators that can be repositioned using robotic arms of the system facilitate the setup procedure by allowing the system to determine locations at which to position the EM field generator and moving the EM field generator to those locations using the robotic arms of the system. Further, during the procedure, as the positions of tools and instruments that include EM sensors change, the system can adjust the position of the EM field generator such that it remains positioned in advantageous locations.

Figure 28A:
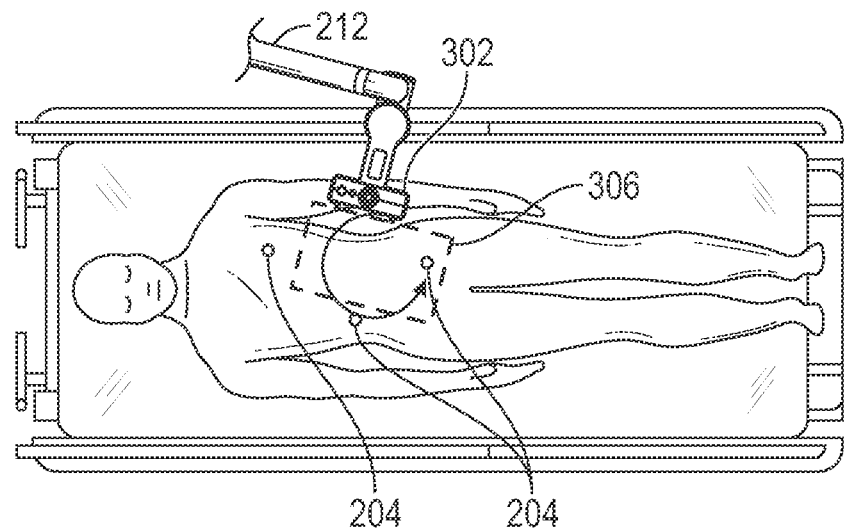
FIGS. 28A and 28B illustrate an embodiment of a robotic medical system including a robotically controllable field generator configured for facilitating setup and placement of the field generator and expanding the working volume thereof, according to an example embodiment
Figure 28B:
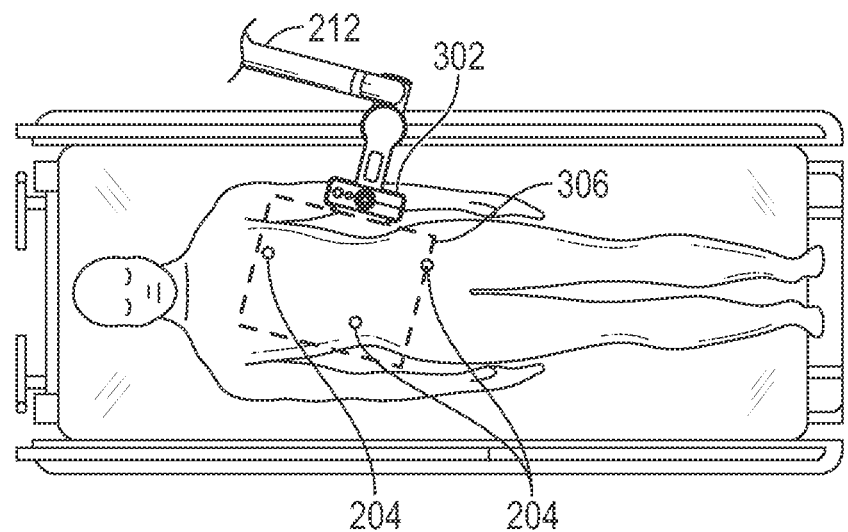

FIGS. 28A and 28B illustrate an introductory example that shows that the robotically controlled EM field generator 302 (described, for example, above with reference to FIGS. 23-25) can be used to facilitate set up and positioning of various tools and devices used for a medical procedure. Additional examples will be described in more detail further below. FIG. 28A illustrates three EM position sensors 204, as well as the EM field generator 302 coupled to a robotic arm 212. The EM position sensors 204 can be, for example, positioned on medical instruments (such as endoscopic, laparoscopic, and/or other types of surgical tools) or directly on the patient (such as, for example, EM patch sensors configured to track patient movement or respiration). For ease of illustration, the medical instruments are not illustrated.

As shown in FIG. 28A, the system can be configured to move the EM field generator 302 using the robotic arm 212 to identify the locations of the EM sensors 204. Such movement can include translation, rotation, and/or oscillation of the EM field generator 302. In FIG. 28A, an example circular path is illustrated. Once the positions of the EM sensors 202 are determined, the robotic arm 212 can move to reposition the EM field generator 302 at a comparatively improved (referred herein as a "working location") or centralized location at which the EM sensors 204 are positioned within the working volume 306 of the EM field generator 302, as shown, for example, in FIG. 28B. This can facilitate setup as the system can determine an working or central location at which to position the EM field generator 302 automatically. In related aspects, the position of one or more EM sensors 204 may be adjusted to achieve a comparatively improved arrangement of the EM sensors 204 based on the range of movement or oscillation achievable by the EM field generator, the medical procedural steps, and/or the anatomical characteristics of the patient.

In some embodiments, the system locates and determines the position and/or orientation of the EM sensors 204 and then computes the centroid or the geometric center of those positions or a shape defined by one or more of the positions. The EM field generator 302 can then be positioned, using the robotic arm 212, such that the center of the working volume 306 is aligned with, for example, the determined centroid of the positions of the EM sensors 204.

In addition, FIG. 28A illustrates that the EM field generator 302 can increase the functional size of the working volume 306. For example, if EM sensors 204 are separated such that they cannot all be fit within the working volume 306, the system can move the EM field generator (in a scanning motion) to produce a functional working volume 306 that is large enough to track all of the EM sensors 204. In some embodiments, the system may prioritize certain EM sensors 204 such that they remain constantly positioned within the working volume 306, while other EM sensors 204 are sometimes inside and sometimes outside of the working volume 306.

"Instrument tracking," as used herein, generally refers to moving the robotically controllable EM field generator using a robotic arm to track or follow motion of an EM sensor. As noted above, prior systems generally involved the use of stationary EM field generators that could not or (would not, in order to avoid re-registration) be moved to track or follow motion of an EM sensor. In such systems, if an EM sensor was moved outside of the working volume of the EM field generator, the EM sensor would no longer be detectable until it was moved back into the working volume. Robotically controllable field generators that can be moved with robotic arms can facilitate instrument tracking by allowing the EM field generator to be moved or otherwise adjusted to track motion of one or more instrument sensors. Thus, rather than having an EM sensor move outside of the working volume of the EM field generator, the EM field generator can be moved along with the EM sensor such that the EM sensor remains positioned within the working volume, facilitating continual tracking of the EM sensor.

Figure 27A:
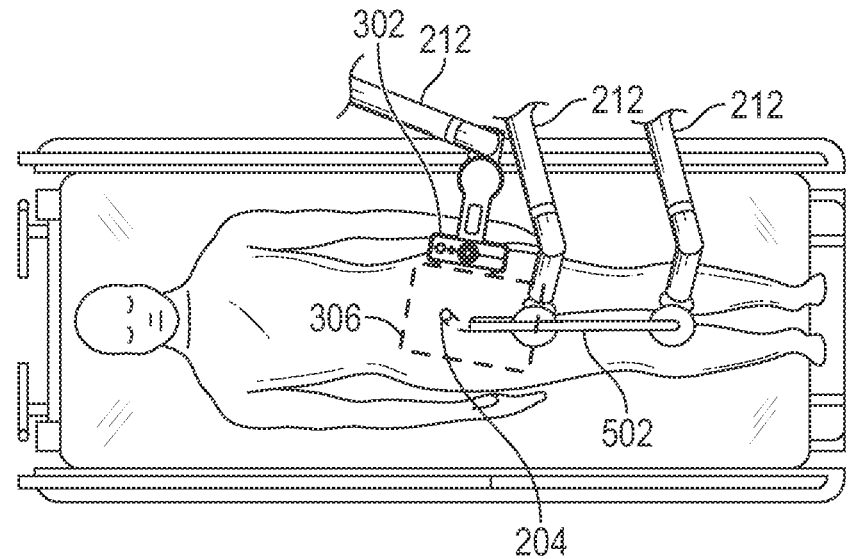
FIGS. 27A and 27B illustrate an embodiment of a robotic medical system including a robotically controllable field generator configured for automatic instrument tracking and mapping of anatomical features, according to an example embodiment.
Figure 27B:
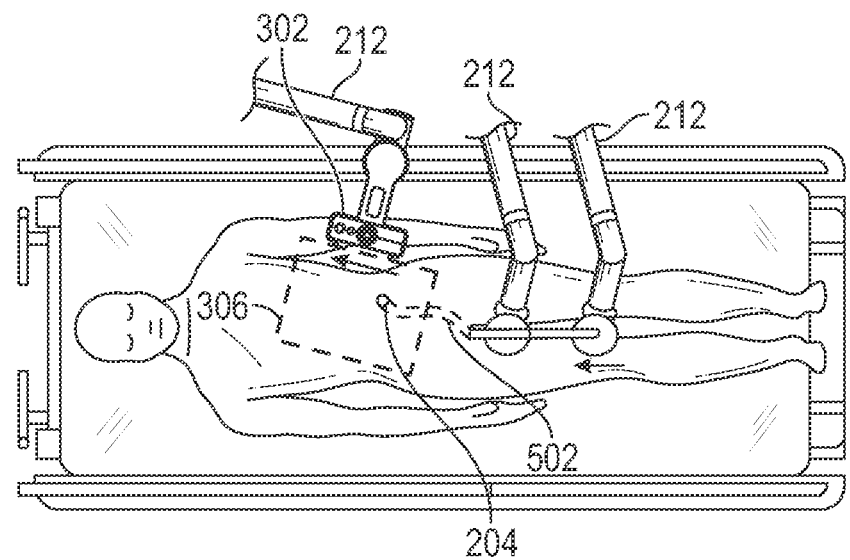

FIGS. 27A and 27B illustrate an introductory embodiment of automatic instrument tracking that can be facilitated using a robotically controllable field generator, such as the EM field generator 302 described above with reference to FIGS. 23-25. In particular, FIGS. 27A and 27B illustrate an example of automatic instrument tracking during an example medical procedure, such as a ureteroscopic procedure, during which a ureteroscope 502 is robotically navigated through a patient orifice, through the ureter, and into a kidney. Although a ureteroscopic procedure is illustrated, automatic instrument tracking can be used in other types of procedures, including endoscopic and/or laparoscopic procedures. FIG. 27A illustrates the procedure at an earlier or first time/step (e.g., just after insertion of the ureteroscope 502) and FIG. 27B illustrates the procedure at a later or second time/step (e.g., after the distal tip of the ureteroscope 502 has been navigated into the kidney).

As illustrated in FIGS. 27A and 27B, the ureteroscope 502 can be coupled to one or more robotic arms 212 that are configured to manipulate the ureteroscope 502 and perform the insertion thereof as described, for example, with respect to FIG. 3. In FIGS. 27A and 27B, the EM field generator 302 is coupled to a third robotic arm 212 that is configured to move to adjust the position of the EM field generator 302 (and correspondingly, the position of the working volume 306 of the magnetic field generated by the EM field generator 302). As described above, because the EM field generator 302 is attached to the robotic arm 212, the EM coordinate frame associated with the EM field generator 302 can be automatically registered to the robotic coordinate frame associated with the robotic arms 212 through the kinematics of the robotic arm 212 to which the EM field generator 302 is attached.

As shown in FIGS. 27A and 27B, the system can be configured to move the EM field generator 302 with the corresponding robotic arm 212 such that it automatically tracks the position of the ureteroscope 502. In the illustrated embodiment, the ureteroscope 502 includes an EM sensor 204 positioned on the distal tip thereof. As described above, the position of the EM sensor 204 can be determined relative to the EM coordinate frame when the EM sensor 204 is positioned within the working volume 306 of the EM field generator 302. Further, because the EM coordinate frame can be registered to the robotic coordinate frame, the position of the EM sensor 204 within the robotic coordinate frame is also determinable.

As the ureteroscope 502 is inserted further into the patient, the robotic arm 212 to which the EM field generator is attached can move or adjust to automatically reposition the EM field generator such that the position sensor 204 remains positioned within the working volume 306 of the EM field generator. In some embodiments, this automatic tracking of the ureteroscope 502 is configured such that the EM field generator 302 is moved or adjusted so that the EM sensor 204 remains positioned at the center of the working volume 306, although this need not be the case in all embodiments. Additionally, in some embodiments, the orientation of the EM field generator 302 can be adjusted relative to the EM sensor 204 to provide for optimal or improved accuracy in determining the position thereof.

This type of automatic tracking can advantageously allow that the position of the ureteroscope 502 be tracked throughout the procedure (e.g., from insertion to work within the kidney). This may not be possible in robotic systems that use a static or stationary field generator. As noted above, static or stationary field generators are often set up such that their working volume is centered on the primary medical site (e.g., the kidney). In this position, the working volume may not extend sufficiently to provide coverage of insertion and navigation through the ureter. Thus, in systems that use static or stationary field generators, operators may not be able to utilize EM based navigation until they have navigated the instrument into the working volume of the field generator. Moving a static or stationary field generator to follow an instrument during insertion and navigation of an instrument to the medical site is also generally not possible as a registration step would need to be re-performed each time the field generator is moved, which is impractical and may cause delays during the medical procedure, potentially negatively impacting the outcome of the procedure.

As shown in FIGS. 27A and 27B, however, the robotically controlled EM field generator 302 can readily track the position of the ureteroscope 502 from insertion to working within the kidney as the robotic arm 212 can reposition the EM field generator 302 as needed, and the kinematics of the robotic arm 212 can be used to provide a continuous registration between the EM coordinate frame and the robotic coordinate frame.

An additional advantage that can be achieved using the automatic instrument tracking shown in FIGS. 27A and 27B is improved anatomical mapping. As an instrument is navigated through a patient's anatomy, the positions of an EM sensor on the instrument can be used to build an anatomical map. For example, in the case of bronchoscopy, as a bronchoscope including an EM sensor is navigated through the patient's airways, the determined positions of the EM sensor can be used to produce a map of the patient's lungs. With static or stationary EM field generators, this is only possible for regions within the working volume of the EM field generator. However, through the use of a robotically controllable EM field generator 302 that allows for a robotic arm 212 to reposition the EM field generator 302, the capability of generating anatomical maps is increased.

Using the example of FIGS. 27A and 27B, the position of the EM sensor 204 can be determined from insertion (FIG. 27A) to within the kidney (FIG. 27B) producing a generally complete anatomical map of the patient's urinary tract. In contrast, if a static field generator were used with its working volume centered on the kidney, EM sensor data might not be available that could be used to map the patient's ureter. Accordingly, use of the robotically controllable EM field generator 302 as described herein can extend the ability to produce anatomical mapping using EM sensor data, leading to more complete anatomical maps.

Figure 29:
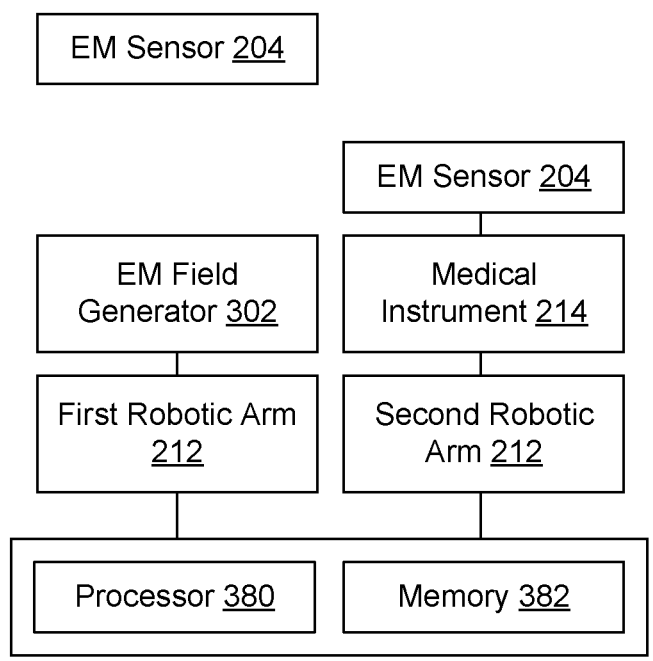
FIG. 29 is a block diagram representative of an embodiment of a robotic medical system that includes a robotically controllable field generator coupled to a robotic arm of the system, according to an example embodiment.

FIG. 29 is a block diagram representative of a robotic medical system 300, such as the example illustrated in FIG. 22A, which includes a robotically controllable EM field generator 302 mounted on a robotic arm 212. As shown in FIG. 29 (and also in FIG. 23), the system 300 can include one or more robotic arms 212. In the illustrated embodiment, the system 300 includes a first robotic arm 212 and a second robotic arm 212, although in other embodiments, other numbers of robotic arms (e.g., one, two, three, four, five, six or more) can be included. As shown, the first robotic arm 212 is coupled to an EM field generator 302. As described above, the EM field generator 302 can be attached or coupled to the first robotic arm 212 or it can be integrated directly into the first robotic arm 212 itself. The EM field generator 302 is configured to generate an EM field having a working volume 306, within which the positions of EM sensors 204 can be determined relative to an EM coordinate frame 308. The first robotic arm 212 can be configured to be able to adjust the position of the EM field generator 302. For example, the first robotic arm 212 can move (e.g., change pose or shape) to readjust the position of the EM field generator 302, and correspondingly, the position of the working volume 306 of the EM field.

The first robotic arm 212 (as well as the other robotic arms 212 of the system) is associated with a robotic coordinate frame 216 as described above. Based on the kinematic position of the arm 212, the position of the EM field generator 302 within the robotic coordinate frame 216 can be determined. This allows for a registration or mapping between the EM coordinate frame 308 and the robotic coordinate frame 216 to be determined as described above. As shown in FIG. 29 (and also in FIG. 23), the system 300 can include one or more EM sensors 204. The positions of the EM sensors 204 can be determined relative to the EM coordinate frame 308 and mapped to the robotic coordinate frame 216 using the registration previously described.

In FIG. 29 (and FIG. 23), one of the EM sensors 204 is positioned on a medical instrument 214. The medical instrument 214 can be, in some embodiments, coupled to the second robotic arm 212. This can allow the second robotic arm 212 to manipulate and control the medical instrument 214. As the second robotic arm 212 manipulates and controls the medical instrument 214, the position of the medical instrument 214 can be determined based on the determined position of the EM sensor 204. As shown in FIG. 29, the system 300 can include additional EM sensors 204 that can be tracked as well.

The block diagram of FIG. 29 further illustrates that the system 300 can include a processor 380 and a memory 382. The memory 382 can be used to store instructions that when executed by the processor 380 can enable various functionality of the system 300, such as determining and using the EM coordinate frame 308 to robotic coordinate frame 216 registration and mapping, setup of the EM field generator 302, and tracking of the medical instrument 214 as described in this section and throughout this application. For example, the processor 380 can be in communication with the first robotic arm 212 and the EM field generator 302 and configured to determine a position of one or more of the EM sensors 204 within the EM field generated by the EM field generator 302, and adjust the position of the EM field generator 302 by commanding movement of the first robotic arm 212 based on the determined position of the EM sensor 204. The commanded movement of the first robotic arm 212 based on the determined position of the EM sensor 204 can be used to setup the position of the EM field generator 302 or to track the position of the EM sensor 204 as it moves during the procedure.

In some embodiments, the processor 302 is configured to first determine the position of the EM sensor 204 relative to the EM coordinate frame 308, and then map that position into the robotic coordinate frame 216. As described above, this can be accomplished by, for example, (i) determining the position of the EM sensor 204 within the EM field relative to the EM coordinate frame 308 associated with EM field generator 302, (ii) determining a registration between the EM coordinate frame 308 and the robotic coordinate frame 216 associated with the first robotic arm 212 based on determining a position of the EM field generator within the robotic coordinate frame 216, and (iii) based on the registration, determining the position of the EM sensor 204 in the robotic coordinate frame 216. Determining of the position of the EM field generator 302 within the robotic coordinate frame 216 at step (ii) can be based on kinematics of the first robotic arm 212.

FIGS. 30A-33D illustrate various examples or approaches to moving the EM field generator 302 with the first robotic arm 204 based on the determined position of the EM sensor 204 in order to facilitate field generator setup and instrument tracking.

Figure 30B:
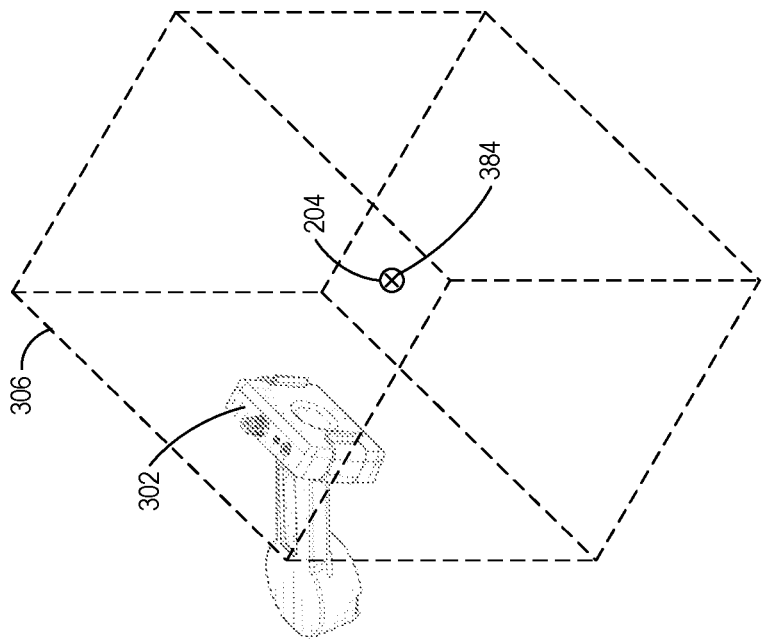
FIGS. 30A and 30B are perspective views that illustrate an example of moving an EM field generator with a robotic arm such that an EM sensor is positioned at a predetermined position within an EM field, according to an example embodiment.
Figure 30A:
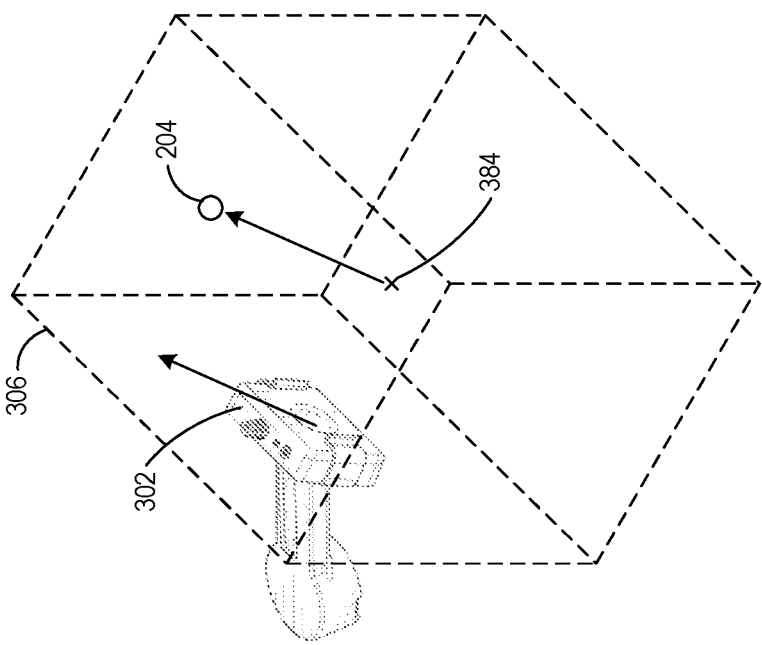

FIGS. 30A and 30B are perspective views that illustrate an example of moving an EM field generator with a robotic arm such that an EM sensor is positioned at a predetermined position within an EM field. This can occur, for example, during field generator setup and can advantageously be used to position the EM field generator 302 relative to an EM sensor 204. In some embodiments, it can be advantageous to setup or align the EM field generator 302 such that the EM sensor 204 is located at a predetermined position with the working volume 306 of the EM field. This can be useful for several reasons. For example, in some instances, this can center the working volume 306 of the EM field around the EM sensor 204. This can help ensure that, if the EM sensor 204 is moved, it can still be tracked as it can move without moving outside of the working volume 306. As another example, this can increase the accuracy of the determined position of the EM sensor 204 because, in some instances, the ability to determine the position of the EM sensor 204 within the EM field may be more accurate toward the center of the working volume 306 than on the extremities of the working volume 306. Accordingly, in some embodiments, the predetermined position comprises the center of the working volume 306, and the EM field generator 302 is moved such that the EM sensor 204 is positioned at the center of the working volume 306 as shown in FIGS. 30A and 30B.

In FIGS. 30A and 30B, the predetermined position 384 is the center of the working volume 306 and is represented in the figures as an x. FIG. 30A illustrates the system in a first state, prior to moving the EM field generator 302 such that the EM sensor 204 is positioned at the predetermined position 384. As shown in FIG. 30A, the EM sensor 204 is positioned within the working volume 306 of the EM field generator 302, but it is not located at the predetermined position 384. To position the EM sensor 204 at the predetermined position 384, the EM field generator 302 must be moved in the direction of the arrows shown, causing a corresponding movement of the working volume 306 and the predetermined position 384. FIG. 30B illustrates the system in a second state, after the adjusting the position of the EM field generator 302 based on the determined position of the EM sensor 204 to causes the EM sensor 204 to be positioned at a predetermined position 384 within the EM field. In this example, the EM field generator 302 can now be considered "setup" as its position has been adjusted relative to the EM sensor 204. Notably, the movement of the EM field generator 302 can be accomplished with the robotic arm 212 to which the EM field generator 302 is attached. Further, points within the EM coordinate frame, such as the position of the EM sensor 204 and the predetermined position 384 can be mapped into the robotic coordinate frame using the registration based on the kinematics of the robotic arm such that all positions (e.g., EM sensor positions, the predetermined position 384, and the position of the EM field generator 302) can be processed in a single space (e.g., the robotic coordinate frame).

In FIGS. 30A and 30B the predetermined position within 384 within the working volume 306 of the EM field comprises the center of a working volume 306. This, however, need not be the case in all embodiments, and other predetermined positions 384 within the working volume 306 can be used. For example, another possible predetermined position 384 may comprise a position located on one extreme of the working volume 306 such that the EM sensor 204 can be moved entirely across the working volume 306 before the EM field generator 302 would need to be repositioned to continue tracking the EM sensor 204.

In some embodiments, the EM field generator 302 can be positioned such that the EM sensor 204 is positioned within a predetermined region or portion of the working volume 306 of the EM field, rather than at a specific predetermined position. FIGS. 31A and 31B are perspective views that illustrate an example of moving an EM field generator 302 with a robotic arm 212 such that the EM sensor 204 is positioned at within a predetermined region 386 within the working volume 306. In FIGS. 31A and 31B, a predetermined region 386, representing a subsection of the working volume 386 is illustrated. In the figures, both the working volume 306 and the predetermined region 386 are represented as rectangular prisms. This, however, is merely one example, and other shapes for the working volume and the predetermined region 386 are possible. Further, the shape of the predetermined region 386 need not correspond to the shape of the working volume 306. For example, the working volume 306 may comprise the shape of a rectangular prism and the predetermined region 386 may comprise the shape of a sphere within the working volume 306. In some embodiment, the predetermined region 386 may represent a portion of the working volume 306 within which the positions of EM sensors 204 can be determined with increased accuracy, and as such, it may be desirable to position the EM field generator 302 relative to the EM sensor 204 such that the EM sensor 204 is within the predetermined region 386. In some embodiments, the predetermined region 386 may comprise the entirety of the working volume 306.

FIG. 31A illustrates the system in a first state, prior to adjusting the position of the EM field generator 302 such that the EM sensor 204 is positioned within the predetermined region 386. As shown, the EM sensor 204 is positioned within the working volume 306 of the EM field, but it is not positioned within the predetermined region 386. In order to position the working volume 306 such that the EM sensor 204 is positioned within the predetermined region 386, the EM field generator 302 can be moved, using the robotic arm 212 to which it is attached, in the direction of the illustrated arrows. This motion causes a corresponding movement of the working volume 306 and the predetermined region 386. FIG. 31B illustrates the system in a second state, after adjusting the position of the EM field generator 302 such that the EM sensor 204 is positioned within the predetermined region 386. As shown, the EM field generator 302 has been moved using the robotic arm 212 such the EM sensor 204 is now positioned within the predetermined region 386. As before, the registration described above can map points in the EM coordinate frame to corresponding points in the robotic coordinate frame based on the kinematics of the arm such that all positions can be represented in a single space.

The examples of FIGS. 31A-31B and 32A-32B involve adjusting the position of the EM field generator 302 relative to the EM sensor 204. In some embodiments, the system may, additionally or alternatively, determine an orientation of the EM sensor 204 within the EM field, and adjust at least one of an orientation and the position of the EM field generator 302 by commanding movement of the first robotic arm 212 based on the determined orientation of the EM sensor 204. In certain instances, the accuracy with which the position of the EM sensor 204 can be determined within the working volume 306 may be influenced or affected by the orientation of the EM sensor 204 relative to the EM field generator 302. Accordingly, in some embodiments, the processor 380 is configured to adjust the at least one of the orientation and position of the EM field generator based on the determined orientation of the EM sensor to increase an accuracy of the determined position of the EM sensor 204 within the EM field. This can involve, for example, adjusting the pitch, yaw, and/or roll of the EM field generator 302 relative to the EM sensor 204 using the robotic arm 212 to which the EM field generator 302 is attached.

As described above, the examples of FIGS. 31A-31B and 32A-32B have generally related to determining a position for the EM field generator 302 relative to a determined position of an EM sensor 204 in order to setup the EM field generator 302 for a procedure. This setup is facilitated by mounting the EM field generator 302 on the robotic arm 212 such that its position can be robotically adjusted. Robotic adjustment of the position of the EM field generator 302 also facilitates instrument tracking, which can occur as one or more of the EM sensors 204 move during the procedure. As noted previously, one or more of the EM sensors 204 may be positioned on medical tools or instruments that are moved during the procedure. The EM sensors 204 can allow tracking of the movement of these tools. As described in the following examples, as the movement of the EM sensors 204 is detected, new positions for the EM field generator 302 can be determined, and the EM field generator 302 can be moved using the robotic arm 212 to which it is attached.

Figure 32B:
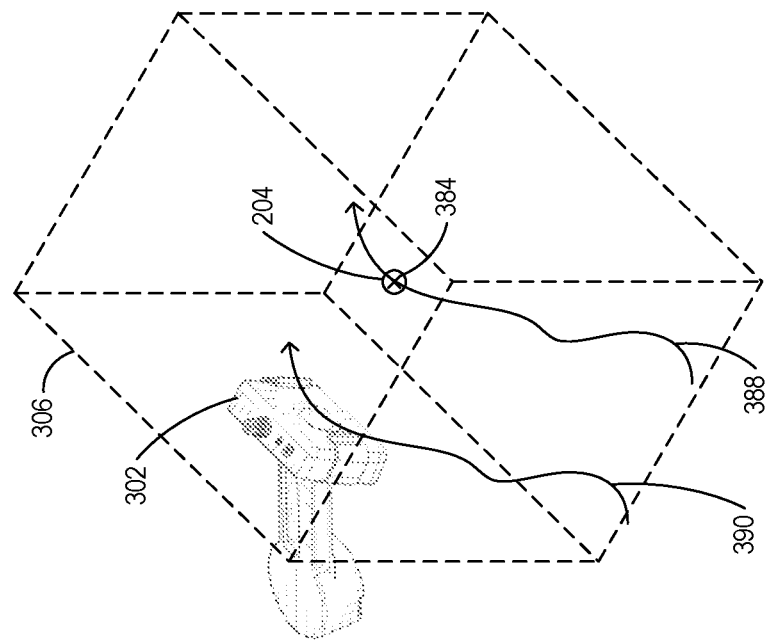
FIGS. 32A and 32B are perspective views that illustrate an example of moving an EM field generator with a robotic arm along a path that tracks a path of movement of an EM sensor, according to an example embodiment.
Figure 32A:
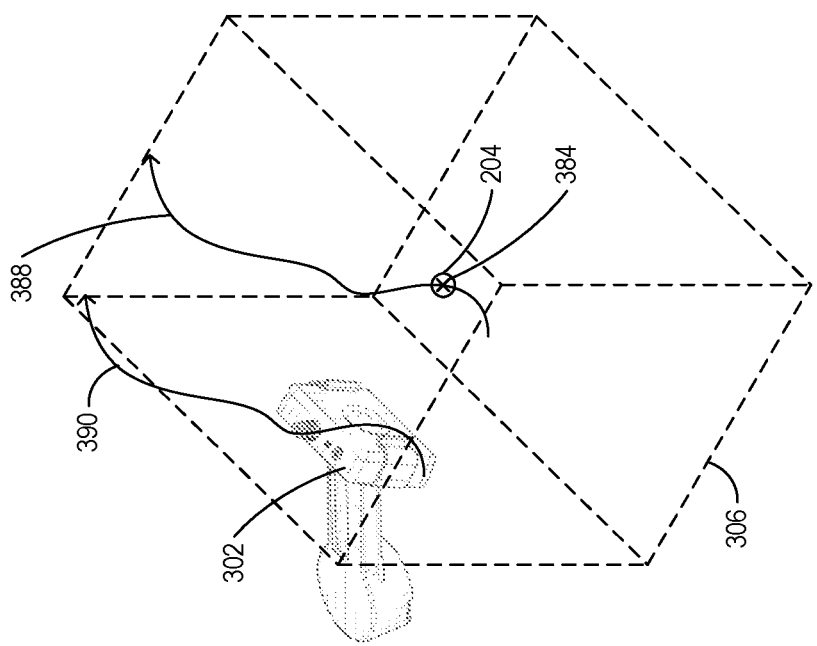

FIGS. 32A and 32B are perspective views that illustrate an example of moving an EM field generator 302 with a robotic arm 212 along a path 390 that tracks a path 388 of movement of an EM sensor 204. In this manner, the path 390 of the field generator 302 tracks, follows, or mirrors the path 388 of the EM sensor 204. In the example of FIGS. 32A and 32B, the system is configured to maintain the position of the EM field generator 302 such that the EM sensor 204 remains positioned at the predetermined location 384 (in the illustrated example, the center of the working volume 306) as the EM sensor 204 is moved along the path 388.

During a medical procedure, a medical instrument (such as the medical instrument 214 of FIGS. 23 and 29) that includes the EM sensor 204 positioned thereon may be navigated through the patient's anatomy. This motion of the EM sensor 204 (and the corresponding instrument 214) is represented by the path 388. FIG. 32A illustrates the system with the EM sensor 204 positioned at a first location along the path 388. If the EM sensor 204 were to continue along the path 388 while the EM field generator 302 remains stationary, the EM sensor 204 would no longer be positioned at the predetermined position 384 within the working volume 306. To maintain the EM sensor 204 at the predetermined position 384 within the working volume 306, the EM field generator 302 must be moved along a corresponding path 390. In this manner, the EM field generator 302 tracks or follows the movement of the EM sensor 204. FIG. 32B illustrates the system after movement of the EM sensor 204 along its path 388. Because the EM field generator 302 has also moved along the corresponding path 390, the EM sensor 204 remains positioned at the predetermined position 384 within the working volume 306. This is enabled by moving the EM field generator 302 with the robotic arm 212 to which it is attached.

In some embodiments, tracking of the EM sensor 204 with the EM field generator 302 need not have a direct correspondence. For example, the path 390 of the EM field generator 302 need not directly correspond to the path 388 of the EM sensor 204. FIGS. 33A-33D illustrate an example.

FIGS. 33A-33D are perspective views that illustrate an example of moving the EM field generator 302 with a robotic arm 212 such that the EM sensor 204, which is moving along the path 388 remains positioned within the predetermined region 386 of the working volume 306. As will be shown, in this example, the EM field generator 302 tracks the movement of the EM sensor 204 but is not moved along a path that directly corresponds to the path 388 of the EM sensor 204. In this example, the system is configured to adjust the position of the EM field generator 302 when the EM sensor 204 is moved to the boundary or outside of the predetermined region 386 of the working volume 306. For example, the processor 380 can be configured to command movement of the EM field generator 302 with the first robotic arm 212 during movement of the medical instrument 214 that includes EM sensor 204 such that the EM sensor 204 remains positioned within the predetermined region 386 of the working volume 306 of the EM field.

Figure 33B:
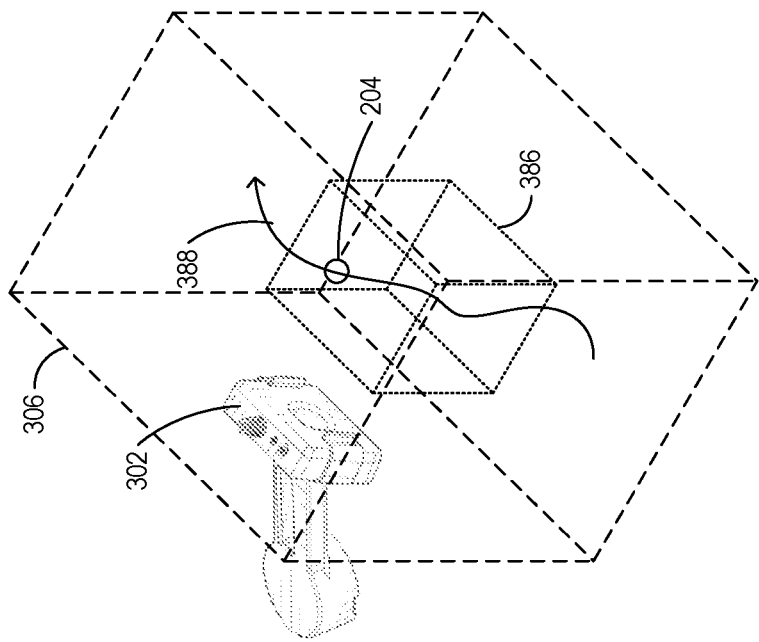
FIGS. 33A-33D are perspective views that illustrate an example of moving an EM field generator with a robotic arm such that an EM sensor moving along a path remains positioned within a predetermined region of an EM field, according to an example embodiment.
Figure 33A:
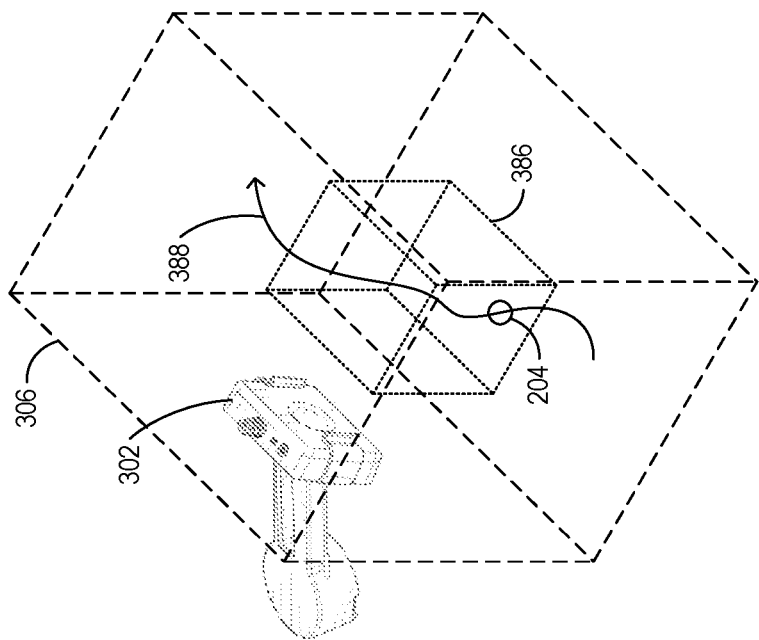
Figure 33D:
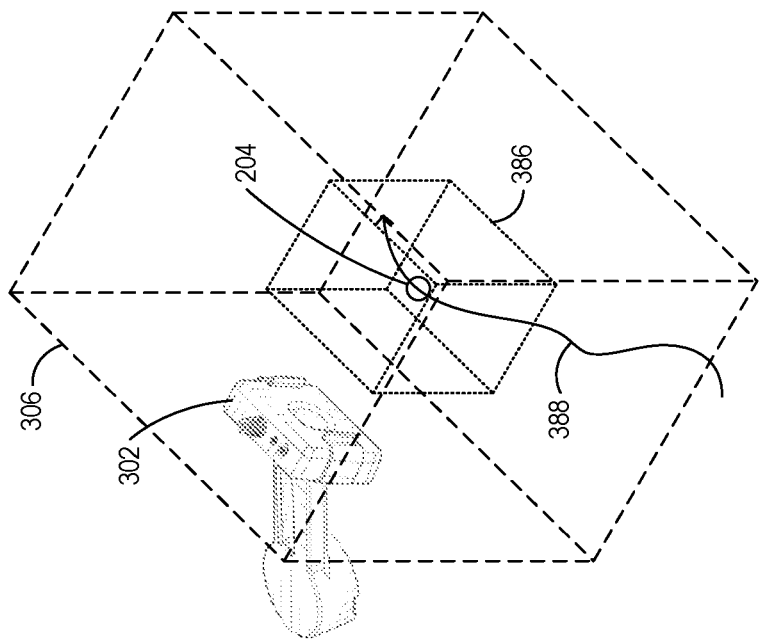
Figure 33C:
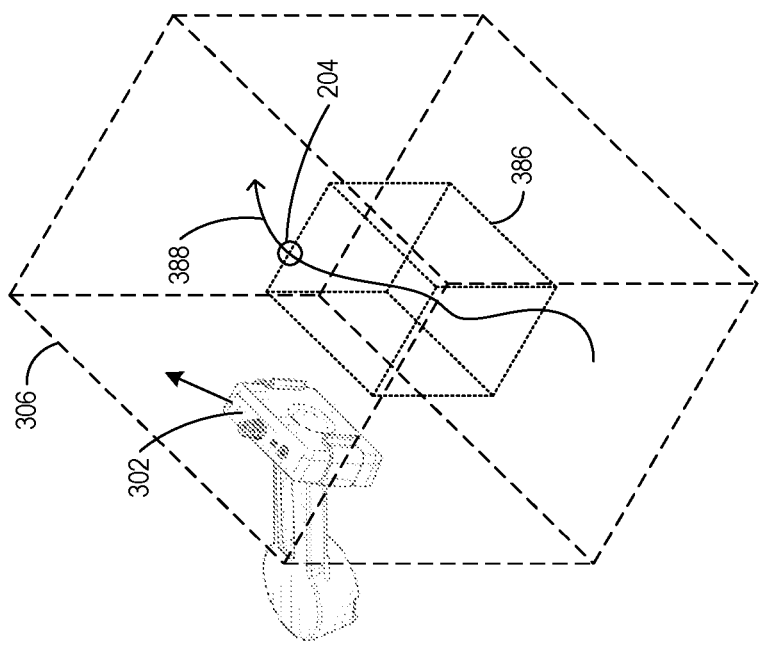

FIG. 33A illustrates the system in a first state. As shown, the EM sensor 204 is positioned within the predetermined region 386 of the working volume 306 and traveling along the path 388. FIG. 33B illustrates the system at a second state. As shown, the EM sensor 204 has continued along the path 204 but is still positioned within the predetermined region 386. Since the EM sensor 204 is still positioned within the predetermined region 386, the EM field generator 302 has not yet been moved. FIG. 33C illustrates a third state, wherein the EM sensor 204 has reached an edge or boundary of the predetermined region 386. If the EM sensor 204 continues along the path 388 while the EM field generator 302 remains stationary, the EM sensor 204 will move outside of the predetermined region 386. To maintain the EM sensor 204 within the predetermined region 386, the EM field generator 302 must be moved in the direction of the illustrated arrow. This movement can be determined, for example, by the processor 380, which can command the robotic arm 212 to move the EM field generator 302. FIG. 33D illustrates the system in a fourth state, after the EM field generator 302 has been moved. As shown, the movement can reposition the EM field generator 302 such that the EM sensor 204 is once again positioned within the predetermined region 386, even as the EM sensor 204 continues along the path 388. In this way, the EM field generator 302 is once again moved to track or follow the movement of the EM sensor 204, even though the movement of the EM field generator 302 does not directly correspond to the movement of the EM sensor 204 as in the example of FIGS. 32A and 32B.

Figure 34:
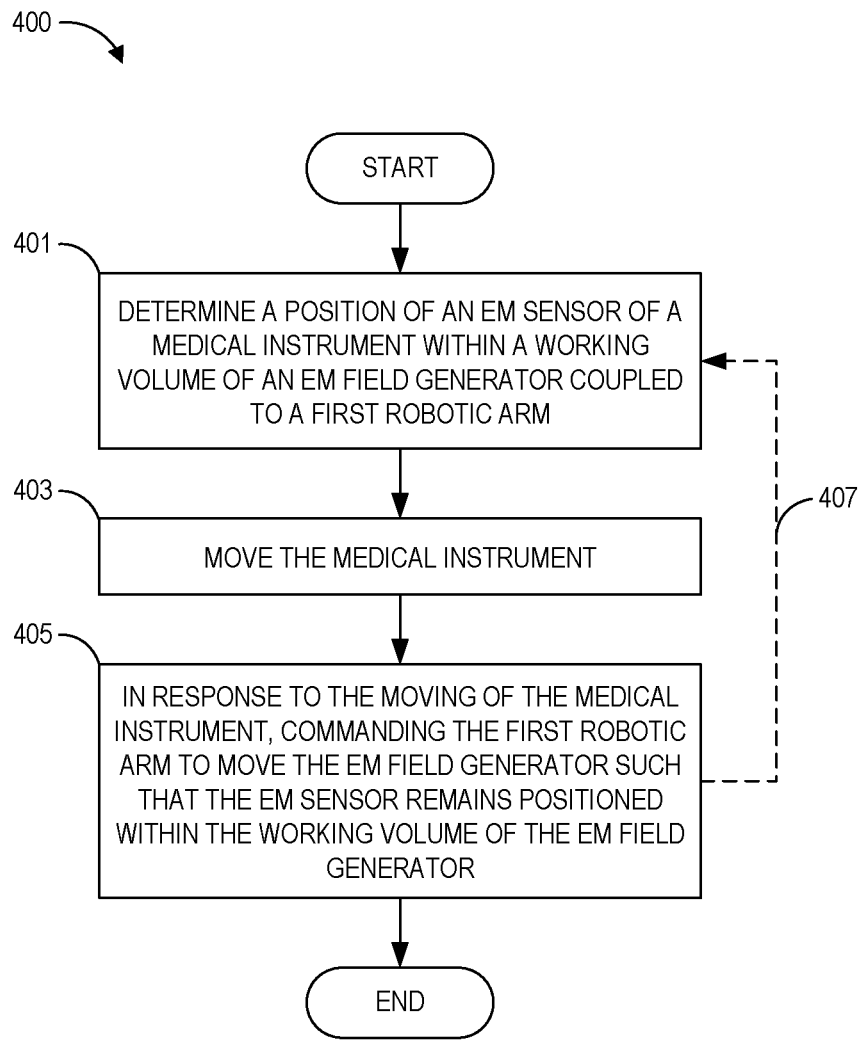
FIG. 34 is a flowchart providing an example method for moving an EM field generator coupled to a robotic arm based on a determined position of an EM sensor within an EM field, according to an example embodiment.

FIG. 34 is a flowchart providing an example method 400 for moving an EM field generator coupled to a robotic arm based on a determined position of an EM sensor within an EM field. The method 400 can, for example, be executed by the processor 380 to provide field generator setup and instrument tracking. The method 400 begins at block 401, which involves determining a position of an EM sensor of a medical instrument within a working volume of an EM field generated by an EM field generator coupled to a first robotic arm. The position of an EM sensor can be determined relative to an EM coordinate frame associated with the EM field generator. In some embodiments, the position of the EM sensor can further be determined relative to a robotic coordinate frame associated with the first robotic arm by applying a registration determined based on the kinematics of the robotic arm as described above.

The method 400 include block 403, where medical instrument is moved. Movement of the medical instrument causes a corresponding movement of the EM sensor positioned thereon. In some embodiments, the medical instrument comprises a manually controlled instrument, and movement of the medical instrument is achieved manually. In other embodiments, the medical instruments comprises a robotically controllable instrument. For example, the medical instrument can be coupled to a second robotic arm, and moving the medical instrument can comprise moving the instrument with the second robotic arm. In some embodiments, moving the instrument with the second robotic arm comprises articulating the second robotic arm. The medical instrument can be coupled to an instrument drive mechanism, and moving the medical instrument with the second robotic arm can comprise actuating the medical instrument with the instrument drive mechanism. Movement of the instrument can be detected by determining that the position of an EM sensor attached to the instrument has moved.

The method 400 includes block 405, which involves, in response to the moving of the medical instrument, commanding the first robotic arm to move the EM field generator such that the EM sensor remains positioned within the working volume of the EM field generator. For example, if movement of the medical instrument would move the EM sensor outside of the working volume, the EM field generator can be repositioned using the first robotic arm to maintain the EM sensor within the working volume of the EM field.

In some embodiments, commanding the first robotic arm to move the EM field generator causes the EM field generator to track the movement of the medical instrument. For example, commanding the first robotic arm to move the EM field generator can comprise moving the EM field generator such that the EM sensor is positioned or remains positioned within a predetermined region of the working volume of the EM field as shown in the examples of FIGS. 31A-31B and 33A-33D. As another example, commanding the first robotic arm to move the EM field generator can comprise moving the EM field generator such that the EM sensor is or remains positioned at a predetermined position within the working volume of the EM field as shown in the examples of FIGS. 30A-30B and 32A-32B.

In some embodiments, the method 400 can optionally include determining an orientation of the EM sensor within the EM field, and adjusting at least one of an orientation and the position of the EM field generator by commanding movement of the first robotic arm based on the determined orientation of the EM sensor. As described above, adjusting the at least one of the orientation and position of the EM field may increase accuracy of the determined position of the EM sensor within the working volume of the EM field.

Additionally, the method 400 can be performed as a loop as indicated by dashed line 407 to continually track an EM sensor and adjust the position of the EM field generator accordingly. That is, at a plurality of discrete time steps, the position of the EM sensor can be determined, and the EM field generator can be readjusted based on each newly determined position.

The examples provided above have shown that a robotic system, such as the system 300 shown in FIGS. 23 and 29, can be configured to move an EM field generator 302 using a robotic arm 312 to setup the EM field generator 302 relative to one EM sensor 204 and/or to track movement of one EM sensor 204. However, the system 300 is not limited to embodiments with one EM sensor 204. For example, the processor 380 can be configured to determine positions of a plurality of EM sensors 204 within the EM field, determine a generator position for the EM field generator 302 based on the determined positions of the plurality of EM sensors 204, and command the first robotic arm 212 to move the EM field generator 302 to the generator position. That is, the system 300 can be configured for EM field generator setup and tracking based on a plurality of EM sensors 204. Examples using based on a plurality of EM sensors 204 are provided with respect to FIGS. 35A-37.

Figure 35B:
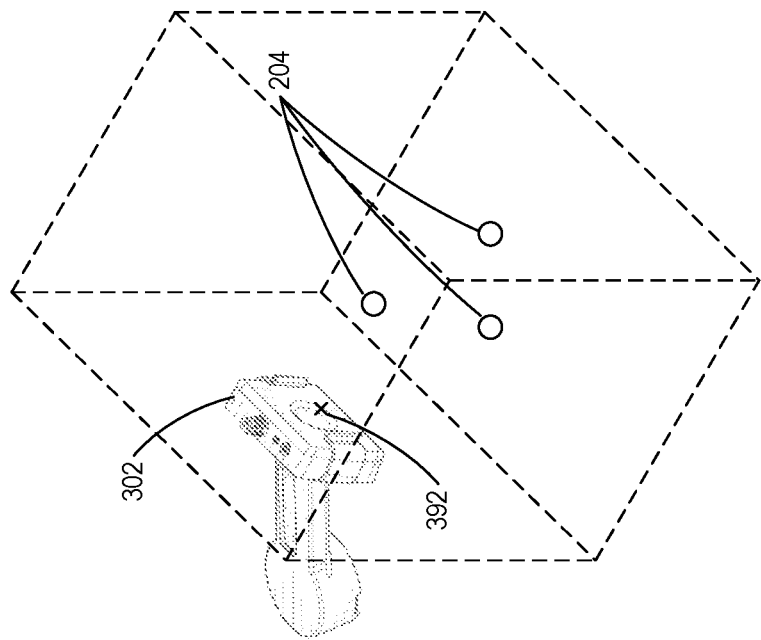
FIGS. 35A and 35B are perspective views that illustrate an example of moving an EM field generator to a field generator position using a robotic arm based on determined positions of a plurality of EM sensors within an EM field, according to an example embodiment.
Figure 35A:
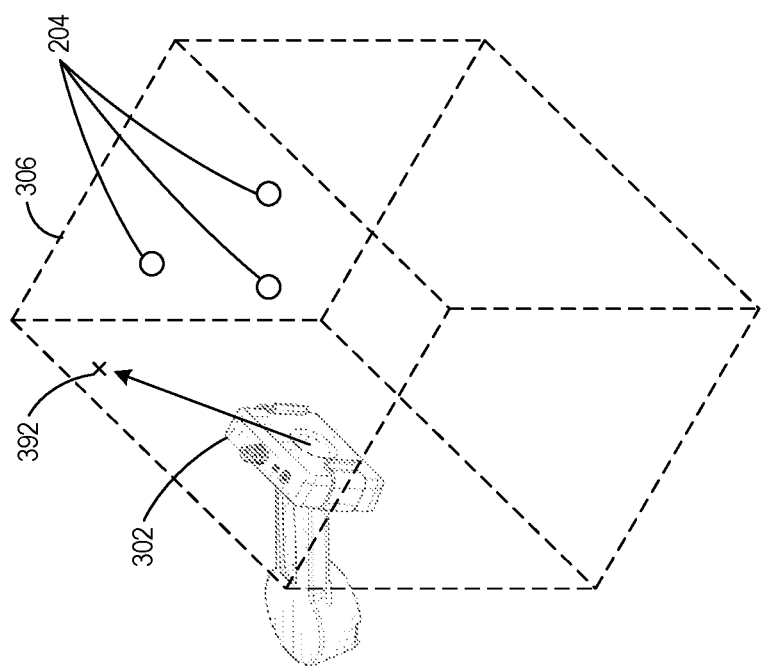

FIGS. 35A and 35B are perspective views that illustrate an example of moving an EM field generator 302 to a field generator position using a robotic arm 212 based on determined positions of a plurality of EM sensors 204 within an EM field. In some ways similar to earlier examples, this can occur during field generator setup and can advantageously be used to position the EM field generator 302 relative to the plurality of EM sensors 204.

FIG. 35A illustrates the system in a first state. As shown, in the first state, the plurality of EM sensors 204 are positioned within the working volume 306 of the EM field generator 302. However, as illustrated, the plurality of EM sensors 204 are not centered within the working volume 306. To center the plurality of EM sensors 204 within the working volume 306, a field generator position 392 can be determined. The field generator position 392 can represent a position to which the EM field generator 302 can be moved to center the plurality of EM sensors 204 within the working volume. In the illustrated embodiment, the generator position 392 is represented as an x. The EM field generator 302 must be moved in the direction of the arrow shown, causing a corresponding movement of the working volume 306, to arrive at the generator position 392.

The generator position 392 can be determined based on the determined positions of the plurality of EM sensors 302. In one example, the processor 380 is configured to determine the generator position 392 based on determining a centroid of the determined positions for the plurality of EM sensors 204. The generator position 392 can then be determined by finding the position to which the EM field generator 302 should be moved such that the centroid of the positions of the plurality of EM sensors 204 is positioned at a predetermined position (such as the center or other desired positions) within the working volume 306. As before, the determined positions of the plurality of EM sensors can be mapped into the robotic coordinate frame using the registration previously described based on the kinematics of the robotic arm 212 to which the EM field generator 302 is attached.

FIG. 35B illustrates the system in a second state, after adjusting the position of the EM field generator 302 to the generator position 392. As shown, the plurality of EM sensors 204 are now positioned closer to the center of the working volume 206. Accordingly, the system can facilitate setup and positioning of the EM field generator 302 relative to a plurality of EM sensors 204. Although this example has described "centering" the plurality of EM sensors 204 within the working volume 306, the generator position 392 can be determined to position the plurality of EM sensors at other locations within the working volume 306.

Figure 36B:
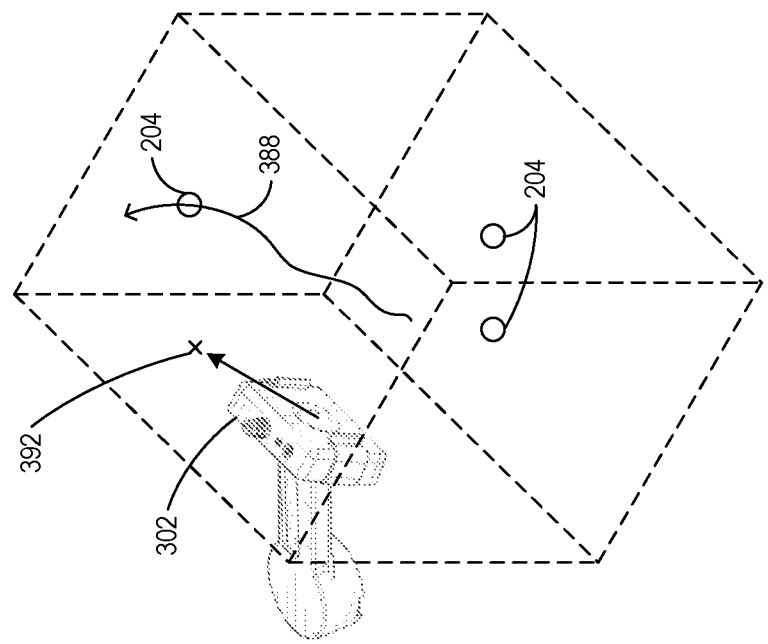
FIGS. 36A-36C are perspective views that illustrate an example of readjusting a field generator position of an EM field generator using a robotic arm based on the determined positions of a plurality of EM sensors within an EM field, wherein at least one of the plurality of EM sensors is moving, according to an example embodiment.
Figure 36A:
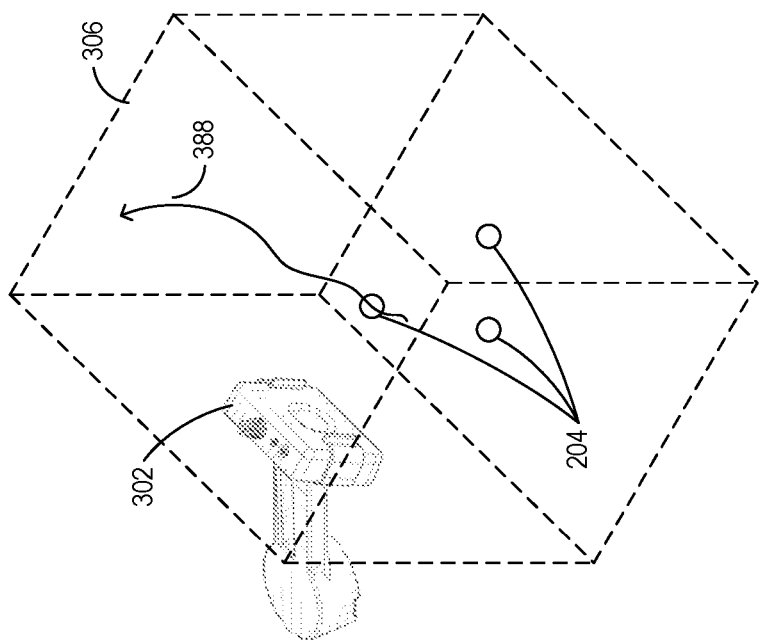
Figure 36C:
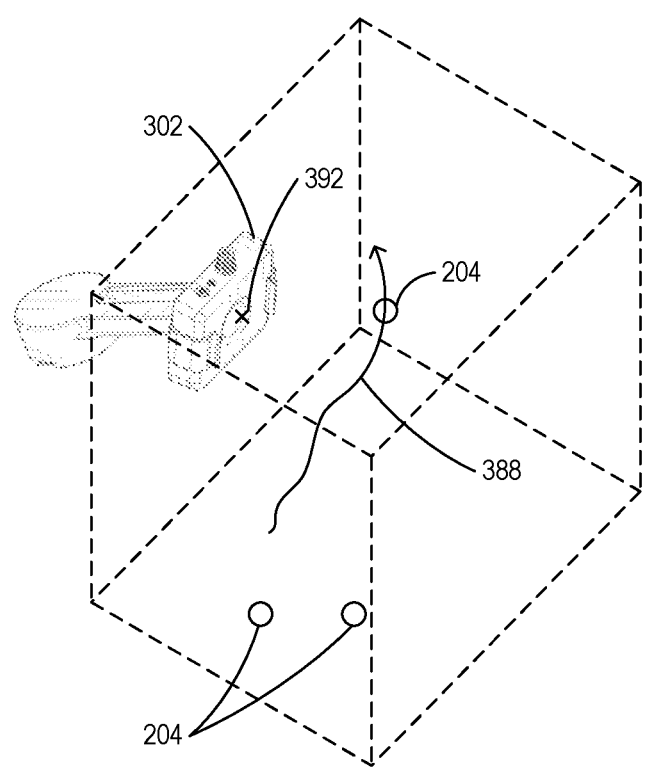

FIGS. 36A, 36B, and 36C are perspective views that illustrate an example of readjusting a field generator position 392 of the EM field generator 302 using a robotic arm 212 based on the determined positions of a plurality of EM sensors 204 within the working volume 306, wherein at least one of the plurality of EM sensors 204 is moving. For example, the processor 380 can be configured detect movement of at least one of the EM sensors 204, determine a new generator position 392 for the EM field generator 302 based on the detected movement, and command the first robotic arm 212 to move the EM field generator 302 to the new generator position 392.

As shown in FIG. 36A, one of the EM sensors 204 is moving along a path 388. It may be desirable to adjust the position of the field generator 302 based on this movement. For example, if not adjusted, the EM sensor 204 may move along the path to a location that falls outside of the working volume 306, at which point tracking of the EM sensor 204 would be lost.

Accordingly, as shown in FIG. 36B, a new field generator position 392 can be determined based on the positions of the plurality of EM sensors 204 and considering the movement of the one EM sensor 204 along the path 388. The new field generator position 392 can be, for example, based on a current centroid of the positions of the plurality of EM sensors 204. As shown, the EM field generator 302 would need to move in the direction of the illustrated arrow to reach the new generator position 392. FIG. 36C illustrates the system after movement to the new field generator position 392. As shown, the positions of the plurality of EM sensors 204 are now re-centered within the working volume 306. This can advantageously allow the position of the EM field generator 302 to be continually adjusted to optimize the position of the working volume 306 such that the positions of the plurality of EM sensors 204 remain positioned within the working volume 306 for as long as possible, even as they move away from each other.

Figure 37:
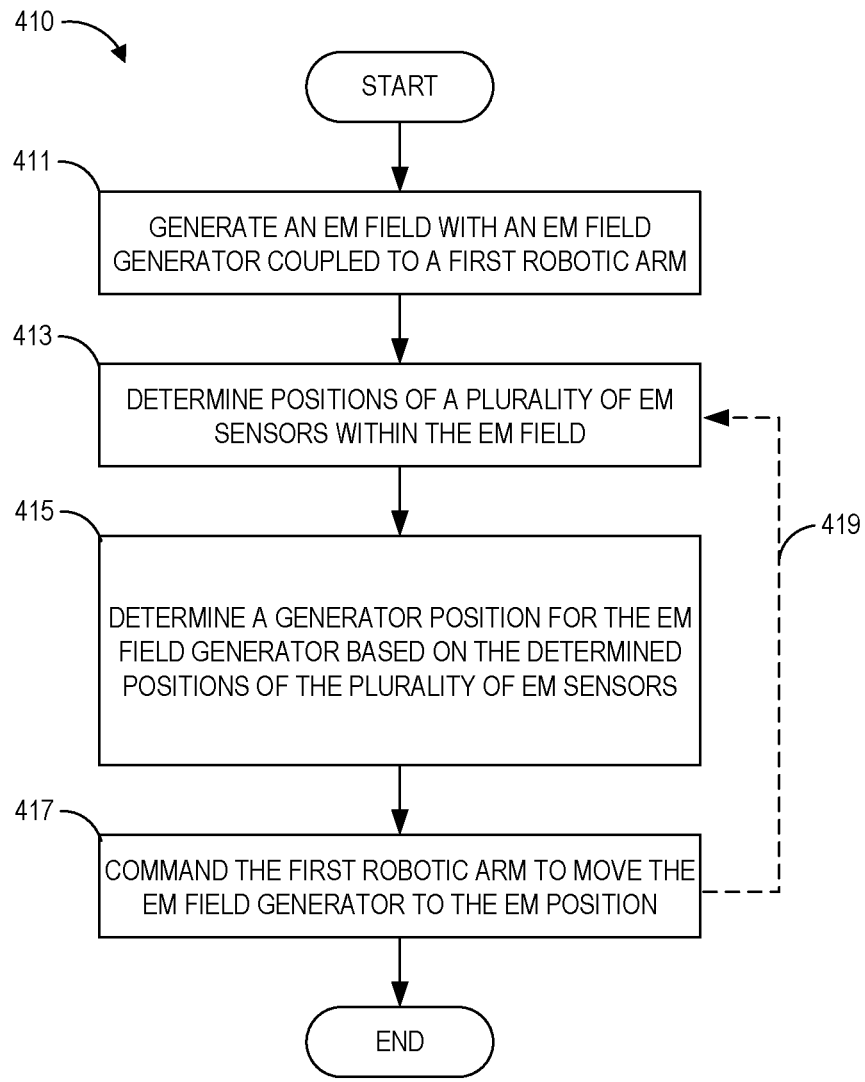
FIG. 37 is a flowchart illustrating an example method for determining a field generator position for an EM field generator mounted on a robotic arm based on determined positions of a plurality of EM sensors within an EM field, according to an example embodiment.

FIG. 37 is a flowchart illustrating an example method 410 for determining a field generator position for an EM field generator mounted on a robotic arm based on determined positions of a plurality of EM sensors within an EM field. The method 410 begins at block 411, which involves generating an EM field with an EM field generator coupled to a first robotic arm.

At block 413 of the method 410, embodiments may determine positions of a plurality of EM sensors within the EM field. This can be accomplished by determining the positions of the plurality of EM sensors within the EM field relative to an EM coordinate frame associated with EM field generator, determining a registration between the EM coordinate frame and a robotic coordinate frame associated with the first robotic arm based on determining a position of the EM field generator within the robotic coordinate frame, and, based on the registration, determining the positions of the plurality of EM sensors in the robotic coordinate frame. The determination of the position of the EM field generator within the robotic coordinate frame can be based on kinematics of the first robotic arm.

At block 415, the method 410 involves determining a generator position for the EM field generator based on the determined positions of the plurality of EM sensors. Determining the generator position can be based on determining centroid of the positions of the plurality of EM sensors 204. The EM field generator position can be a position that the EM field generator can be moved to that will desirably position the plurality of EM sensors within the working volume of the EM field.

Block 417 includes commanding the first robotic arm to move the EM field generator to the generator position. For example, the system can move the EM field generator to the generator position using the first robotic arm. As the EM field generator is moved, the position of the working volume is correspondingly repositioned relative to the positions of the EM sensors.

As illustrated by dashed line 419, the method 410 can be performed as a loop to continually adjust the position of the EM field generator as described above with reference to FIGS. 36A-36C. For example, the method 410 can also include detecting movement of at least one of the plurality of the EM sensors, determining a new generator position for the EM field generator based on the detected movement, and commanding the first robotic arm to move the EM field generator to the new generator position.

ii. Field Generator Setup and Instrument Tracking with an Expanded Working Volume In the previous section, robotic medical systems including robotically controllable field generators that can be moved with a robotic arm of the system to facilitate field generator setup and instrument tracking were discussed. In some of the examples, it was illustrated that the EM field generator could be moved with the robotic arm to track an EM sensor, for example, to keep a moving EM sensor within a working volume of the EM field generated by the EM field generator. By moving the EM field generator, and correspondingly the working volume of the EM field thereof, the systems described herein can be considered to have an "expanded" working volume. That is, by repositioning the EM field generator and the working volume, the positions of EM sensors can be detected and determined over an area that is larger than the working volume of a stationary field generator.

This section provides additional examples to elaborate on the concept of "expanding" the working volume of the EM field generator by moving the EM field generator with a robotic arm. In particular, the examples show, among other things, how EM sensors that are spaced too far apart to fit within the working volume of the EM field generator at the same time can be tracked by moving the EM field generator, detecting the positions of the EM sensors, and mapping the detected positions of the EM sensors into the robotic coordinate frame. This provides significant benefits over prior systems that utilize stationary field generators that may "lose track" of EM sensors once they are moved outside of the stationary working volume. The examples in this section with reference to the example system 300 of FIGS. 23 and 29, but may be implemented with other systems that include robotically controllable field generators as well.

Figure 38A:
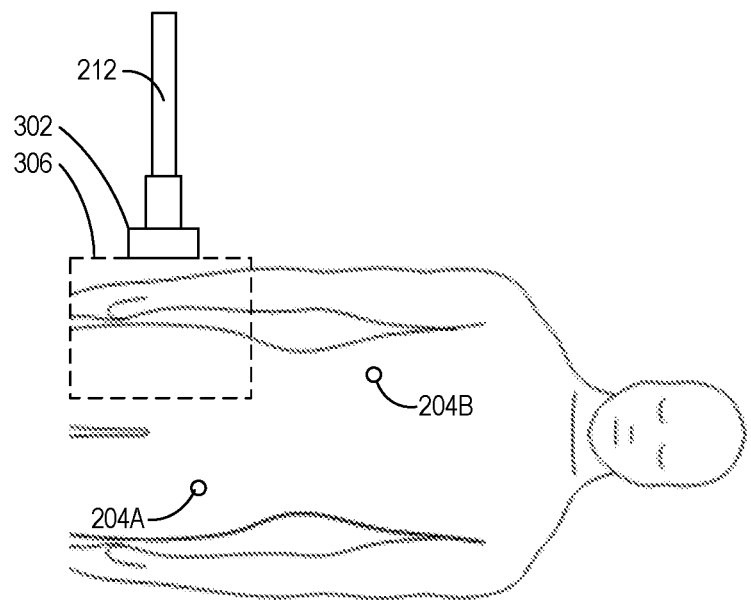
FIGS. 38A, 38B, and 38C illustrate an embodiment of a robotic medical system including a robotically controllable field generator that can be moved with a robotic arm to expand a working volume of the field generator, according to an example embodiment.

A first example will now be described with reference to FIGS. 38A-38C, which illustrate the system 300 at different stages to show how the system 300 expand the working volume 306 of the EM field generator 302. As shown in FIG. 38A, which illustrates some components of the system at a first stage, the system includes the EM field generator 302 that is configured to generate an EM field having a working volume 306 within which positions EM sensors 204 can be determined relative to an EM coordinate frame 308, as previously described. The EM field generator 302 is coupled to a robotic arm 212 that is configured to move to adjust the position of the EM field generator 302. As the robotic arm 212 moves the EM field generator 302, the position of the working volume 306 of the EM field generator 302 moves as well.

FIG. 38A also illustrates two EM sensors 204A and 204B. As shown, in the first stage, neither of the two EM sensors 204A, 204B are positioned within the working volume 306 of the field generator 302, and thus the positions of the EM sensors 204A, 204B are not determinable in the first stage. Further, the two EM sensors 204A, 204B are positioned sufficiently far apart that both cannot be positioned within the working volume 306 at the same time. Thus, as will be shown in FIGS. 38B and 38C, in order to track the positions of the EM sensors 204A, 204B, the EM field generator 302 can be moved, using the robotic arm 212, to different positions at which each of the EM sensors 204A, 204B can be determined and mapped into the robotic coordinate frame 216 in order to "expand" the working volume 306 of the EM field generator.

For example, the processor 380 of the system 300, which is in communication with the EM field generator 302 and the robotic arm 212 to which the EM field generator 302 is attached, can be configured to move the EM field generator 302 to a first position at which the EM sensor 204 is positioned within the working volume 306. With the EM field generator 302 in the first position, the processor 380 can determine the position of the first EM sensor 204A within the working volume 306 relative to the EM coordinate frame 308, and map the position of the first EM sensor 204A into the robotic coordinate frame 216 based on the kinematics of the robotic arm with the EM field generator 302 in the first position. The processor 380 can then cause the robotic arm 212 to move the EM field generator 302 to a second position at which the second EM sensor 204B is positioned within the working volume. And, with the EM field generator 302 in the second position, the processor 380 can determine the position of the second EM sensor 204B within the working volume 306 relative to the EM coordinate frame 308, and map the position of the second EM sensor 204B into the robotic coordinate frame 216 based on the kinematics of the robotic arm 212 with the EM field generator 302 in the second position. In this way, the positions of both EM sensors 204A, 204B can be presented within the robotic coordinate frame 216.

Figure 38B:
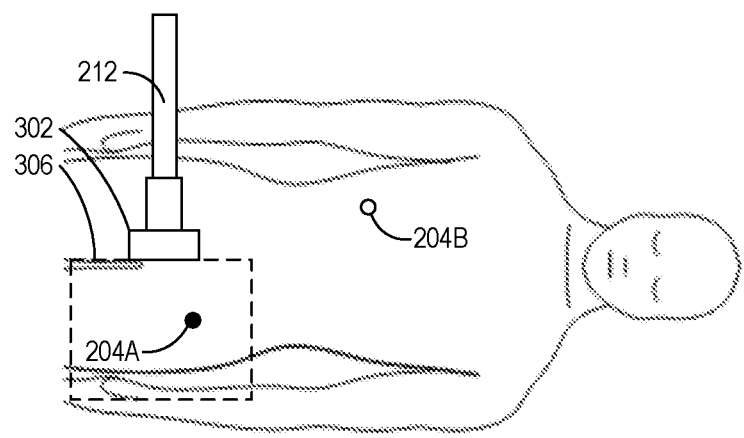

FIG. 38B illustrates the system in an example second stage, wherein the EM field generator 302 has been moved with the robotic arm 212 to the first position at which the first EM sensor 204A is positioned within the working volume 306. With the EM field generator 302 in this position, the position of the EM sensor 204A can be determined relative to the EM coordinate frame 308, and that position can then be mapped to the robotic coordinate frame 216 using the registration based on the kinematics of the robotic arm 212 previously described. In FIG. 38B, the EM sensor 204A has been shaded in black to indicate that its position, while initially determined in the EM coordinate frame 308, has been mapped to the robotic coordinate frame 216.

Figure 38C:
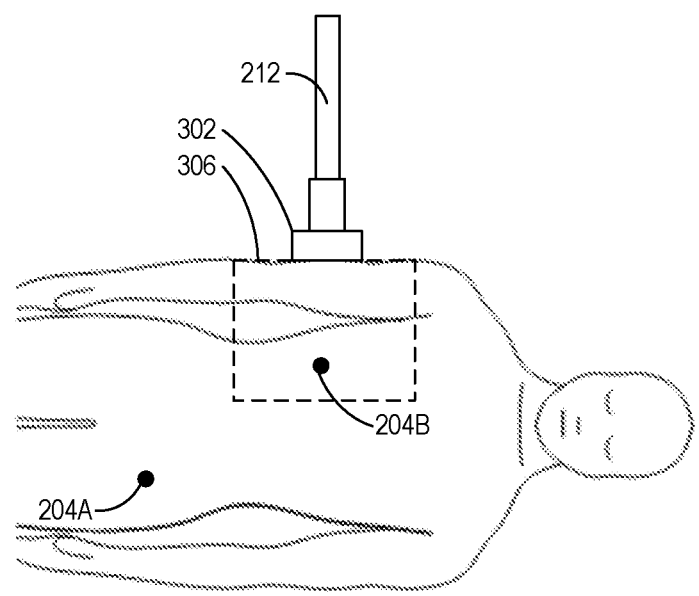

FIG. 38C illustrate the system in an example third stage, wherein the EM field generator 302 has been moved with the robotic arm 212 to the second position at which the second EM sensor 204B is positioned within the working volume 306. With the EM field generator 302 in this position, the position of the EM sensor 204B can be determined relative to the EM coordinate frame 308, and that position can then be mapped to the robotic coordinate frame 216 using the registration based on the kinematics of the robotic arm 212 previously described. As before, the EM sensor 204B has been shaded in black to indicate that its position has been mapped into the robotic coordinate frame 216. The EM sensor 204A is also still shaded black to indicate its position within the robotic coordinate frame 216.

Considering FIG. 38C, one can see that the positions of both EM sensors 204A, 204B can be simultaneously or substantially concurrently represented within the robotic coordinate frame 216, even though the EM sensors 204A, 204B are spaced sufficiently far apart that they both cannot fit within the working volume 306 of the EM field generator 302 at the same time. In some embodiments, the processor 380 is further configured to move the EM field generator 302 back and forth between the first position and the second position to frequently update (e.g., at about 40 Hz, or time steps both smaller and larger) and track the positions of the first and second EM sensors 204A, 204B.

Further, the example described with reference to FIGS. 38A-38C has been presented simplistically describing the EM field generator 302 in a first position (FIG. 38B) and a second position (FIG. 38C). In actuality, the system can be configured to continuously or near continuously, detect any EM sensors 204 positioned within the EM field and map those positions into the robotic coordinate frame 216. For example, the processor 380 can be configured to move the EM field generator 302 using the robotic arm 212, and when an EM sensor is detected within the working volume 306, the processor 380 can be configured to (i) determine the position of the EM sensor 204 within the working volume 306 relative to the EM coordinate frame 308, and (ii) map the position of the EM sensor 204 into the robotic coordinate frame 216 based on a kinematic pose of first robotic arm 212.

In some instances, the initial positions of the EM sensors 204 may not be known. To locate the EM sensors 204, the system can be configured to move the EM field generator 302 using the robotic arm 212 along a searching path or trajectory (e.g., along a predetermined path/pattern or range of motions). The searching path can be configured to sweep the working volume 306 through a treatment volume larger than the working volume 306 to locate EM sensors within the treatment volume. By sweeping through the treatment volume, the initial positions of any EM sensors 204 within the treatment volume can be determined.

Figure 39A:
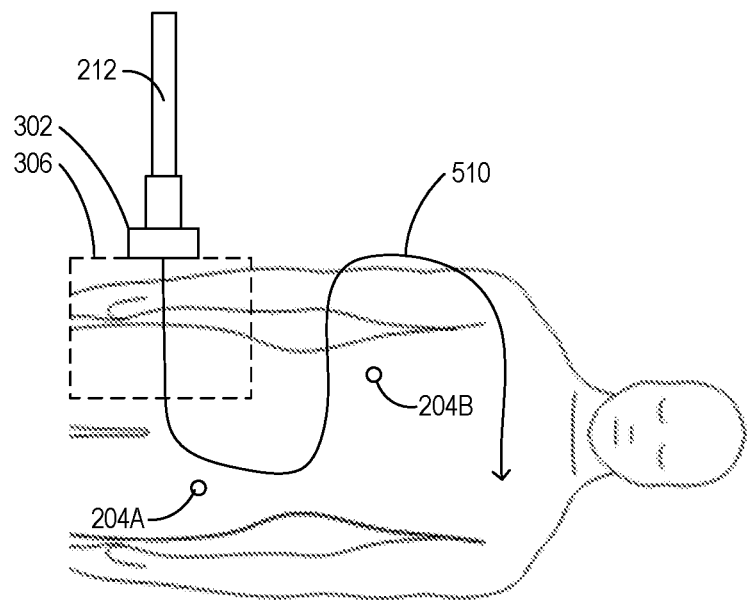
FIGS. 39A-39D illustrate an embodiment of a robotic medical system including a robotically controllable field generator that can be moved with a robotic arm to detect positions of EM sensors and expand a working volume of the field generator, according to an example embodiment.

FIGS. 39A-39D illustrate an embodiment of the robotic medical system including a robotically controllable field generator 302 that can be moved with the robotic arm 212 along a searching path 510 to detect positions of EM sensors 204. In the example of FIG. 39A, the initial positions of two EM sensors 204A, 204B are not known. In an effort to identify the positions of the EM sensors 204A, 204B, FIG. 39A illustrates an example searching path 510 along which the EM field generator 302 will be moved using the robotic arm 212. In the illustrated embodiment, the searching path 510 comprises a generally sinusoidal path configured to sweep the working volume 306 across the treatment volume or treatment site in which EM sensors 204 are expected. The searching path 510 illustrated in FIG. 39A is provided by way of example, and any number of paths comprising different shapes are possible.

Figure 39B:
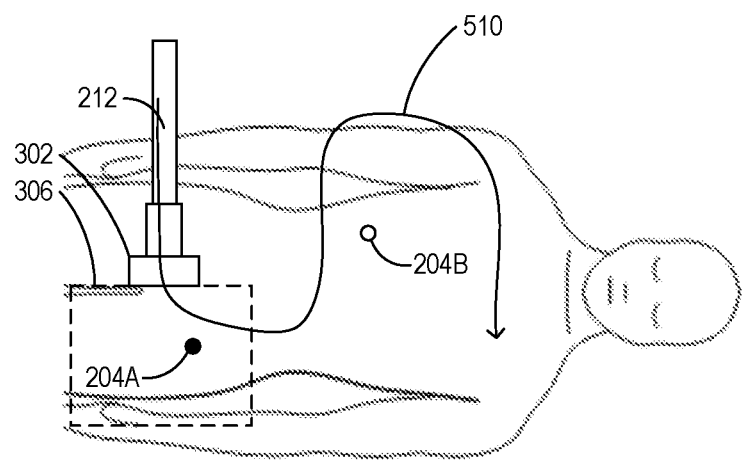

FIG. 39B illustrates the system at a second stage, as the EM field generator 302 is moved along the searching path 510. At the second stage illustrated in FIG. 39B, the first EM sensor 204A is now positioned and detectable within the working volume 306 of the EM field generator 302. The position of the EM sensor 204A can be determined relative to the EM coordinate frame 308, and that position can then be mapped to the robotic coordinate frame 216 using the registration based on the kinematics of the robotic arm 212 previously described. In FIG. 39B, the EM sensor 204A has been shaded in black to indicate that its position, while initially determined in the EM coordinate frame 308, has been mapped to the robotic coordinate frame 216. The EM field generator 302 can continue along the searching path 510.

Figure 39C:
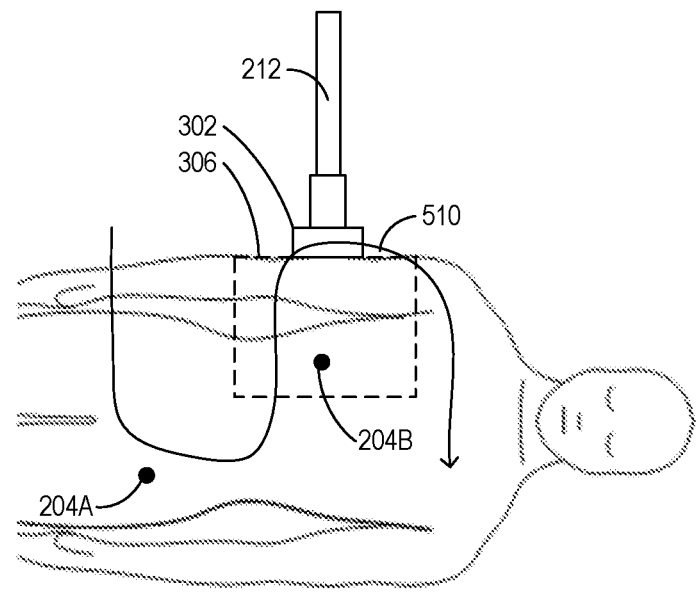

FIG. 39C illustrates the system at a third stage, as the EM field generator 302 is moved even further along the searching path 510. At the third stage illustrated in FIG. 39C, the second EM sensor 204B is now positioned and detectable within the working volume 306 of the EM field generator 302. The position of the EM sensor 204B can be determined relative to the EM coordinate frame 308, and that position can then be mapped to the robotic coordinate frame 216 using the registration based on the kinematics of the robotic arm 212 previously described. In FIG. 39B, the EM sensor 204B has been shaded in black to indicate that it has been mapped to the robotic coordinate frame 216. The EM field generator 302 can continue along the searching path 510. The position of the EM sensor 204A is also shown, shaded in black, to represent its position mapped into the robotic coordinate frame.

Figure 39D:
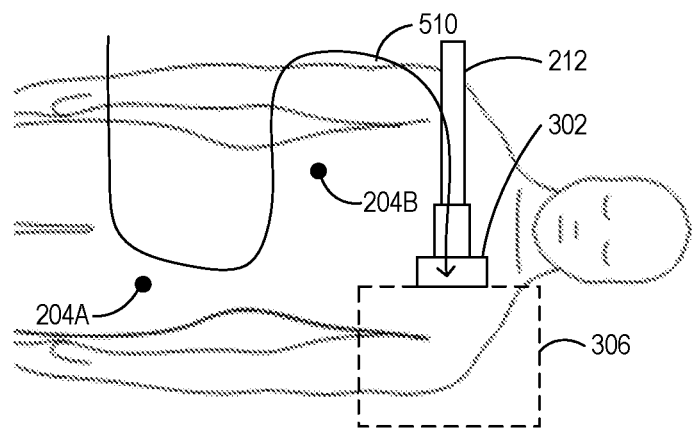

FIG. 39D illustrates the system at a fourth stage at which the EM field generator 302 has completed the searching path 510. As show, the positions of all EM sensors 204 (in the illustrated example, the EM sensors 204A, 204B) have been identified and mapped into the robotic coordinate frame 216. In some embodiments, the system is configured to follow a searching path 510 at the beginning of the procedure to identify the positions of EM sensors 204. The searching path 510 can be periodically repeated to determine whether any new EM sensors 204 have been introduced.

In some embodiments, the initial positions of the EM sensors 204 can be determined in other ways. For example, when an EM sensor 204 is included on a robotically controllable instrument, the system may estimate or determine the initial position of the EM sensor 204 based on the kinematics of the robot. For EM sensors 204 that are not coupled to robotic components of the system, in some embodiments, a user may indicate or input the initial positions of the EM sensors 204 to the system (e.g., via a user input device, controller, graphical user interface, etc.). For example, in the case of an EM patch sensor placed on a patient's chest to track respiration, the user placing the EM patch sensor may indicate where the patch sensor has been placed to the system.

As noted above, in some instances, the mapped positions of the EM sensors 204 into the robotic coordinate frame 216 may not represent live positions of the sensors. Accordingly, after the initial positions of the EM sensors are determined, the system may determine a new tracking path along which the EM field generator 302 can be moved in order to continue tracking the positions of the EM sensors 204. The tracking path may, for example, be shorter than the searching path, which can allow for faster or more frequent remapping of the positions of the EM sensors 204. An example is described with reference to FIGS. 40A-40D.

FIGS. 40A-40D continue the example of FIGS. 39A-39D and further illustrate an example tracking path 512 for the EM field generator 302. The tracking path 512 can be determined based on the determined positions of the EM sensors 204 within the robotic coordinate frame 216. For example, the tracking path 512 can be determined such that the EM field generator 302 is moved back and forth between determined positions of the EM sensors 204 within the robotic coordinate frame 216 so that the positions can be frequently remapped and updated frequently. For example, as the EM field generator 302 is moved along the tracking path using the robotic arm 212, the processor 380 can be configured to (i) re-determine the positions of the EM sensors 204 within the working volume 306 relative to the EM coordinate frame 308, (ii) re-map the positions of the EM sensors 204 into the robotic coordinate frame 216 based on the kinematic pose of the robotic arm 212, and (iii) determine an updated tracking path 510.

Figure 40A:
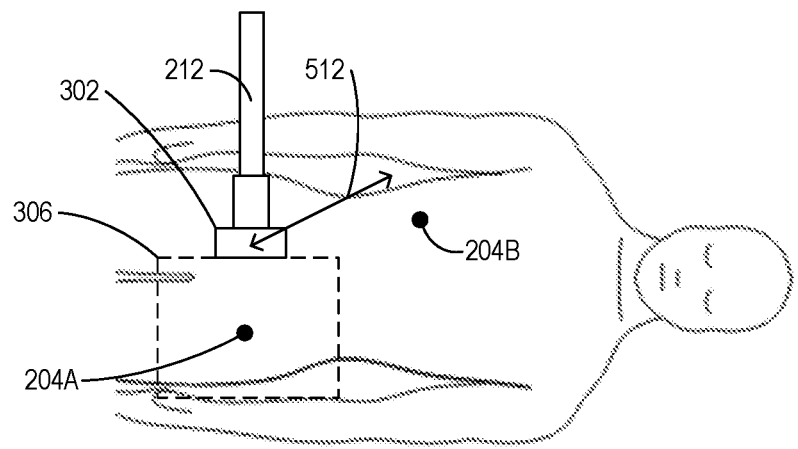
FIGS. 40A-40D illustrate an embodiment of a robotic medical system including a robotically controllable field generator that can be moved with a robotic arm to track positions of EM sensors within an expanded working volume of the field generator, according to an example embodiment.

As shown in FIG. 40A, the tracking path 512 can be shorter than the searching path 510 (of FIGS. 39A-39D). This can be advantageous as it can limit unnecessary movement of the EM field generator (which might cause collisions with other objects in the space) and limits the time at which no EM sensors are positioned within the working volume 306. In the illustrated embodiment, the tracking path 512 comprises a line that moves the EM field generator 302 back and forth between positions at which each of the EM sensors 204A, 204B can be detected within the working volume 306 and remapped into the robotic coordinate frame 216. Other shapes for the tracking path 512 are also possible.

Figure 40B:
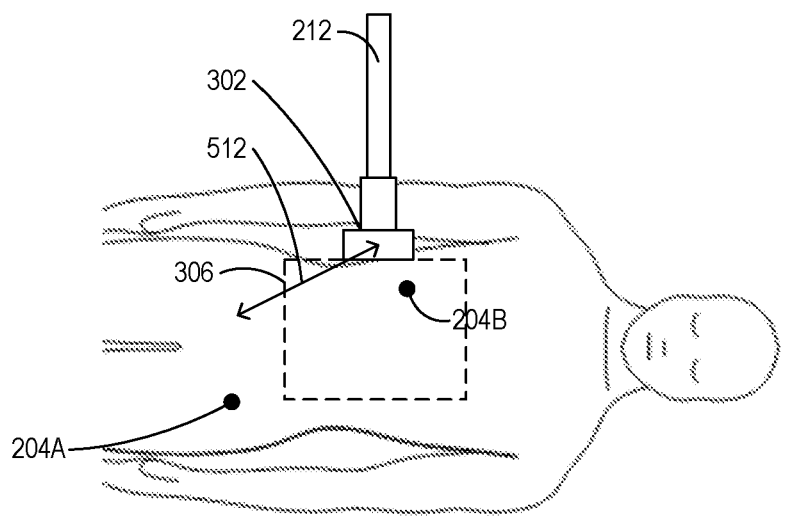

FIG. 40A illustrates the EM field generator 302 positioned at a first end of the tracking path 512 at which the first EM sensor 204A is positioned within the working volume 306. In this position, the position of the first EM sensor 204A can be detected relative to the EM coordinate frame 308 and remapped into the robotic coordinate frame 216. FIG. 40B illustrates the EM field generator 302 positioned at a second end of the tracking path 512 at which the second EM sensor 204B is positioned within the working volume 306. In this position, the position of the second EM sensor 204B can be detected relative to the EM coordinate frame 308 and remapped into the robotic coordinate frame 216. In FIGS. 40A and 40B, the EM sensors 204A, 204B are shaded in black to represent that their positions have been mapped into the robotic coordinate frame 216 (e.g., when detected as the EM field generator 302 moves along the searching path 510 as described in the previous example of FIGS. 39A-39D).

Figure 40C:
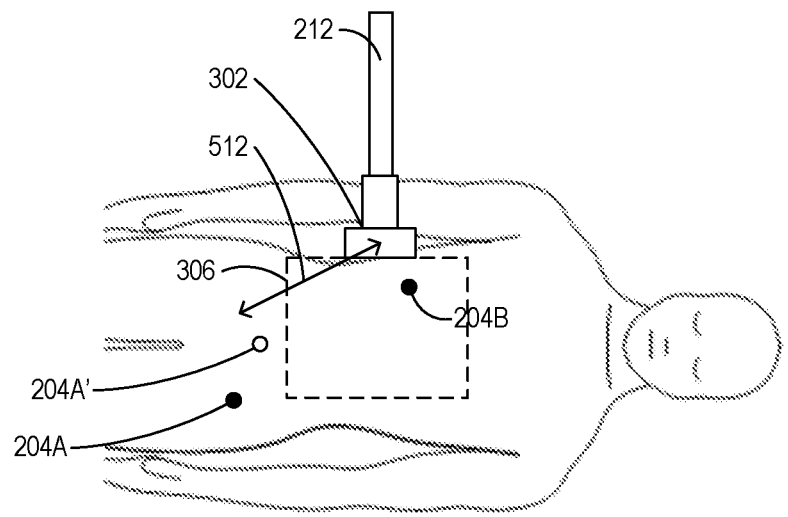

FIG. 40C illustrates how the mapped position of the EM sensor 204A into the robotic coordinate frame may not be live. For example, as shown in FIG. 40C, while the EM field generator 302 is positioned at the second end of the tracking path 512 such that the first EM sensor 204A is not positioned within the working volume 306, the first EM sensor 204A can be moved to a new position indicated as EM sensor 204A'. Notably, the previous mapped position of the EM sensor 204A is still shown (shaded in black). In this position, the system has not yet determined that the EM sensor 204A has moved to the new position of the EM sensor 204A'. In some embodiments, each sensor 204 is connected to a dedicated port of the system, such that the system can identify and distinguish between the sensors. Other mechanisms and methods for distinguishing between the sensors are also possible as well.

Figure 40D:
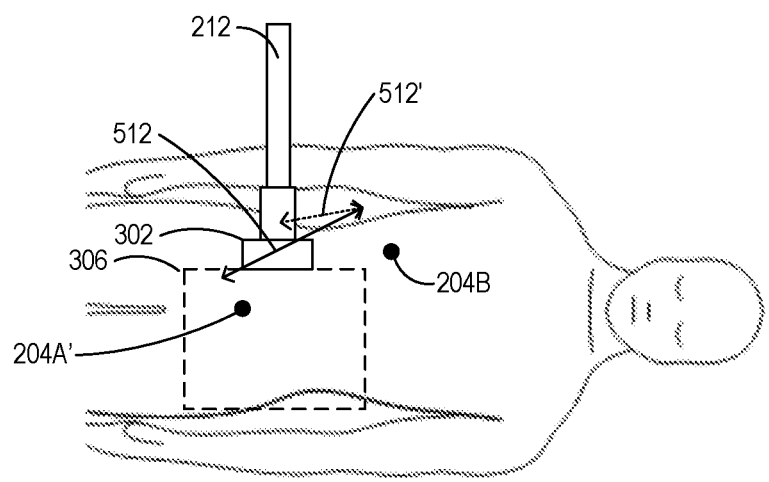

However, FIG. 40D illustrates that, as the EM field generator 302 is moved back to along the tracking path 512, it can detect the new position of the EM sensor 204A'. In this position, the new position of the first EM sensor 204A' can be detected relative to the EM coordinate frame 308 and remapped into the robotic coordinate frame 216. To indicate that the new position of the EM sensor 204A' has been remapped to the robotic coordinate frame 216, it has been shade in black in FIG. 40D.

FIG. 40D also illustrates that a new tracking path 512' can be determined based on the new position of the EM sensor 204A'. Accordingly, as EM sensors 204 are moved, the new positions of the EM sensors 204 can be remapped into the robotic coordinate frame 216 and an updated tracking path 512' can be determined. This process can repeat throughout the procedure to beneficially allow tracking of various EM sensors 204 within an expanded working volume that is made possible by moving the EM field generator 302 with the robotic arm 212 and mapping the positions of detected EM sensors 204 into the robotic coordinate frame based on the kinematic pose of the robotic arm 212.

Figure 41A:
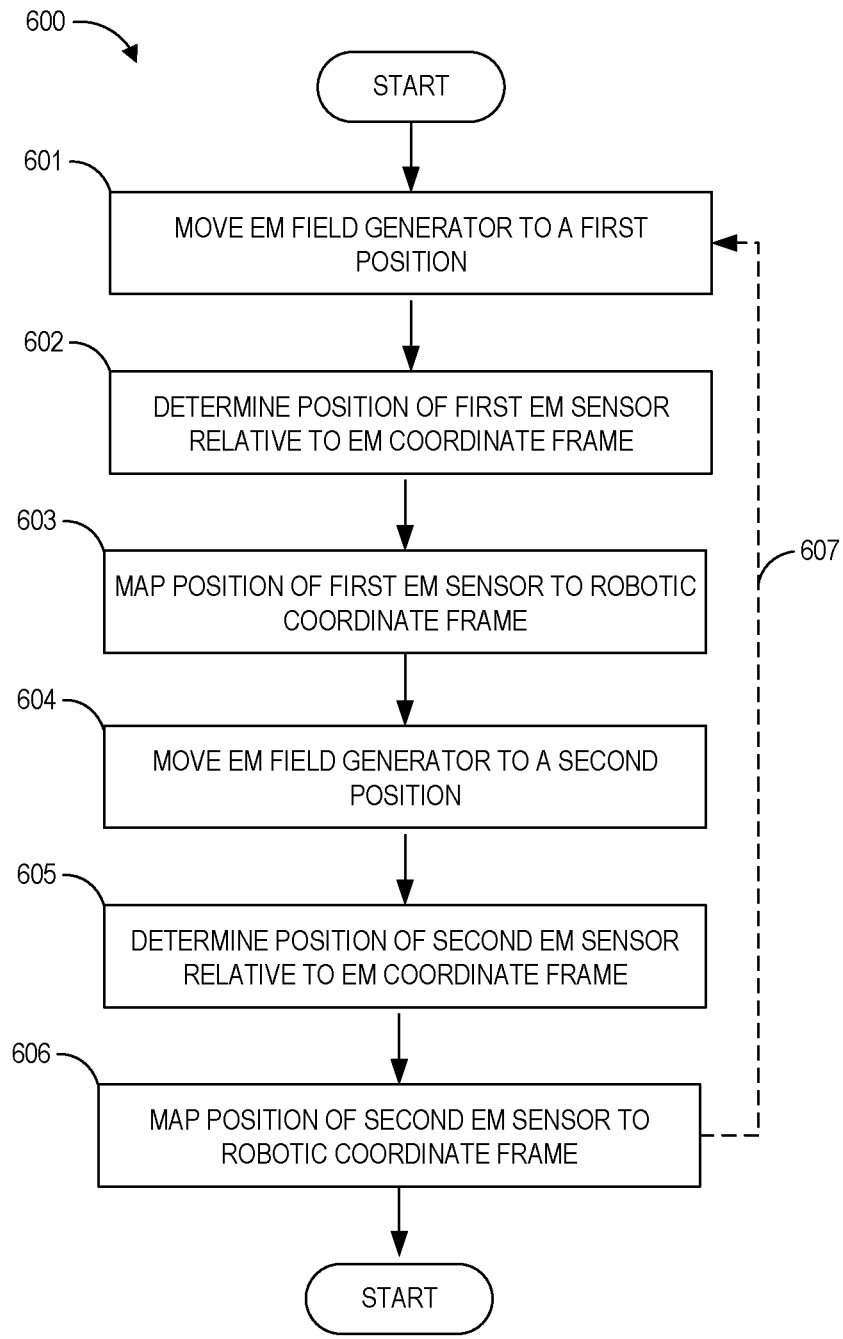
FIG. 41A is a flowchart illustrating an example method for expanding a working volume of a robotically controllable field generator, according to an example embodiment.

FIG. 41A is a flowchart illustrating an example method 600 for expanding a working volume of a robotically controllable field generator. The method 600 can be used, for example, to implement the functionality described above with reference to FIGS. 38A-38C. The method 600 begins at block 601, at which the EM field generator is moved to a first position. The first position can be a position at which an EM sensor is detected within the working volume of the EM field generator. The EM field generator can be moved using the robotic arm to which it is attached. In some embodiments, moving the EM field generator to the first position comprises moving the EM field generator along a searching or tracking path.

The method proceeds to block 602. At block 602, the position of the first EM sensor is determined relative to the EM coordinate frame. The EM coordinate frame is associated with the EM field of the EM field generator. Next, at block 603, the position of the EM sensor within the EM coordinate frame (determined at block 602) is mapped to a robotic coordinate frame. The robotic coordinate frame is associated with, for example, the robotic arm to which the EM field generator is coupled and the other robotic components of the system. Mapping the position of the EM sensor into the robotic coordinate frame can be based on the kinematic pose of the first robotic arm, which as noted previously, establishes a relationship between the EM coordinate frame and the robotic coordinate frame since the EM field generator is coupled to the robotic arm.

The method 600 can then proceed to block 604. At block 604, the EM field generator is moved to a second position at which a second EM sensor is detected within the working volume. As before, the EM field generator can be moved to the second position using the robotic arm to which it is attached. At block 605, the position of the second EM sensor can be determined relative to the EM coordinate frame. Next, at block 606, the position of the second EM sensor within the EM coordinate frame (determined at block 605) is mapped to a robotic coordinate frame, again using the registration based on the kinematics of the robotic arm. Finally, line 607 illustrates that the method 600 can be performed as a loop to continually re-detect and re-map the positions of the first and second EM sensors into the robotic coordinate frame.

Figure 41B:
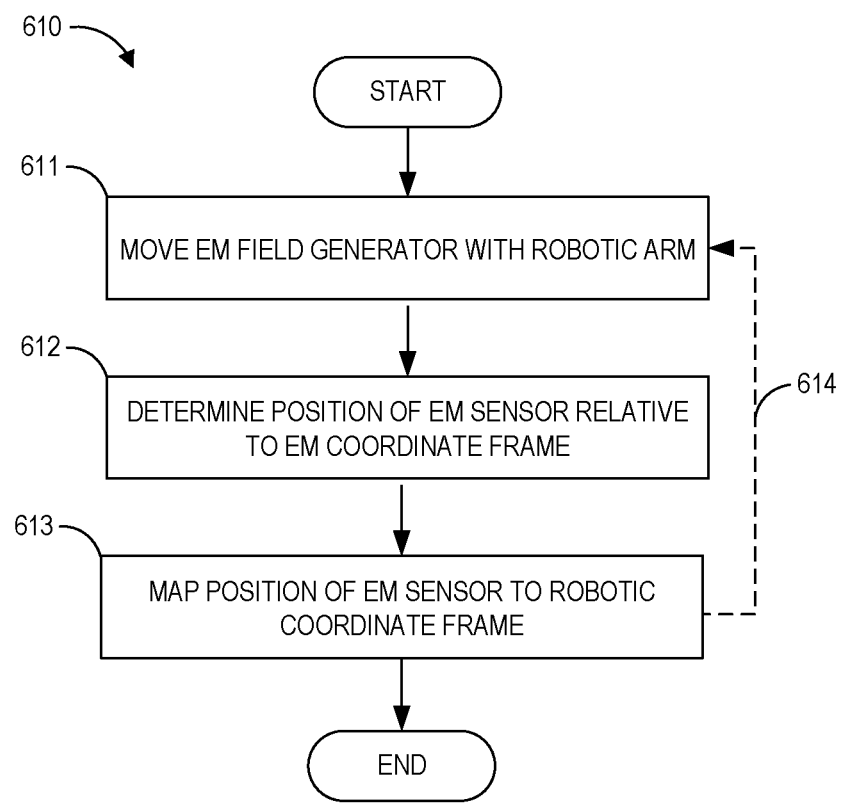
FIG. 41B is a flowchart illustrating another example method for expanding a working volume of a robotically controllable field generator, according to an example embodiment.

FIG. 41B is a flowchart illustrating another example method 610 for expanding a working volume of a robotically controllable field generator. The method 610 begins at block 611, which involves moving an EM field generator with a robotic arm to which it is attached. At block 612, whenever an EM sensor is detected within the working volume of the EM field generator, the position of the EM sensor can be determined relative to the EM coordinate frame. At block 613, the position of the EM sensor can be mapped to the robotic coordinate frame. The mapping can be based on the kinematics of the robotic arm as described previously. Finally, line 614 illustrates that the method 610 can be performed as a loop to continually re-detect and re-map the positions of the first and second EM sensors into the robotic coordinate frame.

iii. Alignment of Percutaneously Insertable Instrument with an EM Target

The robotically controllable EM field generator 302 may also facilitate alignment of percutaneously inserted tools with other tools endoscopically inserted into the body. For example, as shown in FIG. 27B, the ureteroscope 502 can be guided endoscopically to a position within the kidney. The operator may then desire to make a percutaneous insertion of or with a needle (or other instrument) so as to rendezvous with the ureteroscope 502. In some embodiments, the EM field generator 302 can include a needle guide (e.g., a channel, tube, or other structure) through which a needle (or other instrument) can be inserted. In other embodiment, the EM field generator 302 can define a space through which the needle guide or the like may be advanced and/or positioned. For example, the needle guide can be configured such that it allows for only one degree of freedom (insertion and/or retraction) for needles inserted therethrough. The EM field generator 302 can be align with the EM sensor 204 on the ureteroscope, such that when the needle is inserted through the needle guide, it is guided directly toward the EM sensor 204. One such use-case is in percutaneous procedures where access to the inner organs or other tissue is done via needle-puncture of the skin. A needle that is rigidly attached to the robot end effector and has a known transformation (rigid-body-definition) with respect to the robot end effector, thus can be robotically aligned with an EM beacon (target) inside the patient's body. The needle can then be inserted through the skin along the robotically-aligned trajectory.

Figure 42A:
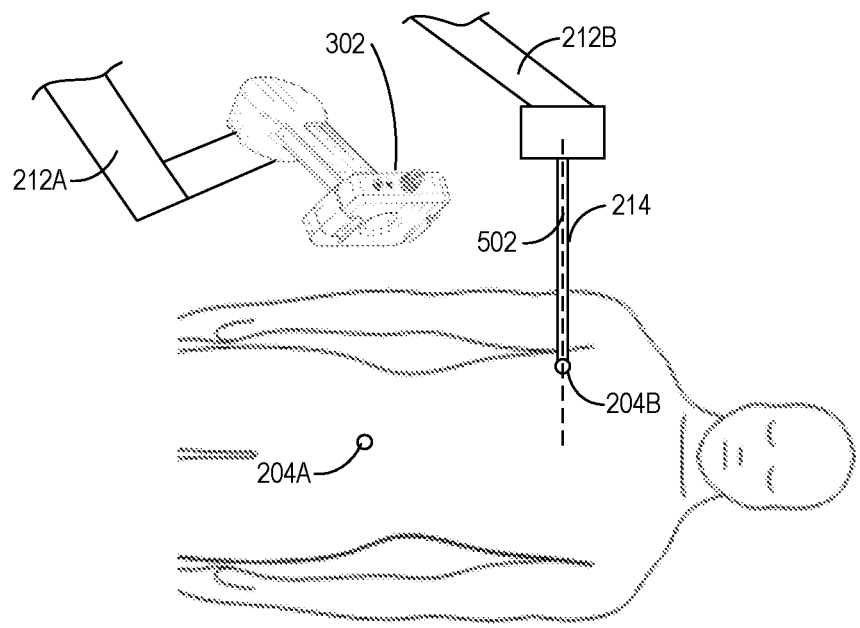
FIGS. 42A-42C illustrate an embodiment of a robotic medical system with a robotically controllable field generator configured to facilitate alignment of a percutaneously insertable instrument with an EM target, according to an example embodiment.
Figure 42B:
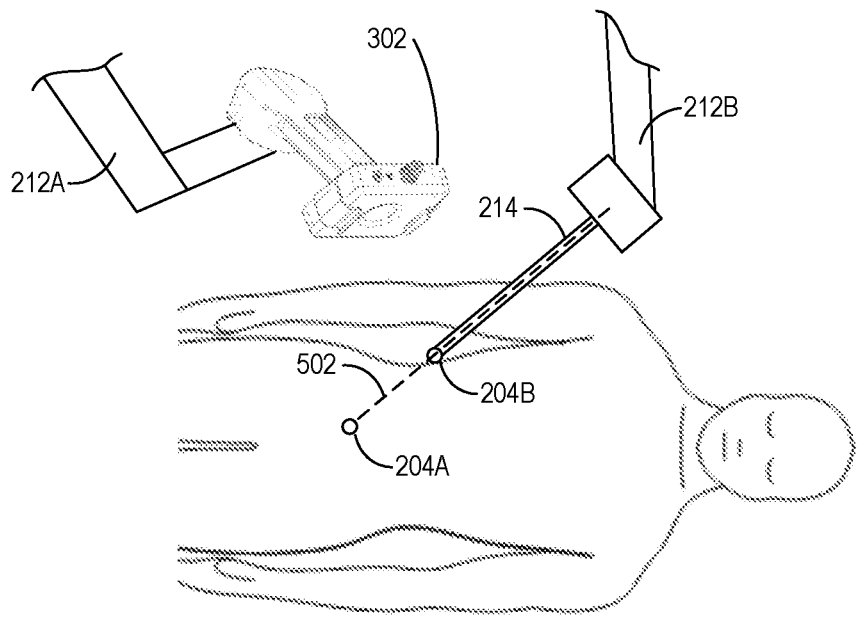
Figure 42C:
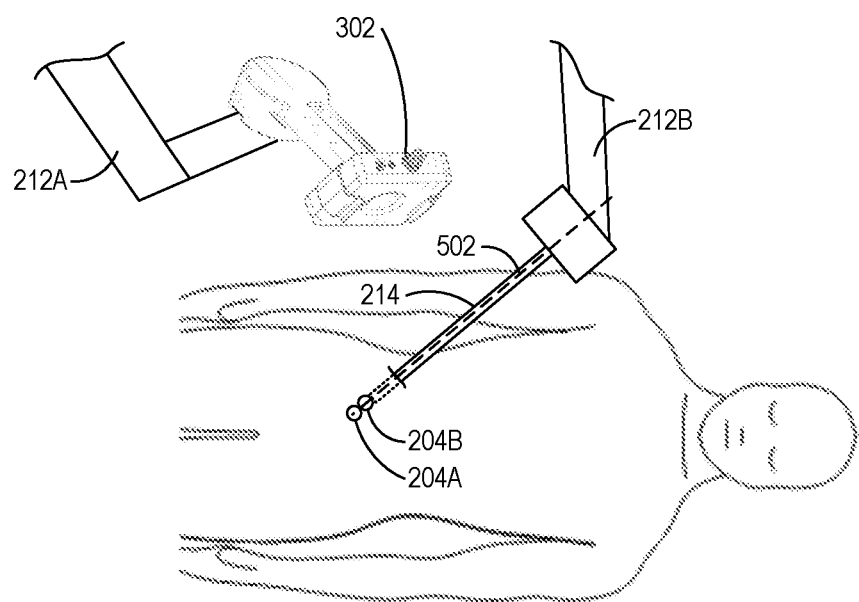

FIGS. 42A-42C illustrate an embodiment of a robotic medical system, such as the system 300 of FIGS. 23 and 29, with a robotically controllable field generator 302 configured to facilitate alignment of a percutaneously insertable instrument 214 with an EM target 204A. The percutaneously insertable instrument 214 can comprise, for example, a needle, an access sheath, a laparoscopic instrument, or other type of percutaneously insertable instrument. In the example of FIGS. 42A-42C it may be desired to precisely insert the percutaneously insertable instrument 214 into the body at a specific location. To facilitate percutaneous insertion, an EM target 204A (which can be an EM sensor) can be placed within the body at the desired position for the percutaneously insertable instrument 214. In some embodiments, the percutaneously insertable instrument 214 can also include an EM sensor 204B positioned thereon.

In the illustrated embodiment of FIG. 42A, the percutaneously insertable instrument 214 can be a robotically controllable instrument. The percutaneously insertable instrument 214 is shown attached to a second robotic arm 212B that is configured to position and insert the percutaneously insertable instrument 214. As shown, the percutaneously insertable instrument 214 extends along an axis 502. Generally, it is desirable to insert the percutaneously insertable instrument 214 along the axis 502. However, in order to insert the percutaneously insertable instrument 214 accurately, the axis 502 must be aligned with the EM target 204A.

Accordingly, the processor 380 of the system can be configured to determine a registration that maps positions within an EM coordinate frame associated with the EM field generator 302 to positions within a robotic coordinate frame 216 based on a kinematic pose of the first robotic arm 212A, to which the EM field generator 302 is attached. The processor 380 can further be configured to determine, based on the registration, a position of the EM target 204A within the robotic coordinate frame 216, and, based on the position of the EM target 204A within the robotic coordinate frame 216, the processor can be configured to move the second robotic arm 212B to align the axis 502 of the percutaneously insertable instrument 214 with the EM target Finally, the processor 380 can be configured to insertion of the percutaneously insertable instrument 214 along the axis 502 towards the EM target 204A using the second robotic arm 212B.

As described previously, the registration can be determined based on the position of the EM field generator 302 within the robotic coordinate frame 216, and the position of the EM field generator with the robotic coordinate frame 216 can be determined based on the kinematic pose of the first robotic arm 212A. The processor 380 can further be configured to determine the position of the EM target 204A within the robotic coordinate frame 216 by determining a position of the EM target 204A within the EM coordinate frame 308, and mapping, using the registration, the position of the EM target 204A within the EM coordinate frame 308 to the position of the EM target 204A within the robotic coordinate frame 216.

In some embodiments, the EM target 204A can be an EM sensor positioned on another robotic medical instrument configured for insertion into the patient, such as an endoscope navigated through the body. This robotic medical instrument can be coupled to a third robotic arm that is configured to control the robotic medical instrument;

FIG. 42A illustrates the system in a first state, wherein the axis 502 of the percutaneously insertable instrument 214 is not aligned with the EM target 204A. FIG. 42B illustrates the system in a second state, after alignment of the axis 502 with the EM target 204A. FIG. 42C illustrates the system in a third state, showing insertion of the percutaneously insertable instrument 214 along the axis 502 and rendezvous with the EM target 204A.

Figure 43A:
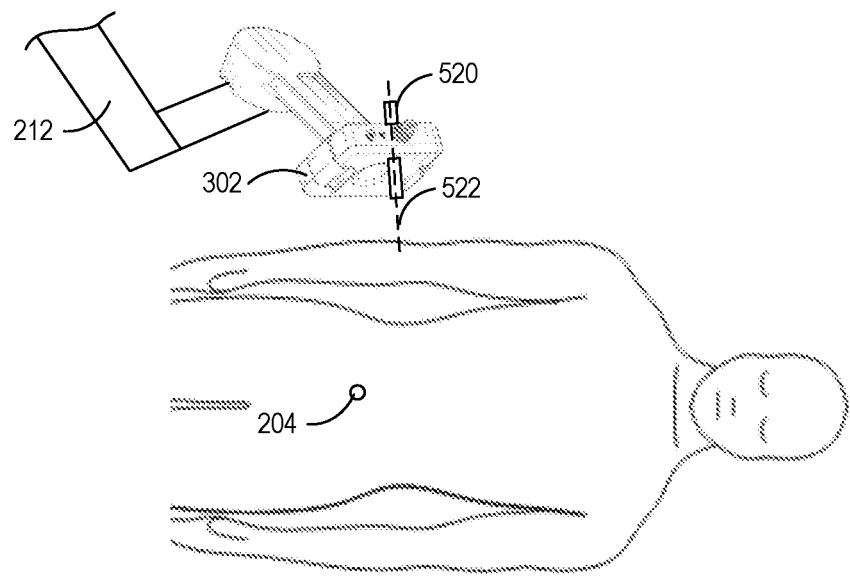
FIGS. 43A and 43B illustrate an embodiment of a robotic medical system with a robotically controllable field generator configured to facilitate alignment of an instrument guide mounted on the field generator with an EM target, according to an example embodiment.
Figure 43B:
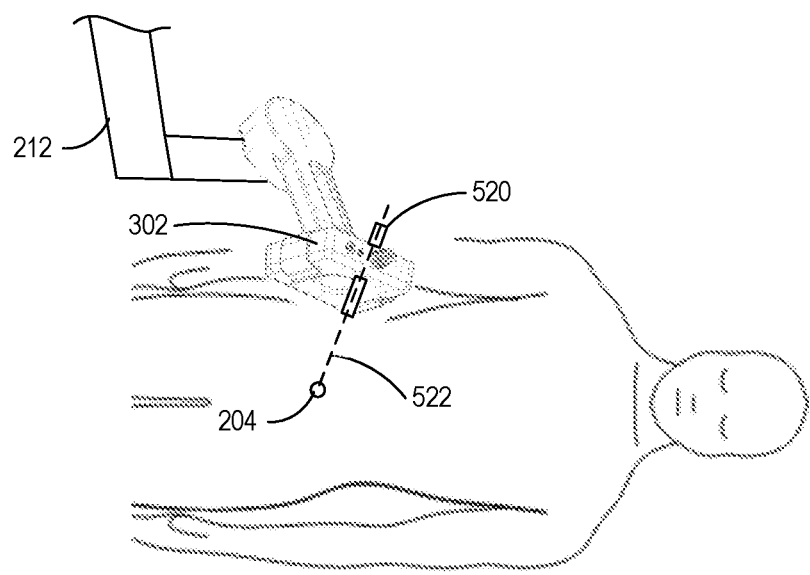

FIGS. 43A and 43B illustrate an embodiment of a robotic medical system, such as the system 300 of FIGS. 23 and 29, with a robotically controllable field generator 302 configured to facilitate alignment of an instrument guide 520 mounted on the field generator 302 with an EM target 204A. The instrument guide 520 can be configured such that a percutaneously insertable instrument can be inserted therethrough along an axis 522 during insertion into the patient. The instrument guide 520 can limit motion of the percutaneously insertable instrument to motion only along the axis 522, such that when the axis 522 is aligned with the EM target 204, the percutaneously insertable instrument can be guided toward the EM target 204. In some embodiments, the instrument guide 520 is removably coupled to the EM field generator 302. In other embodiments, the instrument guide 520 can be permanently coupled to or integrated into the EM field generator 302. In related aspects, it is noted that the instrument guide 520 may be configured to have shapes/curves and/or lengths different than the example of FIGS. 43A and 43B.

Similar to the example previously described, the axis 522 of the instrument guide 520 can be aligned with the EM target 204 to guide a percutaneously insertable instrument toward the EM target 20A. For example, the processor 380 can be configured to determine a registration that maps positions within an EM coordinate frame 308 associated with the EM field generator 308 to positions within a robotic coordinate frame 216 based on a kinematic pose of the first robotic arm 212. The processor 380 can also determine, based on the registration, a position of the EM target 204 within the robotic coordinate frame 216, and, based on the position of the EM target 204 within the robotic coordinate frame 216, the processor 280 can cause movement of the first robotic arm 212 to align the insertion axis 522 of the instrument guide 520 with the EM target 204.

FIG. 43A illustrates the system in a first state, wherein the axis 522 of the instrument guide 520 is not aligned with the EM target 204. FIG. 43B illustrates the system in a second state, after alignment of the axis 522 with the EM target 204. With the system in the second state, a percutaneously insertable instrument can be inserted through the instrument guide 520 along the axis 522 toward the EM target 204.

The system may also include the percutaneously insertable instrument. The percutaneously insertable instrument can comprise a needle, an access sheath, a laparoscopic instrument or another type of percutaneously insertable instrument. The percutaneously insertable instrument can extends along an axis. In some embodiments, the system comprises a second robotic arm coupled to and configured to move the percutaneously insertable instrument. In such cases, the processor can further be configured to align the axis of the percutaneously insertable instrument with the insertion axis using the second robotic arm, and insert the percutaneously insertable through the instrument guide along the insertion axis toward the EM target 204 using the second robotic arm. In some embodiments, the percutaneously insertable instrument may comprise an instrument manually inserted through the instrument guide 520.

Figure 44A:
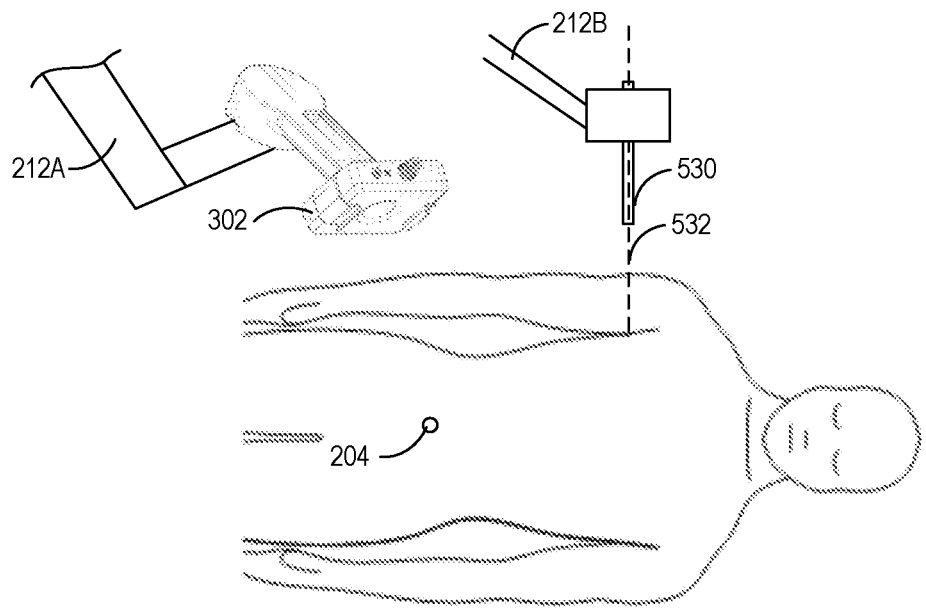
FIGS. 44A and 44B illustrate an embodiment of a robotic medical system with a robotically controllable field generator configured to facilitate alignment of an instrument guide with an EM target, according to an example embodiment.
Figure 44B:
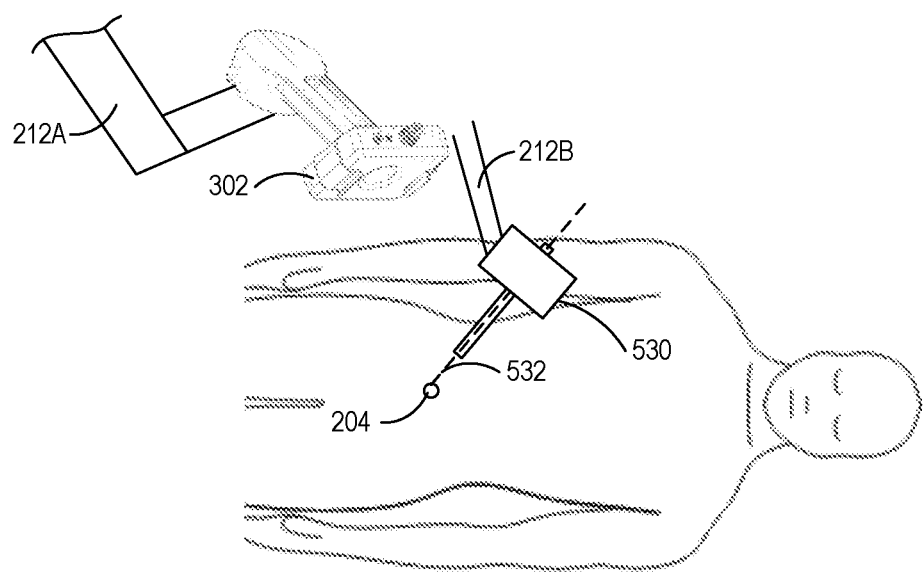

In some embodiments, the EM target 204 comprises an EM sensor positioned on a medical instrument configured for insertion into the patient. The robotic medical instrument can be an endoscope. The system may comprise a third robotic arm coupled to and configured to control the robotic medical instrument FIGS. 44A and 44B illustrate an embodiment of a robotic medical system with a robotically controllable field generator 302 configured to facilitate alignment of an instrument guide 530 with an EM target 204. This example is similar to the example of FIGS. 43A and 43B, except that the instrument guide 530 is coupled to a second robotic arm 212B, rather than to the EM field generator 302. In a similar manner, the processor 380 can be configured to determine a registration that maps positions within an EM coordinate frame 308 associated with the EM field generator 302 to positions within a robotic coordinate frame 216 based on a kinematic pose of the first robotic arm 212A, to which the EM field generator 302 is attached. The processor 380 can further determine, based on the registration, a position of the EM target 204 within the robotic coordinate frame, and based on the position of the EM target within the robotic coordinate frame, move the second robotic arm 212B to align an insertion axis 532 of the instrument guide with the EM target 204. FIG. 44A illustrates the system prior to alignment of the axis 532 of the instrument guide 530 with the EM target 204, and FIG. 44B illustrates the system after alignment. In the position illustrated of FIG. 44B, a percutaneously insertable instrument can be inserted through the instrument guide 530 toward the EM target 204.

In some embodiments, the percutaneously insertable instrument is coupled to a third robotic arm that is configured to move the percutaneously insertable instrument. In such cases, the processor can be further configured to align the axis of the percutaneously insertable instrument with the insertion axis 532 of the instrument guide 530 using the third robotic arm, and insert the percutaneously insertable through the instrument guide 530 along the insertion axis 532 toward the EM target 204 using the third robotic arm. In other embodiments, the percutaneously insertable instrument can be manually inserted through the instrument guide 530.

The system may also comprise a robotic medical instrument configured for insertion into the patient. The EM target 204 can comprise an EM sensor on the robotic medical instrument. The robotic medical instrument can be coupled to another robotic arm that is configured to control the robotic medical instrument.

Figure 45A:
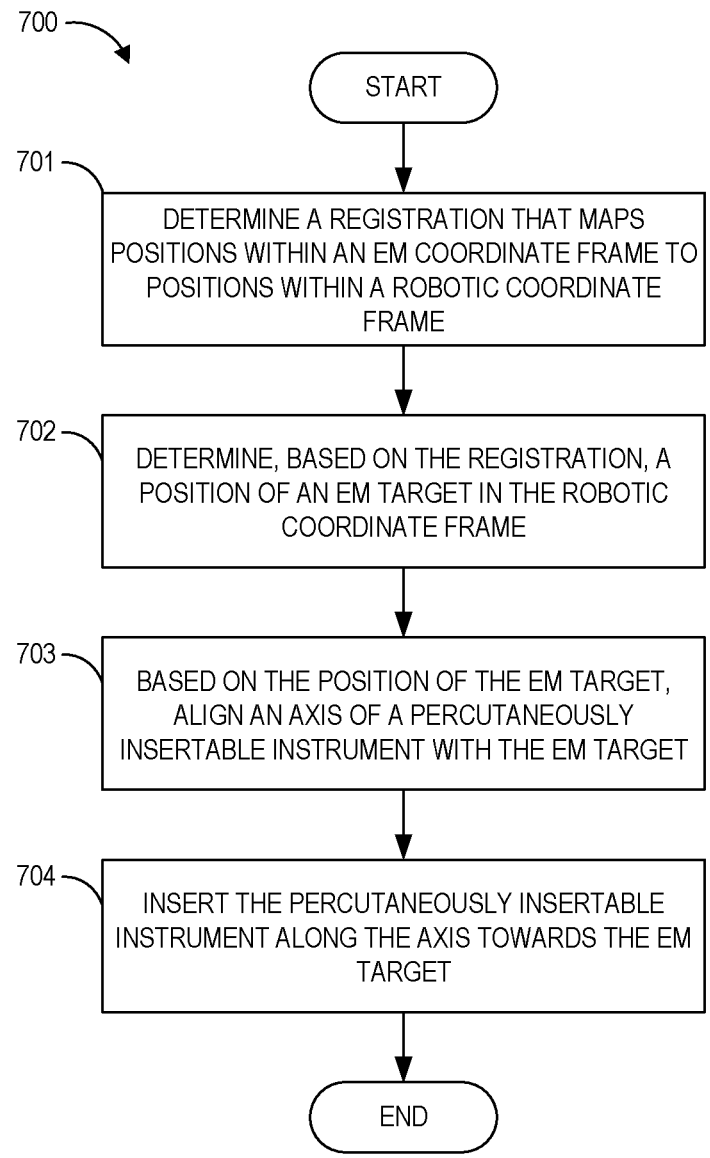
FIG. 45A is a flowchart illustrating a method for aligning a percutaneously insertable instrument with an EM target using a robotically controllable field generator, according to an example embodiment.

FIG. 45A is a flowchart illustrating a method 700 for aligning a percutaneously insertable instrument with an EM target using a robotically controllable field generator. The method 700 begins at block 701, at which a registration that maps positions within an EM coordinate frame to positions within a robotic coordinate frame. The registration can be determined based on a kinematic pose of a robotic arm to which an EM field generator is attached as previously described.

Next, at block 702, the position of an EM target can be determined in the robotic coordinate frame based on the registration. As described previously, this can involve determining the position of the EM target within an EM field generated by the EM field generator and mapping that position into the robotic coordinate frame.

Based on the determined position of the EM target, at block 703, an axis of a percutaneously insertable instrument is aligned with the EM target. An example is shown in FIG. 42B, described above. Finally, at block 704, the percutaneously insertable instrument can be inserted along the axis towards the EM target. An example is shown in FIG. 42C, described previously.

Figure 45B:
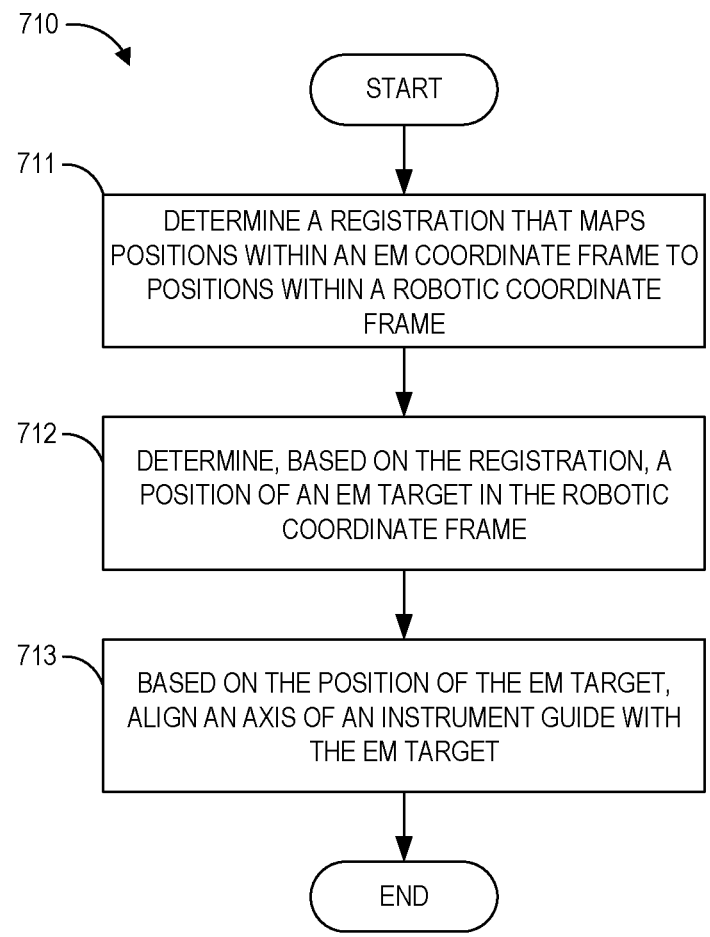
FIG. 45B is a flowchart illustrating a method for aligning an instrument guide for a percutaneously insertable instrument with an EM target using a robotically controllable field generator, according to an example embodiment.

FIG. 45B is a flowchart illustrating a method 710 for aligning an instrument guide for a percutaneously insertable instrument with an EM target using a robotically controllable field generator. At block 711, the method 700 involves determining a registration that maps positions within an EM coordinate frame to positions within a robotic coordinate frame. At block 712, the position of an EM target is determined within the robotic coordinate frame based on the registration. And finally, at block 713, the method 700 involves aligning an axis of the instrument guide with the EM target. Examples have been described above with reference to FIGS. 43A and 43B, which show an instrument guide on the EM field generator, and FIGS. 44A and 44B, which show an instrument guide mounted on a second robotic arm.

iv. Distortion Detection

The robotically controlled EM field generator 302 can also be used for distortion detection. For example, a robotically controlled EM field generator can be commanded to move while a static EM sensor is present in the region of interest, e.g., a needle-insertion site, a biopsy site, or any static position within the working volume of the EM field generator. The EM field generator 302 can be moved by a robotic arm 212 to which it is attached and the commanded robot motion (within a robotic coordinate frame) can be compared with the recorded EM sensor trajectory (within an EM coordinate frame). The difference between the two trajectories can be a measure or indicator of the distortion in the EM signal within the working volume of the EM field generator 302. A similar principle can also be used with a non-static EM sensor whose motion is either known or has bounded uncertainty. The accuracy of distortion detection may depend on or be bounded by the uncertainty of the knowledge of the EM sensor motion/location.

Figure 46A:
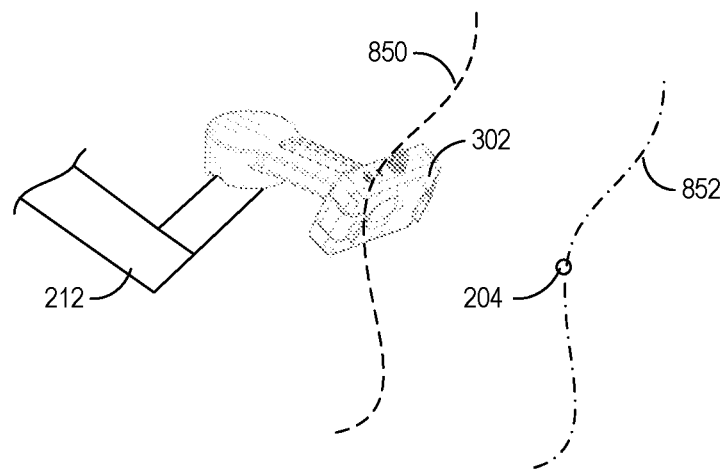
FIG. 46A illustrates an embodiment of a robotic medical system moving an EM field generator relative to a fixed EM position sensor in order to detect EM distortion, according to an example embodiment.

FIG. 46A, for example, illustrates an embodiment of a robotic medical system moving an EM field generator 302 relative to a fixed EM position sensor 204 in order to detect EM distortion. As shown in the illustrated embodiment, the EM field generator 302 can be coupled to a first robotic arm 212. The EM field generator 302 can be configured to generate an EM field and is associated with an EM coordinate frame within which the position of EM sensors, such as the illustrated EM sensor 204 can be determined with reference to the EM coordinate frame. The first robotic arm 212 can be configured to move to reposition the EM field generator 302. The first robotic arm 212 can be associated with a robotic coordinate frame. As described above, the motion of the robotic arm 212 within the robotic coordinate frame is known due to the known kinematics of the arm. Accordingly, since the EM field generator 302 is coupled to the first robotic arm 212, the position of the EM field generator 302 within the robotic coordinate frame 212 can also be determined based on the kinematic pose of the arm. As described in more detail above, this relationship can establish a registration that can be used to determine positions of EM sensors 204 within the EM coordinate frame of the EM field with respect to the robotic coordinate frame.

In the illustrated embodiment of FIG. 46A, in order to determine or detect EM distortion within the EM field, the EM sensor 204 can be provided at a fixed and stationary position. For example, the EM sensor 204 can be affixed to a non-moving object, such as a patient platform or other non-moving piece of equipment. In some embodiments, the EM sensor 204 is positioned on a medical instrument, such as a robotically controlled medical instrument. If this is the case, during a distortion detection step as described with reference to FIGS. 46A-47, the medical instrument can remain stationary such that the position of the EM sensor 204 remains fixed and stationary.

In order to detect EM distortion, a processor in communication with the first robotic arm 212 (and, by extension, the EM field generator 302) can be configured to cause the first robotic arm 212 to move the EM field generator 302 along a robotic trajectory 850. In FIG. 46A, the robotic trajectory 850 is represented by a dashed line, and the system is illustrated approximately halfway through the movement, such that the EM field generator 302 is positioned about halfway along the robotic trajectory 850. In some embodiments, movement of the EM field generator 302 by the first robotic arm 212 along the robotic trajectory 850 can be accomplished under direction or control of an operator, such as a physician, who can command the motion using a controller or other user interface. In other embodiments, the movement of the EM field generator 302 by the first robotic arm 212 along the robotic trajectory 850 can be automatically provided, for example, as part of an automatic EM distortion detection process operated by the system.

In FIG. 46A, it is important to realize that, in this example, the EM field generator 302 is moved along the robotic trajectory 850, and that this occurs while the EM sensor 204 remains stationary or fixed as described above. FIG. 46A also illustrates an EM sensor trajectory 852, which is represented in the figure as a dot-dash lined. The EM sensor trajectory 852 is, however, not a result of physical movement of the EM sensor 204, which as noted above, remains fixed. Rather, the EM sensor trajectory 852 is generated due to the movement of the EM field generator 302 relative to the stationary EM sensor 204. For example, as the first robotic arm 212 moves the EM field generator 302 along the robotic trajectory 850, the position of the EM sensor within the EM coordinate frame associated with the EM field generator 302 is recorded, producing the EM trajectory 852.

Accordingly, the robotic trajectory 850 is caused by the movement of the EM field generator 302 by the first robotic arm 212. The robotic trajectory 850 can be detected, determined, and/or recorded based on the known kinematic movement of the first robotic arm 212 during the motion. In contrast, the EM sensor trajectory 852 is caused by the movement of the EM field generator 302 relative to the stationary EM sensor 204. The EM sensor trajectory 852 can be detected, determined, and/or recorded based on detecting the EM sensor 204 within the EM field of the EM field generator 302 as the EM field generator 302 is moved and the EM sensor 204 remains stationary.

Because the EM sensor 204 remains fixed during movement of the EM field generator 302 by the first robotic arm 212, in the absence of any EM distortion, one would expect the robotic trajectory 850 to correspond to the EM sensor trajectory 852. This is because the movement of the EM field generator 302 should match the relative motion between the moving EM field generator 302 and the static EM sensor 204. Accordingly, differences between the robotic trajectory 850 and the EM sensor trajectory 852 can be analyzed to determine whether EM distortion is present. In some embodiments, the analysis may also provide a measure of the degree or severity of the EM distortion.

Figure 46B:
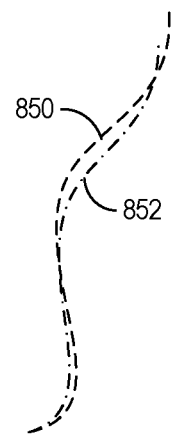
FIG. 46B illustrates a comparison of a robotic trajectory and an EM sensor trajectory during the movement of the EM field generator of FIG. 46A, according to an example embodiment.

FIG. 46B illustrates comparison of the robotic trajectory 850 and the EM sensor trajectory 852. In this example, start points of each trajectory have been aligned, although this need not be necessary in all embodiments. As shown in FIG. 46B, it is apparent that the robotic trajectory 850 and the EM sensor trajectory 852 do not exactly correspond. The difference(s) between the trajectories can be determined in order to detect EM distortion. In some embodiments, the detected EM distortion is indicative of EM distortion at the location of the fixed EM sensor 204.

Not all differences between the robotic trajectory 850 and the EM sensor trajectory 852 are necessarily caused by EM distortion. For example, the robotic system may not be able to determine robotic motion with total accuracy for various reasons including manufacturing tolerances, motor control limitations, sensor accuracy, etc. Accordingly, some of the differences between the robotic trajectory 850 and the EM sensor trajectory 852 may be caused by imprecision in determining robotic motion. In general, however, imprecision in determining robotic motion can be small, for example, in a sub-millimeter range. Similarly, the EM field generator 302 may be subject to EM noise that can lead to a reduced resolution of EM sensor positions determined within the field. This can lead to imprecise recording of the EM sensor trajectory 852, causing differences, that are not directly attributable to EM distortion. Again, however, an EM field generator can be configured or selected such that the EM sensor noise is, in some embodiments, around 1 millimeter or less. Accordingly, for some embodiments of the robotic system, imprecision in the determination of the robotic motion and also imprecision in the recording the EM sensor position within the EM field can lead to potential inaccuracies of about 1 millimeter or less.

Accordingly, to determine the presence of EM distortion, it can be beneficial to analyze differences between the robotic trajectory 850 and the EM sensor trajectory 852 with respect to a threshold value that is selected to exclude or reduce the contributions due to other factors. In some embodiments, the threshold value can be, for example, 1 millimeter, 1.25 millimeters, 1.5 millimeters, 1.75 millimeters, 2 millimeters, 2.25 millimeters, 2.5 millimeters, 2.75 millimeters, 3 millimeters or greater. In many instances, it is beneficial to set the threshold value such that it is larger than one or both of an error factor associated with motion of the first robotic arm or an error factor associated with EM sensor or generator noise.

Comparing the robotic trajectory 850 and the EM sensor trajectory 852 can be accomplished in a variety of ways. For example, the shapes of the robotic trajectory 850 and the EM sensor trajectory 852 can be directly compared as shown in FIG. 46B. The shapes can be analyzed to determine how closely they correspond, and if the deviation between the shapes exceeds a threshold, the system can determine that EM distortion is present and/or the degree of EM distortion. In another embodiment, analyzing the robotic trajectory 850 and the EM sensor trajectory 852 to determine a difference therebetween can comprise comparing a plurality of points along the robotic trajectory 850 to a corresponding plurality of points along the EM sensor trajectory 852. In some embodiments, the plurality of points are determined with respect to a time associated with movement of the EM field generator 302 using the first robotic arm 212. For example, a point on the robotic trajectory 850 at the start of the movement (e.g., at t=0) can be compared with a corresponding point on the EM sensor trajectory 852. Then, subsequent points can be compared at discrete time steps thereafter.

In some embodiments, if EM distortion is detected, the system can be configured to reposition the EM field generator 302 with the first robotic arm 212 at a location that reduces the EM distortion. For example, in some embodiments, the system can position the EM field generator 302 at a position along the robotic trajectory 850 at which a difference between the robotic trajectory 850 and the EM sensor trajectory 852 is reduced.

In some embodiments, this can be achieved by moving the EM field generator 302 along a second robotic trajectory in an effort to identify a location that can reduce the EM distortion. Accordingly, the EM field generator 302 can be moved along a second robotic trajectory that is different than the first robotic trajectory 850. For example, the EM field generator 302 can be moved along the second robotic trajectory through different space than was covered along the first robotic trajectory 850. As before, this is done while the EM sensor 204 remains stationary. The second robotic trajectory can be recorded along with a second and corresponding EM sensor trajectory. These trajectories can be analyzed to determine if a location that reduces EM distortion can be determined. If so, the EM field generator 302 can be moved, using the robotic arm 212, to that position. If not, additional robotic trajectories can be attempted until a suitable location for the EM field generator 302 that reduces EM distortion can be found.

In the examples described above with respect to FIGS. 46A and 46B, the robotic trajectory 850 has been defined with respect to a global robot reference frame, whereas the EM sensor trajectory 852 is defined with respect to the EM field generator coordinate frame. In this case, in order to compare the robotic trajectory 850 to the EM sensor trajectory 852, the EM field generator coordinate frame must be registered to the global robot reference frame. This can be achieved, for example, as described above, because the EM field generator 302 is attached to the robotic arm 212, establishing a kinematic relationship between the global robot reference frame and the EM field generator coordinate frame.

Figure 46C:
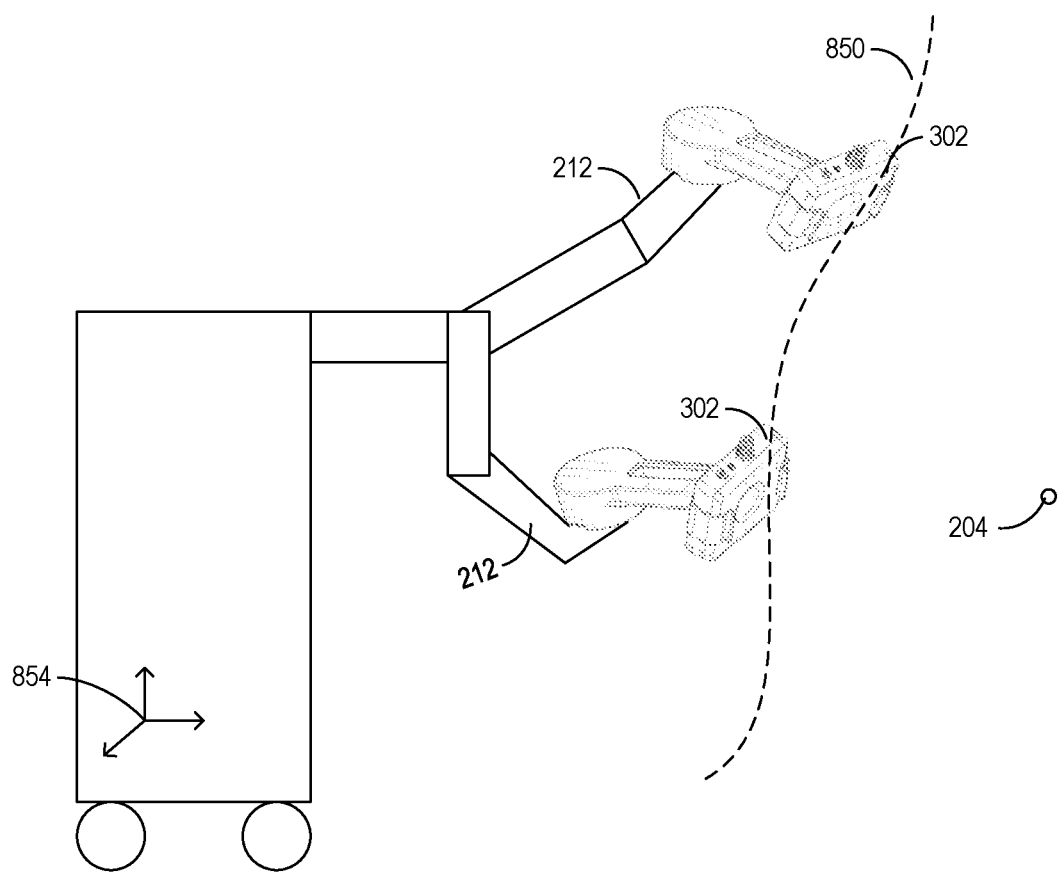
FIG. 46C illustrates an embodiment of a robotic medical system moving an EM field generator relative to a fixed EM position sensor in order to detect EM distortion that can account for changes in position and orientation, according to an example embodiment.

Moreover, the examples described above with respect to FIGS. 46A and 46B are somewhat simplified, for ease of understanding and illustration, with the assumption that only the position of the EM field generator 302 relative to the EM sensor 204 has been changed and not the relative orientation. In more complex examples, both the position and orientation of the EM field generator 302 relative to the EM sensor 204 can be changed and the detected position (and/or orientation) of the EM sensor 204 can be analyzed to determine whether EM distortion is present (and/or a degree thereof). In such cases, the determination of EM distortion can be made with respect to a global reference frame 854 associated with a cart to which the robotic arm 212 is attached, as shown in FIG. 46C, which illustrates the robotic arm 212 to which the EM field generator 302 is attached as it moves along a robotic trajectory 850 that changes the position and orientation of the EM field generator 302 relative to the EM sensor 204. Because the cart and the EM sensor 204 are not moving, any detected position and/or orientation change measured with respect to the global reference frame 854 would be due to distortion (and negligible kinematics error).

EM distortion can be caused by any or all components that are positioned within the working volume of the EM field generator. Accordingly, similar processes can be performed while moving other components in an effort to find optimal or preferred positions for other components.

Figure 47:
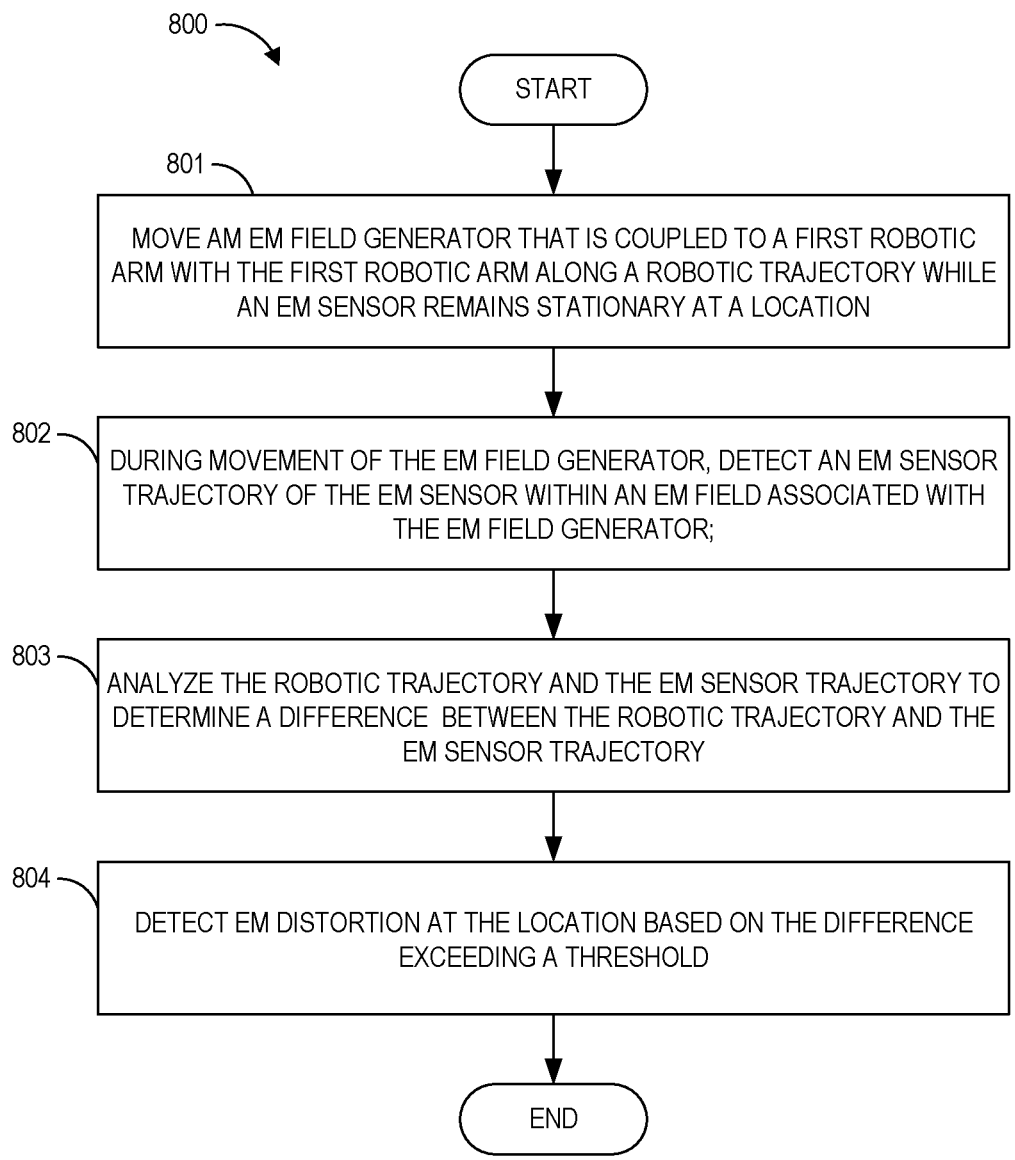
FIG. 47 is a flowchart illustrating an example method for EM distortion detection, according to an example embodiment.

FIG. 47 is a flowchart illustrating an example method 800 for EM distortion detection. The method 800 is similar in many respects to the process described above with respect to FIGS. 46A 46C. The method 800 can be performed using a robotic medical system, such as the systems previously described, in which an EM field generally is robotically controllable via attachment to a robotic arm of the system.

The method 800 begins at block 801. Block 801 can involve moving an EM field generator that is coupled to a first robotic arm with the first robotic arm along a robotic trajectory while an EM sensor remains stationary at a location. As described above, the robotic trajectory can be determined based on the kinematics of the arm to which the EM field generator is attached. In some embodiments, the robotic trajectory can be determined with respect to a global reference frame, which may, for example, be associated with a cart to which the robotic arm is attached. In some embodiments, block 801 is performed by a processor (or processors) of a robotic medical system. For example, a processor may be configured to transmit a command to the first robotic arm to cause movement of the EM field generator along a robotic trajectory. In some cases, the EM sensor may be fixed to determinable position while the EM field generator moves along the robotic trajectory.

At block 802, an EM sensor trajectory of the EM sensor within an EM field associated with the EM field generator can be detected based on the sensor data generated by the EM sensors as the EM field generator moves along the robotic trajectory. In this way, and as noted previously, the EM trajectory may be the recorded position of the EM sensor within the EM field during the same time period as when the EM field generator was moved by the robotic arm according to the robotic trajectory.

At block 803, the robotic trajectory and the EM sensor trajectory are analyzed to determine difference(s) therebetween. Analysis can be performed in a number of ways, including comparing the shapes of the trajectories and/or comparing a plurality of discrete points along the trajectories, among others. Such comparison can consider changes in position and/or orientation.

At block 804, EM distortion can be detected at the location of the EM sensor based on a comparison between the difference between the trajectories and a threshold. The threshold can be selected or determined so as to reduce or exclude contributions caused by factors other than EM distortion, such as errors in recording or determining robotic motion and/or in detecting the EM sensor position within the EM field.

Figure 48:
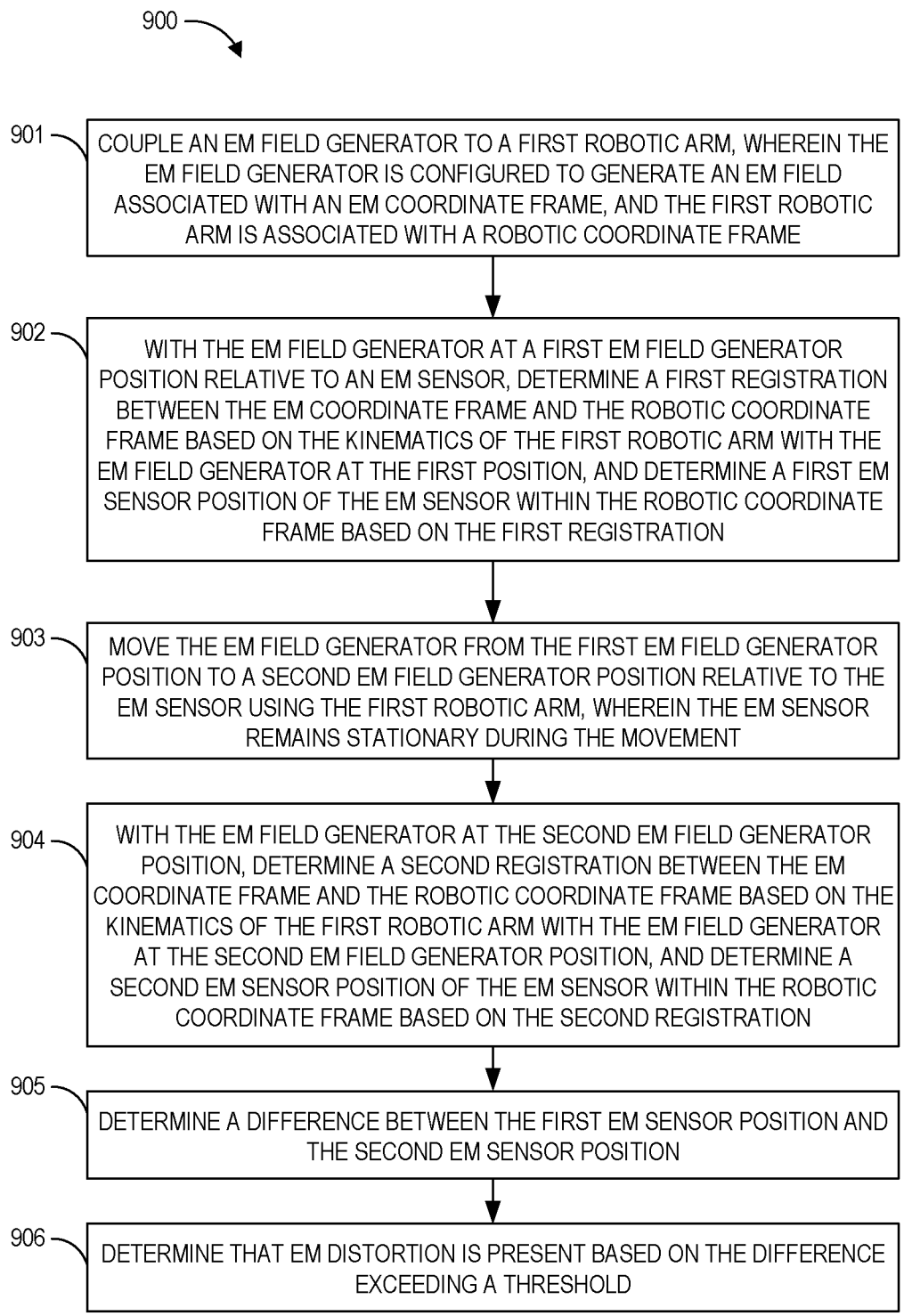
FIG. 48 is a flowchart illustrating another example method for EM distortion detection, according to an example embodiment.

FIG. 48 is a flowchart illustrating another example method 900 for EM distortion detection. The method 900 can be performed using a robotic medical system, such as the systems previously described, in which an EM field generally is robotically controllable via attachment to a robotic arm of the system. The method 900 begins at block 901, at which a first robotic arm is coupled to an EM field generator. The EM field generator is configured to generate an EM field and is associated with an EM coordinate frame. The first robotic arm is associated with a robotic coordinate frame and the position of the coupled EM field generator can be determined within the robotic coordinate frame based on the kinematic pose of the first robotic arm. In some embodiments, the position can further be determined with respect to a global coordinate frame, such as a coordinate frame associated with a cart to which the robotic arm is attached. A position of an EM sensor within a working volume of the EM field of the EM field generator can be determined and mapped into the robotic coordinate frame (or the global coordinate frame) based on the pose of the arm as previously described.

At block 902, with the EM field generator at a first EM field generator position relative to the EM sensor, the method 900 includes determining a first registration between the EM coordinate frame and the robotic coordinate frame based on the kinematics of the first robotic arm with the EM field generator at the first position and determine a first EM sensor position of the EM sensor within the robotic coordinate frame based on the first registration.

At block 903, the method 900 includes moving the EM field generator from the first EM field generator position to a second EM field generator position relative to the EM sensor using the first robotic arm, wherein the EM sensor remains stationary during the movement. In some embodiments, movement of the EM field generator by the first robotic arm can be accomplished under direction or control of an operator, such as a physician, who can command the motion using a controller or other user interface. In other embodiments, the movement of the EM field generator by the first robotic arm along the robotic trajectory can be automatically provided, for example, as part of an automatic EM distortion detection process operated by the system.

At block 904, with the EM field generator at the second EM field generator position, a second registration between the EM coordinate frame and the robotic coordinate frame based on the kinematics of the first robotic arm with the EM field generator at the second EM field generator position is determined, and a second EM sensor position of the EM sensor within the robotic coordinate frame (or the global coordinate frame) based on the second registration is also determined. The second registration is necessary because the EM field generator has been moved, the new kinematic pose of the robotic arm at the second position is used to establish the new relationship between the robotic coordinate frame and the EM coordinate frame.

At block 905, the method 900 includes determining a difference between the first EM sensor position and the second EM sensor position. Since the EM sensor has not moved, one would expect the determined positions to be the same. However, EM distortion caused by the different positions of the robotic arm and EM field generator (or other components that have been moved) can cause the determined positions to vary. In some embodiments, changes in orientation may also be considered. At block 906, EM distortion can be detected based on a comparison between the difference and a threshold (e.g., the difference exceeding the threshold). As noted above, other factors can contribute to the difference. As before, the threshold can be selected or determined to reduce the contribution of these other, non-EM distortion, factors.

When viewed relative to the threshold, a difference exceeding the threshold can indicate that EM distortion is present. However, by only testing two EM field generator positions (and/or orientations), it may be difficult to determine which position provided the most accurate determination of position. Accordingly, it can be advantageous to continue to test a plurality of other EM field generator positions (and/or orientations) by repeating the associated steps of: moving the EM field generator to a new position using the robotic arm, determining a new EM to robotic coordinate registration based on the new position of the EM field generator based on the kinematics of the robotic arm, and determining the position of the EM sensor within the robotic coordinate frame based on the newly determined registration.

In some embodiments, this process can be continued to build a map of the EM distortion by determining the distortion at a plurality of locations. Locations of the EM field generator that that provide determinations of the EM sensor position with the least variation from the other positions can be determined to have low EM distortion, while locations of the EM field generator that that provide determinations of the EM sensor position with the most variation from the other positions can be determined to have high EM distortion. In this way, the system or an operator can determine how best to position the EM field generator and other components so as to reduce EM distortion.

EM distortion that is detected using the methods described above (as well as EM distortion generally) can be both static or dynamic. Static EM distortion is unchanging and can determined and removed from EM measurements by applying a corresponding correction value. Static EM distortion can be caused by a number of factors including objects within the operating room that are generally unmoving and thus do not change during a procedures as well as larger scale factors such as the magnetic field of the earth. Dynamic EM distortion is caused by factors that change over the course of a procedure. These can include any of the moving robotic components of the system, as well as other components (or even people) who may move through the operating room. Distortion detection can be used to both detect and correct for static distortions as well as to find optimal positions for moving component that reduce dynamic distortions.

v. Multi-Modal Sensor Fusion

The robotically controlled EM field generator 302 can also be useful in allowing for multi-modal sensor fusion. As used herein, multi-modal sensor fusion can refer to simultaneous or concurrent use of different sensor types during a single procedure in a synergized way. As an example, with the EM field generator 302 that is rigidly mounted on the robotic arm 212, EM sensing technology can be registered to other imaging and sensing modalities mounted on the robotic arm 212 or in the robotic system. Registration of the EM sensing modality with other imaging and sensing modalities attached to or part of the robotic arm, cart, or base may facilitate, for example, providing a simplified display (wherein data from a plurality of sensing modalities can be displayed together in a unified way), augmented reality, or the like. In this section, examples will be described wherein EM sensing technology can be used with ultrasound technology to provide for multi-modal functionality. This may allow, for example, accurate identification of a needle tip (where the needle tip includes an EM sensor) in ultrasound images. In general, determination of the needle tip in an ultrasound image may not be straightforward, as artifacts may distort the image. Registering the imaging plane of the ultrasound and the EM field to single space, such as the robotic coordinate frame, can facilitate determination of the needle tip in the ultrasound image. To achieve this, an ultrasound probe can be rigidly mounted on a robotic arm, as will be described in more detail below. If the ultrasound imaging plane is kinematically known with respect to the coordinate frame of the EM field generator 302, the EM sensor inside the needle can be tracked in real-time and overlaid on the ultrasound image(s).

Attaching an ultrasound probe to a robotic arm can facilitate registration or calibration of the ultrasound probe's imaging plane. Calibration of an ultrasound probe's imaging plane can generally require capturing three different ultrasound images from three different, known positions. The three ultrasound images, along with the corresponding known positions, can be used to calibrate the imaging plane. Conventionally, additional equipment has been required to calibrate ultrasound probes used in surgical robotic systems. For example, external position tracking systems would have to be set up to determine the positions at which the three ultrasound images are captured. As a specific example, optical sensors (such as infrared LED) can be attached to an ultrasound probe. A position tracking system, such as Optitrack, can detect the positions of the optical sensors that are attached to the ultrasound probe and used to determine the position thereof. In a surgical robotic setting, this can be disadvantageous as additional equipment is required.

By attaching an ultrasound probe to a robotic arm, the position of the ultrasound probe can readily be determined with respect to a robotic coordinate frame associated with the arm based on the kinematics of the arm in a manner similar to that described above with respect to the EM field generator attached to a robotic arm. A base ultrasound image can be captured at this base position. The robotic arm can then move the ultrasound probe to a first position at which a first ultrasound image is captured and the first position can be determined based on the kinematics of the arm. The robotic arm can then move the ultrasound probe to a second position at which a second ultrasound image is captured and the second position can be determined based on the kinematics of the arm at the second position. The three images (base, first, and second) and positions (base, first, and second) can then be used to calibrate the imaging plane of the ultrasound probe without requiring any external or additional equipment, such as conventional position tracking equipment.

Figure 49A:
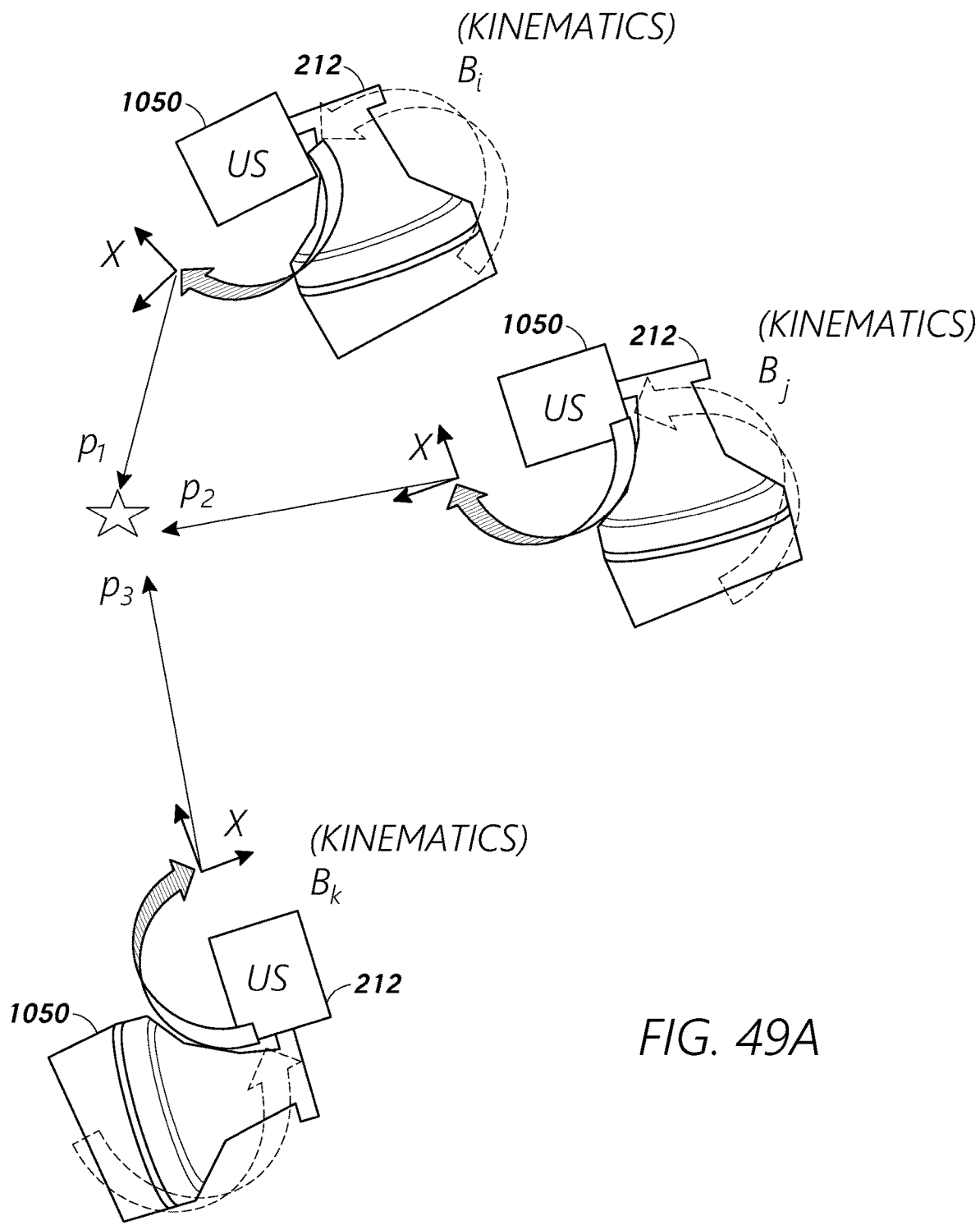
FIG. 49A illustrates a robotic medical system with an ultrasonic probe attached thereto during a procedure for calibrating an imaging place of the ultrasonic probe, according to an example embodiment.

FIG. 49A illustrates a robotic medical system with an ultrasonic probe 1050 attached to a robotic arm 212 during a procedure for calibrating an imaging place of the ultrasonic probe. In the illustrated embodiment, the robotic arm 212 is coupled to the ultrasound probe 1050. For example, the ultrasound probe 1050 can be attached to a distal end of the robotic arm 212 or an instrument device manipulator (IDM) positioned on the arm. The robotic arm 212 is configured to move to adjust a position the ultrasound probe 1050. The robotic arm 212 is also associated with a robotic coordinate frame as described previously. In the illustrated embodiment of FIG. 49A, three positions Bi, Bj, and Bk are illustrated. The robotic arm 212 moves to move the ultrasound probe 212 between these three positions. At each position, the kinematics of the arm can be used to determine the position of the ultrasound probe in the robotic coordinate frame.

At the first position Bi the ultrasound probe 1050 can capture a first image. The ultrasound probe 1050 is then moved to the second position Bj using the robotic arm 212. At the second position Bj a second ultrasound image is captured with the ultrasound probe 1050. The ultrasound probe 1050 is then moved to the third position Bj using the robotic arm 212. At the third position Bj a third ultrasound image is captured with the ultrasound probe 1050. The system can calibrate an imagining plane of the ultrasound probe 1050 relative to the robotic coordinate frame based on the first ultrasound image and first kinematics of the first robotic arm with the ultrasound probe at the first ultrasound probe position, the second ultrasound image and second kinematics of the first robotic arm with the ultrasound probe at the second ultrasound probe position, and the third ultrasound image and third kinematics of the first robotic arm with the ultrasound probe at the second ultrasound probe position.

Figure 49B:
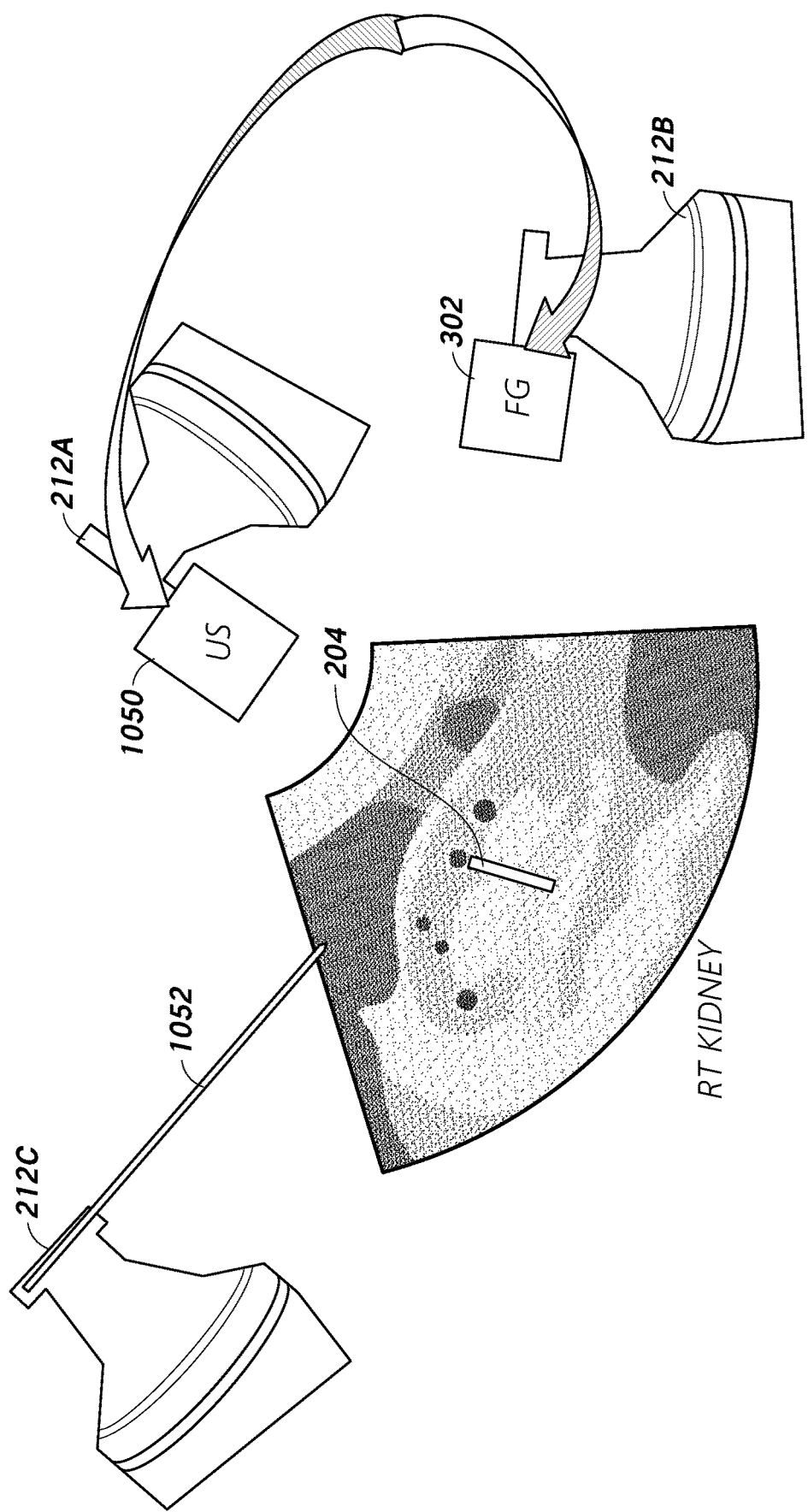
FIG. 49B illustrates a robotic medical system including an EM field generator and an ultrasonic probe. The imaging plane of the ultrasonic probe is calibrated with respect to a robotic coordinate frame and an EM coordinate frame such that robotic tools and EM sensor positions can be overlaid on the imaging plane, according to an example embodiment.

With the imaging plane calibrated and registered to the robotic coordinate frame, the robotic system can take advantageous of a plurality of sensing modalities concurrently. FIG. 49B illustrates an example multi-modal robotic system. As shown in FIG. 49B, a robotic system can include a first robotic arm 212A, a second robotic arm 212B, and a third robotic arm 212C. The robotic arms can be attached to a cart, a patient platform, or other common structure such that each is associated with a common robotic coordinate frame. In the illustrated embodiment, the ultrasound probe 1050, for which the imaging plane has been calibrated, is attached to the first robotic arm 212A. An EM field generator 302 is attached to the second robotic arm 212B. The EM field generator 302 is configured to generate an EM field within which positions of EM sensors, such as the EM sensor 204, can be determined. Using the EM to robotic coordinate frame registration procedures described above, the position of the EM sensor 204 can be determined within the robotic coordinate frame. Since the imaging plane of the ultrasound probe has also been registered to the robotic coordinate frame, the imagine plane the position of the EM sensor 204 are both determined within a common space (the robotic coordinate frame) and thus, can both be displayed on a common display as shown in FIG. 49B.

In FIG. 49B, the EM sensor 204 can be positioned on a distal end of a scope that is inserted into a treatment region of the patient. The scope can be a robotically controlled medical instrument attached to and controlled by a different robotic arm. Alternatively, the scope can be a manually controlled scope. FIG. 49B also illustrates that a medical instrument, such a needle can be attached to the third robotic arm 212C. The position of the needle, which can be rigidly attached to the third robotic arm 212C can also be determined with respect to the robotic coordinate frame. Accordingly, the position of the needle can also be displayed along with the imagine plane and EM sensor data. In this way, various sensor technologies can be fused in a single robotic system and used concurrently during a single procedure. In this example, rendezvous of the needle with the scope is facilitated by robotic data, ultrasound date, and EM data, which can improve the accuracy of rendezvous and provide a comprehensive and improved operating experience.

Figure 50:
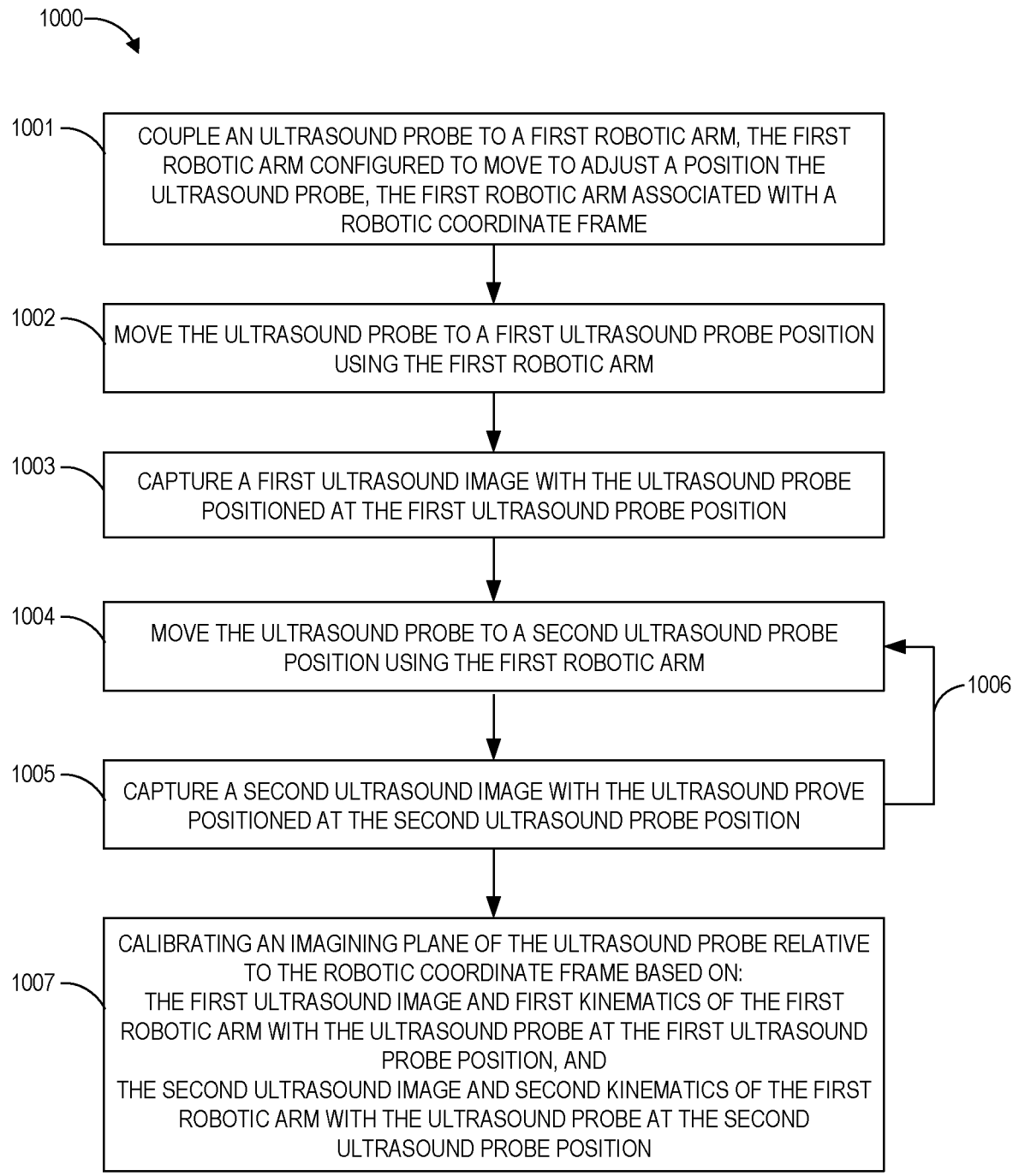
FIG. 50 is a flowchart illustrating an example method for calibrating an imaging plane of an ultrasonic probe for use with a robotic medical system, according to an example embodiment.

FIG. 50 is a flowchart illustrating an example method 1000 for calibrating an imaging plane of an ultrasonic probe for use with a robotic medical system. The method 1000 begins at block 1001, at which an ultrasound probe is coupled to a first robotic arm. The first robotic arm is configured to move to adjust a position the ultrasound probe, and the first robotic arm associated with a robotic coordinate frame. At block 1002, the ultrasound probe is moved to a first ultrasound probe position using the first robotic arm. The first ultrasound probe position can be a position at which a first ultrasound image to be used to calibrate the imaging plane of the ultrasound probe will be captured. The first position can be determined based on the kinematics of the first robotic arm. At block 1003, the first ultrasound image with the ultrasound probe positioned at the first ultrasound probe position. At block 1004, the ultrasound probe is moved to a second ultrasound probe position using the first robotic arm. The second ultrasound probe position can be a position at which a second image can be captured, which occurs at block 1005. The second image can also be used to calibrate the imaging plane of the ultrasound probe. The second position can be determined based on the kinematics of the arm. As illustrated by arrow 1006, blocks 1004 and 1005 can be repeated to capture a third image at a third position, for example, as shown in FIG. 49A. In some embodiments, these steps can be repeated additional times, capturing additional images at additional positions.

At block 1007, the imaging plane imagining plane of the ultrasound probe relative to the robotic coordinate frame can be calibrated based on the first ultrasound image and first kinematics of the first robotic arm with the ultrasound probe at the first ultrasound probe position, the second ultrasound image and second kinematics of the first robotic arm with the ultrasound probe at the second ultrasound probe position, and the third ultrasound image and third kinematics of the first robotic arm with the ultrasound probe at the third ultrasound probe position. When calibrated, the imaging plane can be determined with respect to the robotic coordinate frame and used with other sensing modalities (such as EM) which can also be determined with respect to the robotic coordinate frame.

In some embodiments, the method 1000 may also include coupling an EM field generator to a second robotic arm, wherein the EM field generator is configured to generate an EM field and the EM field generator associated with an EM coordinate frame, and wherein the second robotic arm is configured to move to adjust a position of the EM field generator and the second robotic arm associated with the robotic coordinate frame. The method 1000 may also include determining a registration between the EM field coordinate frame and the robotic coordinate frame based on kinematics of the second robotic arm. This can be accomplished as described previously. The first and second robotic arms can be attached to a cart or a patient platform defining a relationship between the first and second robotic arms within the robotic coordinate frame. This can allow the EM field generator and the ultrasound probe to both be brought within the robotic coordinate frame. The method 1000 may also include positioning an EM sensor within the EM field, and determining an EM sensor position within the robotic coordinate frame based on the registration. Additionally, the method 1000 may also include displaying the imaging plane of the ultrasound probe, and overlaying an indication of the determined EM sensor position on the displayed imaging plane of the ultrasound probe as shown, for example, in FIG. 49B.

Figure 51A:
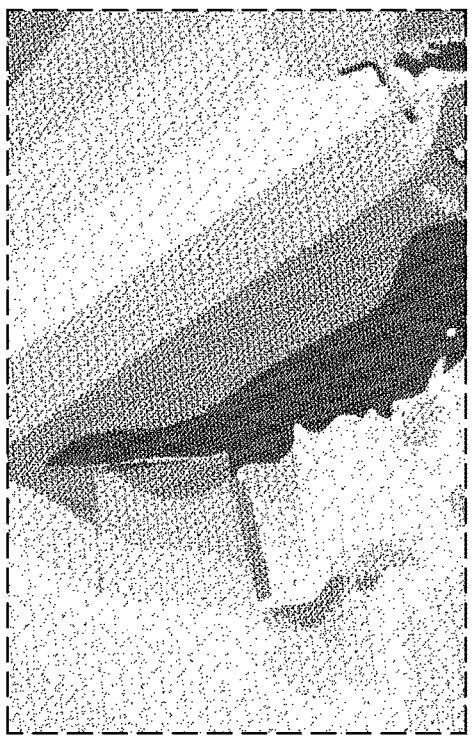
FIGS. 51A and 51B illustrate example heat and point maps generated using a depth sensor attached to a robotic arm of a robotic medical system, according to an example embodiment.
Figure 51B:
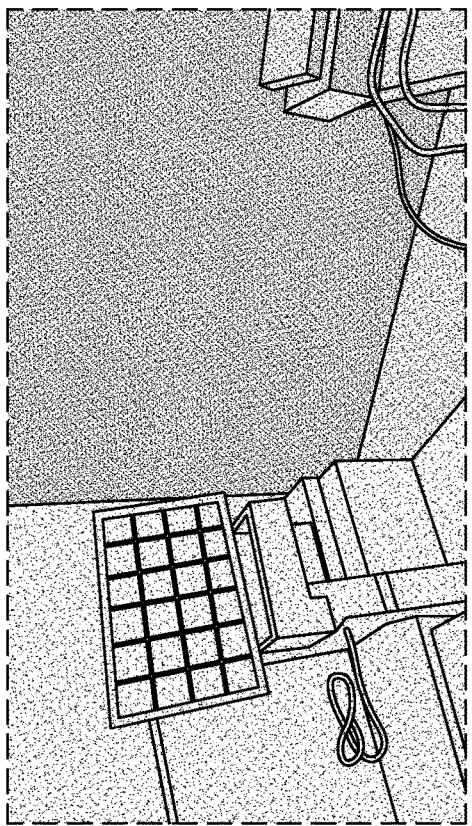
Figure 51C:
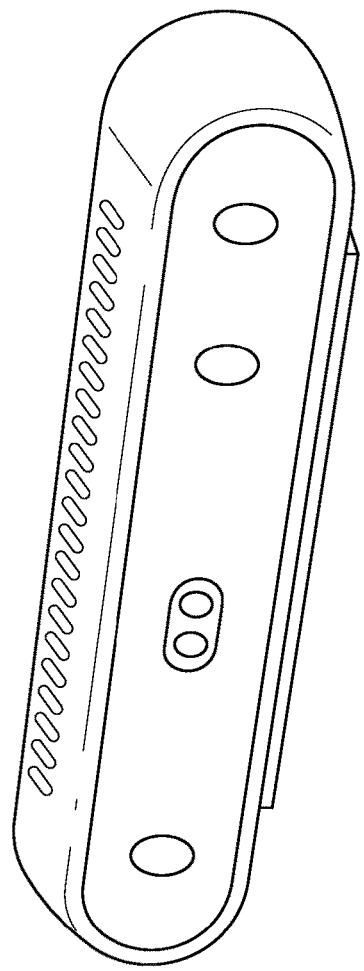
FIG. 51C illustrates an embodiment of an example depth sensor, according to an example embodiment.

Although multi-modal functionality has been described with respect to EM and ultrasound, other modalities can also be used. For example, in some embodiments, a depth sensor can be attached to a robotic arm. The depth sensor can be used to register the position of a patient, a bed or platform, a fluoroscopic C-arm used during the procedure, and/or other items in the surgical space to the global robot reference frame. In some embodiments, these positions can be represented as a heat map or point cloud, as shown in FIGS. 51A and 51B respectively. A depth sensor camera, for example as shown in FIG. 51C, can be configured to measure the distance to objects within a field of view thereof. Calibration for the depth sensor (for example, to register the output of the depth sensor to a robotic coordinate frame or the global coordinate frame) can proceed in the same manner as calibration of the ultrasound probe described above. In general, the depth sensor is calibrated by the manufacturer with respect to pixel and depth information. For use with a robotic system, for example, as described herein, it may be needed to calibrate the pose of the depth sensor with respect to robotic frame, which as mentioned above, can be accomplished in a similar manner as for the previously described ultrasound probe.

In some embodiments, a robotic medical system can utilize a plurality of different sensor functionalities in combination with each other. For example, a system can include an ultrasound probe, a camera or depth sensor, and an EM field generator, the output of each of which can be calibrated and registered to the robotic or global coordinate frame. In these embodiments, the ultrasound probe can provide imaging data relative to inside the patient's body. Similarly, the camera or depth sensor can provide imaging or other information about the external anatomy, for example, the position of the patient as well as external devices located in the operating room, such as C-arm. This can be advantageous as knowing where the patient is with respect to the robotic coordinate frame can allow the system to identify a needle insertion site, for example. Additionally, knowing the position of other items in the operation room with respect to the robotic coordinate frame, such as the C-arm, can allow the system to know when objects are close to the field generator, which may cause distortion.

3. Implementing Systems and Terminology.

Implementations disclosed herein provide systems, methods and apparatus for robotically controllable field generators.

It should be noted that the terms "couple," "coupling," "coupled" or other variations of the word couple as used herein may indicate either an indirect connection or a direct connection. For example, if a first component is "coupled" to a second component, the first component may be either indirectly connected to the second component via another component or directly connected to the second component.

The phrases referencing specific computer-implemented processes and functions described herein may be stored as one or more instructions on a processor-readable or computer-readable medium. The term "computer-readable medium" refers to any available medium that can be accessed by a computer or processor. By way of example, and not limitation, such a medium may comprise random access memory (RAM), read-only memory (ROM), electrically erasable programmable read-only memory (EEPROM), flash memory, compact disc read-only memory (CD-ROM) or other optical disk storage, magnetic disk storage or other magnetic storage devices, or any other medium that can be used to store desired program code in the form of instructions or data structures and that can be accessed by a computer. It should be noted that a computer-readable medium may be tangible and non-transitory. As used herein, the term "code" may refer to software, instructions, code or data that is/are executable by a computing device or processor.

The methods disclosed herein comprise one or more steps or actions for achieving the described method. The method steps and/or actions may be interchanged with one another without departing from the scope of the claims. In other words, unless a specific order of steps or actions is required for proper operation of the method that is being described, the order and/or use of specific steps and/or actions may be modified without departing from the scope of the claims.

As used herein, the term "plurality" denotes two or more. For example, a plurality of components indicates two or more components. The term "determining" encompasses a wide variety of actions and, therefore, "determining" can include calculating, computing, processing, deriving, investigating, looking up (e.g., looking up in a table, a database or another data structure), ascertaining and the like. Also, "determining" can include receiving (e.g., receiving information), accessing (e.g., accessing data in a memory) and the like. Also, "determining" can include resolving, selecting, choosing, establishing and the like.

The phrase "based on" does not mean "based only on," unless expressly specified otherwise. In other words, the phrase "based on" describes both "based only on" and "based at least on."

The previous descriptions of the disclosed implementations are provided to enable any person skilled in the art to make or use the present inventions disclosed herein. Various modifications to these implementations will be readily apparent to those skilled in the art, and the generic principles defined herein may be applied to other implementations without departing from the scope of the invention. For example, it will be appreciated that one of ordinary skill in the art will be able to employ a number corresponding alternative and equivalent structural details, such as equivalent ways of fastening, mounting, coupling, or engaging tool components, equivalent mechanisms for producing particular actuation motions, and equivalent mechanisms for delivering electrical energy. Thus, the disclosure herein is not intended to be limited to the implementations explicitly described but is to be accorded the widest scope consistent with the principles and novel features disclosed herein.

What is claimed is:

1. A robotic medical system, comprising:
   a first robotic arm coupled to an electromagnetic (EM) field generator configured to generate an EM field;
   an EM sensor; and
   one or more processors configured to:
      transmit a command to the first robotic arm to cause movement of the EM field generator along a robotic trajectory while the EM sensor remains at a location;
      detect an EM sensor trajectory of the EM sensor within the EM field corresponding to a period of time in which the EM field generator moved along the robotic trajectory;
      analyze the robotic trajectory and the EM sensor trajectory to determine a difference between the robotic trajectory and the EM sensor trajectory; and
      determine a presence of an EM distortion at the location based at least in part on the difference between the robotic trajectory and the EM sensor trajectory being greater than a threshold.

2. The system of claim 1, wherein the one or more processors are configured to determine the robotic trajectory based on kinematic data corresponding to the first robotic arm.

3. The system of claim 1, wherein the one or more processors are configured to determine the threshold based on at least one of an error factor associated with a movement of the first robotic arm or an error factor associated with EM sensor noise.

4. The system of claim 1, wherein the one or more processors are configured to determine the difference between the robotic trajectory and the EM sensor trajectory based on a comparison of a shape of the robotic trajectory to a shape of the EM sensor trajectory.

5. The system of claim 1, wherein the one or more processors are configured to determine the difference between the robotic trajectory and the EM sensor trajectory based on a comparison of a plurality of points along the robotic trajectory to a corresponding plurality of points along the EM sensor trajectory.

6. The system of claim 5, wherein each of the plurality of points are determined with respect to a time associated with the movement of the EM field generator.

7. The system of claim 1, wherein the one or more processors are further configured to, upon determining the presence of the EM distortion at the location, reposition the EM field generator with the first robotic arm to reduce the EM distortion at the location.

8. The system of claim 7, wherein the one or more processors are configured to reposition the EM field generator with the first robotic arm to reduce the EM distortion at the location by being configured to:
 transmit an additional command to the first robotic arm to cause movement of the EM field generator along a second robotic trajectory while the EM sensor remains at the location;
 detect a second EM sensor trajectory of the EM sensor within the EM field corresponding to a period of time in which the EM field generator moved along the second robotic trajectory;
 analyze the second robotic trajectory and the second EM sensor trajectory to determine a difference between the second robotic trajectory and the second EM sensor trajectory; and
 compare the difference between the second robotic trajectory and the second EM sensor trajectory and the difference between the robotic trajectory and the EM sensor trajectory.

9. The system of claim 8, wherein the one or more processors are configured to position the EM field generator at a point along the second robotic trajectory when the difference between the second robotic trajectory and the second EM sensor trajectory is less than the difference between the robotic trajectory and the EM sensor trajectory.

10. A method performed by a set of one or more processors of a robotic system, the method comprising:
 commanding a first robotic arm to move an electromagnetic (EM) field generator from a first location to a second location while an EM sensor remains at a location;
 determining a robotic trajectory associated with the EM field generator moving from the first location to the second location;
 detecting an EM sensor trajectory of the EM sensor within an EM field, the EM sensor trajectory being associated with a time period in which the EM field generator moved along the robotic trajectory;
 determining a difference between the robotic trajectory and the EM sensor trajectory; and
 determining a presence of an EM distortion at the location based at least in part on the difference between the robotic trajectory and the EM sensor trajectory being greater than a distortion threshold.

11. The method of claim 10, wherein determining the robotic trajectory further is based on using kinematic data corresponding to the first robotic arm.

12. The method of claim 10, wherein determining the robotic trajectory associated with the EM field generator moving from the first location to the second location includes compensating for an error factor associated with a movement of the first robotic arm.

13. The method of claim 10, wherein detecting the EM sensor trajectory includes compensating for an error factor associated with EM sensor noise.

14. The method of claim 10, wherein determining the difference between the robotic trajectory and the EM sensor trajectory further comprises comparing a shape of the robotic trajectory to a shape of the EM sensor trajectory.

15. The method of claim 10, wherein determining the difference between the robotic trajectory and the EM sensor trajectory further comprises comparing a plurality of points along the robotic trajectory to a corresponding plurality of points along the EM sensor trajectory.

16. The method of claim 15, wherein each of the plurality of points are determined with respect to a time associated with the movement of the EM field generator.

17. The method of claim 10, further comprises, upon determining the presence of the EM distortion at the location, repositioning the EM field generator with the first robotic arm to reduce the EM distortion at the location.

18. The method of claim 10, further comprising:
 commanding the first robotic arm to cause movement of the EM field generator along a second robotic trajectory while the EM sensor remains at the location;
 detecting a second EM sensor trajectory of the EM sensor within the EM field, the second EM sensor trajectory being associated with a time period in which the EM field generator moved along the second robotic trajectory;
 analyzing the second robotic trajectory and the second EM sensor trajectory to determine a difference between the second robotic trajectory and the second EM sensor trajectory; and
 comparing the difference between the second robotic trajectory and the second EM sensor trajectory and the difference between the robotic trajectory and the EM sensor trajectory.

19. The method of claim 18, further comprising positioning the EM field generator at a point along the second robotic trajectory when the difference between the second robotic trajectory and the second EM sensor trajectory is less than the difference between the robotic trajectory and the EM sensor trajectory.

20. A non-transitory computer readable storage medium comprising computer program instructions that when executed by one or more processors cause the one or more processors to:
 transmit a command to a first robotic arm to cause movement of an electromagnetic (EM) field generator along a robotic trajectory while an EM sensor remains at a location, the first robotic arm coupled to the EM field generator configured to generate the EM field;
 detect an EM sensor trajectory of the EM sensor within the EM field corresponding to a period of time in which the EM field generator moved along the robotic trajectory;
 analyze the robotic trajectory and the EM sensor trajectory to determine a difference between the robotic trajectory and the EM sensor trajectory; and
 determine a presence of an EM distortion at the location based at least in part on the difference between the robotic trajectory and the EM sensor trajectory being greater than a threshold.

* * * * *